United States Patent
Neely

(10) Patent No.: US 11,098,378 B2
(45) Date of Patent: Aug. 24, 2021

(54) COMPOSITIONS AND METHODS FOR DETECTION OF CANDIDA SPECIES

(71) Applicant: T2 Biosystems, Inc., Lexington, MA (US)

(72) Inventor: Lori Anne Neely, Reading, MA (US)

(73) Assignee: T2 Biosystems, Inc., Lexington, MA (US)

( * ) Notice: Subject to any disclaimer, the term of this patent is extended or adjusted under 35 U.S.C. 154(b) by 0 days.

(21) Appl. No.: 15/404,756

(22) Filed: Jan. 12, 2017

(65) Prior Publication Data
US 2017/0204475 A1    Jul. 20, 2017

Related U.S. Application Data

(62) Division of application No. 13/828,637, filed on Mar. 14, 2013, now Pat. No. 9,562,271.

(60) Provisional application No. 61/636,110, filed on Apr. 20, 2012.

(51) Int. Cl.
*C12Q 1/6895* (2018.01)
*C12Q 1/6818* (2018.01)

(52) U.S. Cl.
CPC ......... *C12Q 1/6895* (2013.01); *C12Q 1/6818* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | |
|---|---|---|
| 4,072,578 A | 2/1978 | Cady et al. |
| 4,101,435 A | 7/1978 | Hasegawa et al. |
| 4,295,613 A | 10/1981 | Moore et al. |
| 4,374,360 A | 2/1983 | Sepponen |
| 4,452,773 A | 6/1984 | Molday |
| 4,471,306 A | 9/1984 | Edelstein et al. |
| 4,485,177 A | 11/1984 | Siedel et al. |
| 4,578,361 A | 3/1986 | Siedel et al. |

(Continued)

FOREIGN PATENT DOCUMENTS

| | | |
|---|---|---|
| EP | 0574267 A2 | 12/1993 |
| EP | 0864863 A2 | 9/1998 |

(Continued)

OTHER PUBLICATIONS

Laalkargaretal. Feb. 2013. Genbank Accession No. KC422427.1, "Candida albicans strain Hb40 internal transcribed spacer 1; 5.8S ribosomal RNA gene, complete sequence; and internal transcribed spacer 2, partial sequence", 2 pages.*

(Continued)

*Primary Examiner* — Diana B Johannsen
(74) *Attorney, Agent, or Firm* — Clark & Elbing LLP

(57) ABSTRACT

The invention features compositions and methods for the detection of *Candida* species in biological samples, such as human tissue samples. The invention features species specific nucleic acid probes that can hybridize to target nucleic acid molecules in *Candida* species and can be used in a variety of detection assays, such as fluorescence based assays or NMR based assays. The compositions and methods of the invention can be used to rapidly and accurately detect one or more *Candida* species in patients and can be used to assist in point-of care-decisions for treating *Candida* infections.

23 Claims, 16 Drawing Sheets

Specification includes a Sequence Listing.

(56) References Cited

U.S. PATENT DOCUMENTS

| | | |
|---|---|---|
| D284,214 S | 6/1986 | Hatcher et al. |
| D285,118 S | 8/1986 | Huang |
| D288,479 S | 2/1987 | Covell et al. |
| 4,683,195 A | 7/1987 | Mullis et al. |
| 4,683,202 A | 7/1987 | Mullis |
| 4,745,077 A | 5/1988 | Holian et al. |
| D303,711 S | 9/1989 | DesRosier et al. |
| 4,875,486 A | 10/1989 | Rapoport et al. |
| 4,889,818 A | 12/1989 | Gelfand et al. |
| 4,920,061 A | 4/1990 | Poynton et al. |
| 4,965,188 A | 10/1990 | Mullis et al. |
| 5,038,852 A | 8/1991 | Johnson et al. |
| 5,049,819 A | 9/1991 | Dechene et al. |
| 5,066,584 A | 11/1991 | Gyllensten et al. |
| 5,079,352 A | 1/1992 | Gelfand et al. |
| 5,135,875 A | 8/1992 | Meucci et al. |
| 5,136,095 A | 8/1992 | Tarnowski et al. |
| D330,085 S | 10/1992 | Crerar et al. |
| 5,164,297 A | 11/1992 | Josephson et al. |
| 5,164,495 A | 11/1992 | Lunetta |
| D332,145 S | 12/1992 | Wada et al. |
| 5,204,457 A | 4/1993 | Maruno et al. |
| 5,229,297 A | 7/1993 | Schnipelsky et al. |
| 5,247,076 A | 9/1993 | Goulet et al. |
| 5,252,732 A | 10/1993 | Sinclair et al. |
| 5,254,460 A | 10/1993 | Josephson et al. |
| 5,262,176 A | 11/1993 | Palmacci et al. |
| D345,611 S | 3/1994 | Long |
| 5,333,675 A | 8/1994 | Mullis et al. |
| 5,338,684 A | 8/1994 | Grenier et al. |
| 5,352,600 A | 10/1994 | Gelfand et al. |
| 5,424,419 A | 6/1995 | Hasegawa et al. |
| 5,426,026 A | 6/1995 | Jordan |
| 5,426,027 A | 6/1995 | Lott et al. |
| 5,436,149 A | 7/1995 | Barnes |
| 5,445,970 A | 8/1995 | Rohr |
| 5,445,971 A | 8/1995 | Rohr |
| 5,475,610 A | 12/1995 | Atwood et al. |
| D366,529 S | 1/1996 | Babaoglu et al. |
| 5,492,814 A | 2/1996 | Weissleder |
| 5,508,164 A | 4/1996 | Kausch et al. |
| 5,512,439 A | 4/1996 | Hornes et al. |
| 5,532,137 A | 7/1996 | Niwa et al. |
| 5,543,305 A | 8/1996 | Cummins et al. |
| 5,578,325 A | 11/1996 | Domb et al. |
| 5,599,498 A | 2/1997 | Oh |
| 5,618,926 A | 4/1997 | Salamone et al. |
| 5,631,132 A | 5/1997 | Lott et al. |
| 5,635,353 A | 6/1997 | Lott et al. |
| 5,635,406 A | 6/1997 | Grenier et al. |
| 5,637,469 A | 6/1997 | Wilding et al. |
| 5,650,288 A | 7/1997 | MacFarlane et al. |
| 5,656,493 A | 8/1997 | Mullis et al. |
| 5,677,133 A | 10/1997 | Oberhardt |
| 5,688,644 A | 11/1997 | Lott et al. |
| 5,698,448 A | 12/1997 | Soldin |
| 5,705,628 A | 1/1998 | Hawkins |
| 5,708,159 A | 1/1998 | Ohno et al. |
| 5,711,871 A | 1/1998 | Miltenyi |
| 5,773,307 A | 6/1998 | Colin et al. |
| 5,776,696 A | 7/1998 | Salowe |
| 5,801,003 A | 9/1998 | Shimamura et al. |
| 5,804,375 A | 9/1998 | Gelfand et al. |
| 5,837,501 A | 11/1998 | Beumer et al. |
| 5,858,534 A | 1/1999 | Sucholeiki |
| 5,898,071 A | 4/1999 | Hawkins |
| 5,910,409 A | 6/1999 | Bhattacharjee et al. |
| 5,935,825 A | 8/1999 | Nishimura et al. |
| D414,561 S | 9/1999 | Escoffier |
| 5,973,138 A | 10/1999 | Collis |
| D416,330 S | 11/1999 | Brown |
| 5,994,056 A | 11/1999 | Higuchi |
| 6,007,845 A | 12/1999 | Domb et al. |
| 6,013,188 A | 1/2000 | Terstappen et al. |
| 6,020,211 A | 2/2000 | Tuunanen |
| 6,030,845 A | 2/2000 | Yamao et al. |
| 6,040,166 A | 3/2000 | Erlich et al. |
| 6,097,188 A | 8/2000 | Sweedler et al. |
| 6,127,155 A | 10/2000 | Gelfand et al. |
| 6,130,045 A | 10/2000 | Wurst et al. |
| 6,136,549 A | 10/2000 | Feistel |
| 6,143,578 A | 11/2000 | Bendele et al. |
| 6,159,378 A | 12/2000 | Holman et al. |
| 6,165,378 A | 12/2000 | Maruno et al. |
| 6,187,547 B1 | 2/2001 | Legay et al. |
| 6,194,900 B1 | 2/2001 | Freeman et al. |
| D438,632 S | 3/2001 | Miller |
| 6,197,563 B1 | 3/2001 | Erlich et al. |
| 6,235,890 B1 | 5/2001 | Morrison et al. |
| 6,242,178 B1 | 6/2001 | Lott et al. |
| 6,294,342 B1 | 9/2001 | Rohr et al. |
| 6,297,062 B1 | 10/2001 | Gombinski |
| D452,740 S | 1/2002 | Brennan et al. |
| 6,338,946 B1 | 1/2002 | Kobayashi et al. |
| 6,342,396 B1 | 1/2002 | Perrin et al. |
| 6,346,813 B1 | 2/2002 | Kleinberg |
| 6,361,944 B1 | 3/2002 | Mirkin et al. |
| 6,423,490 B1 | 7/2002 | Takama |
| 6,456,072 B1 | 9/2002 | Webb et al. |
| 6,489,767 B1 | 12/2002 | Prado et al. |
| 6,500,343 B2 | 12/2002 | Siddiqi |
| 6,514,736 B1 | 2/2003 | Erlich et al. |
| 6,548,311 B1 | 4/2003 | Knoll |
| 6,566,086 B1 | 5/2003 | Al Athel et al. |
| 6,599,498 B1 | 7/2003 | Groman et al. |
| 6,605,439 B2 | 8/2003 | Einsele |
| 6,630,355 B1 | 10/2003 | Pivarnik et al. |
| 6,654,636 B1 | 11/2003 | Dev et al. |
| 6,686,195 B1 | 2/2004 | Colin et al. |
| 6,686,454 B1 | 2/2004 | Yatscoff et al. |
| D492,419 S | 6/2004 | Farina |
| 6,767,635 B1 | 7/2004 | Bahr et al. |
| 6,768,305 B1 | 7/2004 | Keifer |
| 6,788,061 B1 | 9/2004 | Sweedler et al. |
| 6,822,452 B2 | 11/2004 | Ham et al. |
| 6,822,454 B2 | 11/2004 | Peck et al. |
| 6,866,838 B1 | 3/2005 | Mondain-Monval et al. |
| 6,872,523 B1 | 3/2005 | Iwen et al. |
| 6,884,357 B2 | 4/2005 | Siddiqi |
| 6,890,765 B2 | 5/2005 | Lawrence et al. |
| 6,940,378 B2 | 9/2005 | Miller et al. |
| 6,958,609 B2 | 10/2005 | Raftery et al. |
| 7,001,589 B2 | 2/2006 | Mondain-Monval et al. |
| D516,732 S | 3/2006 | Sakurai et al. |
| 7,018,849 B2 | 3/2006 | Piasio et al. |
| 7,036,667 B2 | 5/2006 | Greenstein et al. |
| 7,037,688 B2 | 5/2006 | Salituro et al. |
| 7,049,558 B2 | 5/2006 | Baer et al. |
| 7,078,495 B1 | 7/2006 | Kasper et al. |
| 7,164,077 B2 | 1/2007 | Venkatasubramanian |
| 7,169,556 B2 | 1/2007 | Park et al. |
| 7,186,518 B2 | 3/2007 | Wang et al. |
| 7,200,430 B2 | 4/2007 | Thomas et al. |
| 7,217,457 B2 | 5/2007 | Elaissari et al. |
| 7,217,542 B2 | 5/2007 | Tyvoll et al. |
| 7,274,191 B2 | 9/2007 | Park et al. |
| 7,332,353 B2 | 2/2008 | Baudry et al. |
| 7,397,241 B2 | 7/2008 | Gauthausen et al. |
| 7,459,145 B2 | 12/2008 | Bao et al. |
| 7,462,475 B2 | 12/2008 | Kermekchiev et al. |
| 7,494,771 B2 | 2/2009 | Picard et al. |
| 7,517,457 B2 | 4/2009 | Siddiqi |
| 7,553,542 B2 | 6/2009 | Ou et al. |
| 7,560,923 B2 | 7/2009 | Viswanathan |
| 7,564,245 B2 | 7/2009 | Lee |
| 7,575,875 B2 | 8/2009 | Konrath et al. |
| 7,615,381 B2 | 11/2009 | Masters et al. |
| 7,651,837 B2 | 1/2010 | Ohno et al. |
| 7,670,780 B2 | 3/2010 | Hogan et al. |
| 7,704,735 B2 | 4/2010 | Facer et al. |
| 7,723,095 B2 | 5/2010 | Cleuziat et al. |
| 7,781,228 B2 | 8/2010 | Menon et al. |
| 7,829,350 B2 | 11/2010 | Josephson et al. |
| 7,867,766 B2 | 1/2011 | Wang |

(56) References Cited

U.S. PATENT DOCUMENTS

| | | |
|---|---|---|
| D632,803 S | 2/2011 | Motadel et al. |
| 7,906,286 B2 | 3/2011 | Fukui et al. |
| 8,044,001 B2 | 10/2011 | Putzig |
| 8,049,001 B2 | 11/2011 | Tomatsu et al. |
| D657,473 S | 4/2012 | Miyashita et al. |
| D674,112 S | 1/2013 | Demas et al. |
| 8,409,807 B2 | 4/2013 | Neely et al. |
| 8,563,298 B2 | 10/2013 | Lowery, Jr. et al. |
| 8,883,423 B2 | 11/2014 | Neely |
| 9,046,493 B2 | 6/2015 | Neely et al. |
| 9,702,852 B2 | 7/2017 | Lowery, Jr. et al. |
| 9,714,940 B2 | 7/2017 | Lowery, Jr. et al. |
| 9,932,574 B2 | 4/2018 | Burghardt et al. |
| 2002/0051974 A1 | 5/2002 | Dodge et al. |
| 2003/0054370 A1 | 3/2003 | Zeng et al. |
| 2003/0069180 A1 | 4/2003 | Jiang et al. |
| 2003/0092029 A1 | 5/2003 | Josephson et al. |
| 2003/0207296 A1 | 11/2003 | Park et al. |
| 2003/0216638 A1 | 11/2003 | Dharmakumar et al. |
| 2003/0222648 A1 | 12/2003 | Fan |
| 2004/0018611 A1 | 1/2004 | Ward et al. |
| 2004/0076990 A1 | 4/2004 | Picard et al. |
| 2004/0141887 A1 | 7/2004 | Mainquist et al. |
| 2004/0166492 A1 | 8/2004 | Engel et al. |
| 2005/0142033 A1 | 6/2005 | Glezer et al. |
| 2005/0176080 A1 | 8/2005 | Bodepudi et al. |
| 2006/0051770 A1 | 3/2006 | Makeev |
| 2006/0234219 A1 | 10/2006 | Ohno et al. |
| 2006/0269965 A1 | 11/2006 | Josephson et al. |
| 2007/0027309 A1 | 2/2007 | Weinstock et al. |
| 2007/0083945 A1 | 4/2007 | Byrum et al. |
| 2007/0111330 A1 | 5/2007 | Hong et al. |
| 2007/0116602 A1 | 5/2007 | Lee |
| 2007/0166730 A1 | 7/2007 | Menon et al. |
| 2007/0190543 A1 | 8/2007 | Livak |
| 2007/0292891 A1 | 12/2007 | Wei et al. |
| 2008/0008996 A1 | 1/2008 | Byrum |
| 2008/0020401 A1 | 1/2008 | Grenier et al. |
| 2008/0056948 A1 | 3/2008 | Dale et al. |
| 2008/0081379 A1 | 4/2008 | Sigler et al. |
| 2008/0102449 A1 | 5/2008 | Trama et al. |
| 2008/0124722 A1 | 5/2008 | Dromaretsky et al. |
| 2008/0160499 A1 | 7/2008 | Grenier et al. |
| 2008/0176756 A1 | 7/2008 | Siegel et al. |
| 2008/0204022 A1 | 8/2008 | Sillerud et al. |
| 2008/0248970 A1 | 10/2008 | Morrison et al. |
| 2008/0305048 A1 | 12/2008 | Josephson et al. |
| 2008/0311676 A1 | 12/2008 | Brate et al. |
| 2009/0029392 A1 | 1/2009 | Josephson et al. |
| 2009/0042223 A1 | 2/2009 | Wei et al. |
| 2009/0054741 A1 | 2/2009 | McAleer |
| 2009/0077685 A1 | 3/2009 | Buehler et al. |
| 2009/0087865 A1 | 4/2009 | Kasper et al. |
| 2009/0099342 A1 | 4/2009 | Braconnot et al. |
| 2009/0119022 A1 | 5/2009 | Timberlake et al. |
| 2009/0134869 A1 | 5/2009 | Lee |
| 2009/0155929 A1 | 6/2009 | Wei et al. |
| 2009/0170060 A1 | 7/2009 | Kermekchiev et al. |
| 2009/0239308 A1 | 9/2009 | Dube et al. |
| 2009/0253210 A1 | 10/2009 | Kobold et al. |
| 2009/0298090 A1 | 12/2009 | Drengler et al. |
| 2009/0298129 A1 | 12/2009 | Spence et al. |
| 2009/0325193 A1 | 12/2009 | Grenier et al. |
| 2009/0325197 A1 | 12/2009 | Drengler et al. |
| 2009/0325198 A1 | 12/2009 | Holets-McCormack |
| 2010/0062090 A1 | 3/2010 | Kim et al. |
| 2010/0072994 A1 | 3/2010 | Lee et al. |
| 2010/0092979 A1 | 4/2010 | Kelso et al. |
| 2010/0099746 A1 | 4/2010 | Yamada et al. |
| 2010/0120174 A1 | 5/2010 | Josephson et al. |
| 2010/0124766 A1 | 5/2010 | Ng et al. |
| 2010/0129821 A1 | 5/2010 | Fredricks et al. |
| 2010/0219824 A1 | 9/2010 | Sillerud et al. |
| 2010/0259259 A1 | 10/2010 | Zahn et al. |
| 2011/0003285 A1 | 1/2011 | Niwa |
| 2011/0245094 A1 | 10/2011 | Washburn et al. |
| 2012/0100546 A1 | 4/2012 | Lowery, Jr. et al. |
| 2012/0301888 A1 | 11/2012 | Neely et al. |
| 2013/0029345 A1 | 1/2013 | Neely et al. |
| 2013/0229179 A1 | 9/2013 | Lee |
| 2013/0244238 A1 | 9/2013 | Neely et al. |
| 2013/0260367 A1 | 10/2013 | Lowery, Jr. et al. |
| 2013/0266944 A1 | 10/2013 | Neely et al. |
| 2013/0273522 A1 | 10/2013 | Lowery, Jr. et al. |
| 2013/0273523 A1 | 10/2013 | Neely et al. |
| 2014/0191109 A1 | 7/2014 | Chamberlin et al. |
| 2017/0233798 A1 | 8/2017 | Neely et al. |

FOREIGN PATENT DOCUMENTS

| | | |
|---|---|---|
| EP | 1870449 A1 | 12/2007 |
| EP | 2410052 A1 | 1/2012 |
| JP | 2009-506345 A | 2/2009 |
| JP | 2009-537167 A | 10/2009 |
| JP | 2010-30915 A | 2/2010 |
| WO | WO-90/06045 A2 | 6/1990 |
| WO | WO-91/17428 A1 | 11/1991 |
| WO | WO-97/40181 A1 | 10/1997 |
| WO | WO-98/04740 A1 | 2/1998 |
| WO | WO-01/00876 A1 | 1/2001 |
| WO | WO-01/11360 A2 | 2/2001 |
| WO | WO-01/19405 A2 | 3/2001 |
| WO | WO-01/55719 A2 | 8/2001 |
| WO | WO-02/098364 A2 | 12/2002 |
| WO | WO-2004/029216 A2 | 4/2004 |
| WO | WO-2005/061724 A1 | 7/2005 |
| WO | WO-2005/099419 A2 | 10/2005 |
| WO | WO-2005/111596 A1 | 11/2005 |
| WO | WO-2006/013844 A1 | 2/2006 |
| WO | WO-2006/122083 A2 | 11/2006 |
| WO | WO-2006/138444 A2 | 12/2006 |
| WO | WO-2007/023461 A2 | 3/2007 |
| WO | WO-2007/027843 A2 | 3/2007 |
| WO | WO-2007/097473 A1 | 8/2007 |
| WO | WO-2007/106765 A2 | 9/2007 |
| WO | WO-2007/134294 A2 | 11/2007 |
| WO | WO-2007/135332 A1 | 11/2007 |
| WO | WO-2008/003451 A1 | 1/2008 |
| WO | WO-2008/007270 A2 | 1/2008 |
| WO | WO-2008/010111 A2 | 1/2008 |
| WO | WO-2008/054517 A2 | 5/2008 |
| WO | WO-2008/072156 A2 | 6/2008 |
| WO | WO-2008/078579 A1 | 7/2008 |
| WO | WO-2008/119054 A1 | 10/2008 |
| WO | WO-2008/137721 A2 | 11/2008 |
| WO | WO-2009/004551 A1 | 1/2009 |
| WO | WO-2009/005178 A1 | 1/2009 |
| WO | WO-2009/017697 A2 | 2/2009 |
| WO | WO-2009/025475 A2 | 2/2009 |
| WO | WO-2009/026164 A1 | 2/2009 |
| WO | WO-2009/026251 A1 | 2/2009 |
| WO | WO-2009/045354 A1 | 4/2009 |
| WO | WO-2009/045551 A1 | 4/2009 |
| WO | WO-2009/055587 A1 | 4/2009 |
| WO | WO-2009/061481 A1 | 5/2009 |
| WO | WO-2009/078875 A1 | 6/2009 |
| WO | WO-2009/085214 A1 | 7/2009 |
| WO | WO-2010/002479 A1 | 1/2010 |
| WO | WO-2010/034846 A1 | 4/2010 |
| WO | WO-2010/051362 A1 | 5/2010 |
| WO | WO-2010/062909 A1 | 6/2010 |
| WO | WO-2011/030091 A1 | 3/2011 |
| WO | WO-2011/053241 A1 | 5/2011 |
| WO | WO-2011/121288 A2 | 10/2011 |

OTHER PUBLICATIONS

Ahmad et al., "Seminested PCR for diagnosis of candidemia: comparison with culture, antigen detection, and biochemical methods for species identification," J Clin Microbiol. 40(7):2483-9 (2002).

Alhassan et al., "Comparison of polymerase chain reaction methods for the detection of Theileria equi infection using whole blood

(56) References Cited

OTHER PUBLICATIONS compared with pre-extracted DNA samples as PCR templates," Trop Anim Health Prod. 39(5):369-74 (2007).
Allice et al., "Evaluation of a novel real-time PCR system for cytomegalovirus DNA quantitation on whole blood and correlation with pp65-antigen test in guiding pre-emptive antiviral treatment," J Virol Methods. 148(1-2):9-16 (2008).
Altschul et al., "Basic local alignment search tool," J Mol Biol. 215(3):403-10 (1990).
Amaral et al., "Coagulation in sepsis," Intensive Care Med. 30(6):1032-40 (2004).
Aoki et al., "Detection of Legionella DNA by PCR of whole-blood samples in a mouse model," J Med Microbiol. 52(Pt 4):325-329 (2003).
Atanasijevic et al., "Calcium-sensitive MRI contrast agents based on superparamagnetic iron oxide nanoparticles and calmodulin," Proc Natl Acad Sci USA. 103(40):14707-14712 (2006).
Attal et al., "A simple method of DNA extraction from whole tissues and blood using glass powder for detection of transgenic animals by PCR," Transgenic Res. 4(2):149-150 (1995).
Awduche et al., "RSVP-TE: Extensions to Rsvp for LSP Tunnels," IETF Standard, Internet Engineering Task Force (Dec. 2001) (62 pages).
Barany, "Genetic disease detection and DNA amplification using cloned thermostable ligase," Proc Natl Acad Sci USA. 88(1):189-193 (1991).
Baudry et al., "Acceleration of the recognition rate between grafted ligands and receptors with magnetic forces," Proc Natl Acad Sci USA. 103(44):16076-16078 (2006).
Baugher et al., "Evaluation of the Tacrolimus Assay on the Abbott Architect® Analyzer," American Association for Clinical Chemistry Annual Meeting, Chicago, Illinois Jul. 23-27 (4 pages) (2006).
Benkert et al., "Development of a creatinine ELISA and an amperometric antibody-based creatinine sensor with a detection limit in the nanomolar range," Anal Chem. 72(5):916-921 (2000).
Bergman et al., "Rapid identification of pathogenic yeast isolates by real-time PCR and two-dimensional melting point analysis," Eur J Clin Microbiol Infect Dis. 26(11):813-818 (2007).
NCBI Blast for Accession No. X53497.1. Retrieved on Apr. 14, 2012 (4 pages).
NCBI Blast for Accession No. AY198398.1. Retrieved on Apr. 14, 2012 (3 pages).
Boero et al., "An NMR Magnetometer with Planar Microcoils and Integrated Electronics for Signal Detection and Amplification," Sens and Actuators A. 67(1-3):18-23 (1998).
Bougnoux et al., "Serum is More Suitable than Whole Blood for Diagnosis of Systemic Candidiasis by Nested PCR," J. Clin. Microbiol. 37(4):925-930 (1999).
Brown et al., "Scaling of Transverse Nuclear Magnetic Relaxation due to Magnetic Nanoparticle Aggregation" J Magn Magn Mater. 322(20):3122-3126 (2010).
Bu et al., "Direct Polymerase Chain Reaction (PCR) from Human Whole Blood and Filter-Paper-Dried Blood by Using a PCR Buffer with a Higher pH," Anal. Biochem. 375(2):370-372 (2008).
Buck et al., "Design strategies and performance of custom DNA sequencing primers," BioTechniques. 27(3):528-536 (1999).
Burckhardt, "Amplification of DNA from Whole Blood," PCR Methods Appl. 3(4):239-243 (1994).
Castley et al., "Clinical Applications of Whole-Blood PCR with Real-Time Instrumentation," Clin Chem. 51(11):2025-2030 (2005).
Cedervall et al., "Understanding the Nanoparticle-Protein Corona Using Methods to Quantify Exchange Rates and Affinities of Proteins for Nanoparticles," Proc Natl Acad Sci U S A. 104(7):2050-2055 (2007).
Cerikcioglu et al., "Seminested PCR for Detection and Identification of Candida Species Directly from Blood Culture Bottles," New Microbiol. 33(1):57-62 (2010).
Chaffin et al., "Cell Wall and Secreted Proteins of Candida Albicans: Identification, Function, and Expression," Microbiol Mol Biol Rev. 62(1):130-180 (1998).

Chisti et al., Chapter 13: Fermentation Technology, Bioprocessing, Scale-Up and Manufacture. *Biotechnology/The Science and the Business.* 177-222 (1999).
Chomczynski et al., "Alkaline Polyethylene Glycol-Based Method for Direct PCR from Bacteria, Eukaryotic Tissue Samples, and Whole Blood," BioTechniques 40(4):454,456,458 (2006).
Christians et al., Tacrolimus. Applied Pharmacokinetics and Pharmacodynamics: Principles of Therapeutic Drug Monitoring, Fourth Edition. Burton, Schentag, Shaw, and Evans, 527-562 (2006).
Cohen-Tannoudji et al., "Measuring the Kinetics of Biomolecular Recognition with Magnetic Colloids," Phys Rev Lett. 100(10):108301 (2008) (4 pages).
Colombo et al., "Femtomolar detection of autoantibodies by magnetic relaxation nanosensors." Anal Biochem. 392(1):96-102 (2009).
Costanzo et al., "Protein-Ligand Mediated Aggregation of Nanoparticles: A Study of Synthesis and Assembly Mechanism," Chem Mater. 16(9):1775-1785 (2004).
Curran et al., "The Killing of Bacterial Spores in Fluids by Agitation with Small Inert Particles," J Bacterial. 43(2):125-139 (1942).
D'Ambrosio et al., "Improved Procedures for Enzyme Immunoassay of Tacrolimus (FK506) in Whole Blood," Clin Chem. 40(1):159-160 (1994).
Daniel et al., "Multi-reservoir device for detecting a soluble cancer biomarker," Lab Chip. 7(10):1288-1293 (2007).
De Paula et al., "Optimizing Dengue Diagnosis by RT-PCR in IgM-Positive Samples: Comparison of Whole Blood, Buffy-Coat and Serum as Clinical Samples," J. Virol. Methods. 102(1-2):113-117 (2002).
de Vries et al., "PCR on Cell Lysates Obtained from Whole Blood Circumvents DNA Isolation," Clin. Chem. 47(9):1701-1702 (2001).
Deak et al., "Utility of a Luminex-based Assay for Multiplexed, Rapid Species Identification of Candida isolates from an Ongoing Candidemia Surveillance," Can J Microbiol. 56(4):348-351 (2010).
Deback et al., "Monitoring of Human Cytomegalovirus Infection in Immunosuppressed Patients Using Real-Time PCR on Whole Blood," J Clin Virol. 40(3):173-179 (2007).
Delgado et al., "Surface Properties of Polystyrene Nanoparticles Coated with Dextrans and Dextran-PEO Copolymers. Effect of Polymer Architecture on Protein Adsorption," Langmuir 17(14):4386-4391 (2001).
Demas et al., "Magnetic Resonance for In Vitro Medical Diagnostics: Superparamagnetic Nanoparticle-Based Magnetic Relaxation Switches," New J. Phys. 13:025005 (2011) (25 pages).
Demas et al., "Electronic characterization of lithographically patterned microcoils for high sensitivity NMR detection," J Magn Reson. 200(1):56-63 (2009).
Demas et al., "Portable, Low-Cost NMR with Laser-Lathe Lithography Produced Microcoils," J Magn Reson. 189(1):121-129 (2007).
Dreyfus et al., "Microscopic Artificial Swimmers," Nature. 437(7060):862-865 (2005).
Elie et al., "Rapid Identification of Candida Species with Species-Specific DNA Probes," J Clin Microbiol. 36(11):3260-3265 (1998).
Espy et al., "Real-Time PCR in Clinical Microbiology: Applications for Routine Laboratory Testing," Clin. Microbiol. Rev. 19(1):165-256 (2006).
Fossati et al., "Enzymic Creatinine Assay: A New Colorimetric Method Based on Hydrogen Peroxide Measurement," Clin Chem. 29(8):1494-1496 (1983).
Fry et al., "A New Approach to Template Purification for Sequencing Applications using Paramagnetic Particles," BioTechniques 13(1):124-126,128-131 (1992) (8 pages).
Fujita et al., "Microtitration plate enzyme immunoassay to detect PCR-amplified DNA from Candida species in blood," J Clin Microbiol. 33(4):962-967 (1995).
Garey et al., "Time to Initiation of Fluconazole Therapy Impacts Mortality in Patients with Candidemia: A Multi-Institutional Study," Clin Infect Dis. 43(1):25-31 (2006).
Garrigue et al., "Whole Blood Real-Time Quantitative PCR for Cytomegalovirus Infection Follow-Up in Transplant Recipients," J Clin Virol. 36(1):72-75 (2006).

(56) References Cited

OTHER PUBLICATIONS

George et al., "Effect of Inoculum Size on Detection of Candida Growth by the BACTEC 9240 Automated Blood Culture System Using Aerobic and Anaerobic Media," J Clin Microbiol. 43(1):433-435 (2005).
Gijs, "Magnetic Bead Handling On-chip: New Opportunities for Analytical Applications," Microfluid Nanofluid 1:22-40 (2004).
Gonschior et al., "Tacrolimus (FK506) Metabolite Patterns in Blood from Liver and Kidney Transplant Patients," Clin Chem 42(9):1426-1432 (1996).
Griffiths et al., "Comparison of DNA Extraction Methods for Aspergillus fumigatus Using Real-Time PCR," J Med Microbiol. 55(Pt 9):1187-1191 (2006).
Grimm et al., "Novel Nanosensors for Rapid Analysis of Telomerase Activity," Cancer Res. 64(2): 639-643 (2004).
Harris et al., "Proteolytic Actuation of Nanoparticle Self-assembly," Angew Chem Int Ed Engl. 45(19):3161-3165 (2006).
Hatch et al., "Magnetic Design Considerations for Devices and Particles Used for Biological High-Gradient Magnetic Separation (HGMS) Systems," J. Magnet. Mag. Mat. 225(1-2):262-276 (2001).
Hirose et al., "Simultaneous Cultivation and Disruption of *Escherichia coli* Using Glass Beads to Release Recombinant alpha-Amylase and Other Enzymes," Biotechnol Techniques 13(9):571-575 (1999).
Hong et al., "Magnetic Microparticle Aggregation for Viscosity Determination by MR," Magn Reson Med. 59(3):515-520 (2008).
Hoorfar et al., "Practical Considerations in Design of Internal Amplification Controls for Diagnostic PCR Assays," J. Clin. Microbiol. 42(5):1863-1868 (2004).
Horn et al., "Epidemiology and Outcomes of Candidemia in 2019 Patients: Data From the Prospective Antifungal Therapy Alliance Registry," Clin Infect Dis. 48(12):1695-1703 (2009).
Horvath et al., "Detection of Simulated Candidemia by the Bactec 9240 System with Plus Aerobic/F and Anaerobic/F Blood Culture Bottles," J. Clin. Microbiol. 41(10):4714-4717 (2003).
Inglis et al., "Microfluidic High Gradient Magnetic Cell Separation," J Appl Physics 99(8):08K101 (2006) (3 pages).
Josephson et al., "Magnetic Nanosensors for the Detection of Oligonucleotide Sequences," Angew. Chem. Int. Ed. 40(17):3204-3206 (2001).
Kaittanis et al., "One-step, nanoparticle-mediated bacterial detection with magnetic relaxation," Nano Lett. 7(2):380-3 (2007).
Keeney et al., "A Whole Blood, Multiplex PCR Detection Method for Factor V Leiden and the Prothrombin G20210A Variant," Thromb Haemost. 81(3):464-465 (1999).
Keevil et al., "Simultaneous and Rapid Analysis of Cyclosporin A and Creatinine in Finger Prick Blood Samples Using Liquid Chromatography Tandem Mass Spectrometry and its Application in C2 Monitoring," Ther Drug Monit. 24(6):757-767 (2002).
Kermekchiev et al., "Cold-sensitive Mutants of Taq DNA Polymerase Provide a Hot Start for PCR," Nucleic Acids Res. 31(21):6139-6147 (2003).
Kermekchiev et al., "Mutants of Taq DNA Polymerase Resistant to PCR Inhibitors Allow DNA Amplification from Whole Blood and Crude Soil Samples," Nucleic Acids Res. 37(5):e40 (2009) (14 pages).
Khot et al., "Sequencing and Analysis of Fungal rRNA Operons for Development of Broad-range Fungal PCR Assays," Appl Environ Microbiol. 75(6):1559-1565 (2009).
Kim et al., "Magnetic Relaxation Switch Detection of Human Chorionic Gonadotrophin," Bioconjug. Chem. 18(6):2024-2028 (2007).
Klungthong et al., "Dengue Virus Detection Using Whole Blood for Reverse Transcriptase PCR and Virus Isolation," J. Clin. Microbiol. 45(8):2480-2485 (2007).
Koh et al., "Magnetic nanoparticle sensors." Sensors. 9(10):8130-45 (2009).
Koh et al., "Nanoparticle-target interactions parallel antibody-protein interactions." Anal Chem. 81(9):3618-22 (2009).
"Sensitive NMR Sensors Detect Antibodies to Influenza," available in PMC Apr. 13, 2009, published in final edited form as: Angew Chem Int Ed Engl. 47(22):4119-4121 (2008) (8 pages).
Kost et al., "Multicenter Study of Whole-Blood Creatinine, Total Carbon Dioxide Content, and Chemistry Profiling for Laboratory and Point-of-Care Testing in Critical Care in the United States," Crit Care Med. 28(7):2379-2389 (2000).
Kötitz et al., "Determination of the Binding Reaction between Avidin and Biotin by Relaxation Measurements of Magnetic Nanoparticles," J. Magn. Magn. Mater. 194(1-3):62-68 (1999).
Kriz et al., "Advancements Toward Magneto Immunoassays," Biosens Bioelectron. 13(7-8):817-823 (1998).
Kriz et al., "Magnetic Permeability Measurements in Bioanalysis and Biosensors," Anal Chem. 68(11):1966-1970 (1996).
Kroll et al., "Mechanism of Interference with the Jaffé Reaction for Creatinine," Clin. Chem. 33(7):1129-1132 (1987).
Kula et al., "Purification of Proteins and the Disruption of Microbial Cells," Biotechnol. Progress 3(1):31-42 (1987).
Kulkarni et al., "Detection of Carbohydrate Binding Proteins Using Magnetic Relaxation Switches," Anal Chem. 82(17):7430-7435 (2010) (6 pages).
Kumar et al., "Initiation of Inappropriate Antimicrobial Therapy Results in a Fivefold Reduction of Survival in Human Septic Shock," Chest. 136(5):1237-1248 (2009).
Kumari et al., "Surface Oxidation of Nickel Thin Films," J Mater Sci Lett. 11(11):761-762 (1992).
Lacharme et al., "Full On-Chip Nanoliter Immunoassay by Geometrical Magnetic Trapping of Nanoparticle Chains," Anal Chem. 80(8):2905-2910 (2008).
Lamanna et al., "Use of Glass Beads for the Mechanical Rupture of Microorganisms in Concentrated Suspensions," J Bacteriol. 67(4):503-504 (1954).
Lee et al., "Exclude Routes-Extension to RSVP-TE," CCAMP Working Group (2003) (13 pages).
Lee et al., "Rapid Detection and Profiling of Cancer Cells in Fine-needle Aspirates" Proc Natl Acad Sci U.S.A. 106(30):12459-12464 (2009).
"Ultrasensitive Detection of Bacteria using Core-shell Nanoparticles and a NMR-Filter System," available in PMC Aug. 11, 2009, published in final edited form as: Angew Chem Int Ed Engl. 48(31):5657-5660 (2009) (10 pages).
Lee et al., "Ligand-Receptor Interactions in Chains of Colloids: When Reactions are Limited by Rotational Diffusion," Langmuir. 24(4):1296-1307 (2008).
Lee et al., "Microelectromagnets for the Control of Magnetic Nanoparticles," Appl Phys Lett. 79(20):3308-3310 (2001).
Lee et al., "Sequence-specific electrochemical detection of asymmetric PCR amplicons of traditional Chinese medicinal plant DNA," Anal Chem. 74(19):5057-5062 (2002).
Lehmann et al., "A Multiplex Real-Time PCR Assay for Rapid Detection and Differentiation of 25 Bacterial and Fungal Pathogens from Whole Blood Samples," Med Microbiol Immunol. 197(3):313-324 (2008).
Levey et al., "Using Standardized Serum Creatinine Values in the Modification of Diet in Renal Disease Study Equation for Estimating Glomerular Filtration Rate," Ann Intern Med. 145(4):247-254 (2006).
Lewin et al., "Tat peptide-derivatized magnetic nanoparticles allow in vivo tracking and recovery of progenitor cells," Nat Biotechnol. 18(4):410-4 (2000).
Li et al., "Rapid Identification of Yeasts Commonly Found in Positive Blood Cultures by Amplification of the Internal Transcribed Spacer Regions 1 and 2," Eur J Clin Microbiol Infect Dis. 22(11):693-696 (2003).
Liao et al., "High-Throughput Miniaturized Immunoassay for Human Interleukin-6 Using Electrochemical Sandwich-Type Enzyme Immunosensors," Curr Pharm Analysis 5(2):164-170 (2009).
Ling et al., "Magnetic Relaxation-Based Platform for Multiplexed Assays," Analyst 135(9):2360-2364 (2010).
Liu et al., "Rapid Distribution of a Liquid Column Into a Matrix of Nanoliter Wells for Parallel Real-Time Quantitative PCR," Sens Actuators B Chem. 135(2):671-677 (2009).
Liu, Yong, thesis: "CMOS Magnetic Cell Manipulator and CMOS NMR Biomolecular Sensor," Doctor of Philosophy, School of Engineering and Applied Sciences, Harvard University, 2007 (166 pages).

(56) References Cited

OTHER PUBLICATIONS

Lowery et al., Application of Magnetics in Point-of-Care Testing. Point-of-Care Testing: Needs, Opportunity and Innovation 3rd Edition, AACC Press (2010) (11 pages).
Lowery, Nanomaterials-Based Magnetic Relaxation Biosensors. *Nanomaterials for the Life Sciences vol. 4: Magnetic Nanomaterials*. Challa S. S. R. Kumar, 3-53 (2009).
Lück et al., "Analysis of Plasma Protein Adsorption on Polymeric Nanoparticles with Different Surface Characteristics," J Biomed Mater Res. 39(3):478-485 (1998).
Lundqvist et al., "Nanoparticle Size and Surface Properties Determine the Protein Corona with Possible Implications for Biological Impacts," Proc Natl Acad Sci U S A. 105(38):14265-14270 (2008).
Lustgarten et al., "Simple, Rapid, Kinetic Method for Serum Creatinine Measurement," Clin. Chem. 18(11):1419-1422 (1972).
Ma et al., "Rapid and Sensitive Detection of Microcystin by Immunosensor Based on Nuclear Magnetic Resonance," Biosens Bioelectron. 25(1):240-243 (2009).
Maaroufi et al., "Early Detection and Identification of Commonly Encountered Candida Species from Simulated Blood Cultures by Using a Real-Time PCR-Based Assay," J. Mol. Diagn. 6(2):108-114 (2004).
Magin et al., "Miniature Magnetic Resonance Machines," IEEE Spectrum 34(10):51-61 (1997).
Mäkiranta et al., "Modeling and Simulation of Magnetic Nanoparticle Sensor" Proceedings of the 2005 IEEE, Engineering in Medicine and Biology 27th Annual Conference, Sep. 1-4, Shanghai, China. 1256-1259 (2005).
Malba et al., "Laser-Lathe Lithography—A Novel Method for Manufacturing Nuclear Magnetic Resonance Microcoils," Biomed. Microdevices 5(1):21-27 (2003).
Martin et al., "Strong Intrinsic Mixing in Vortex Magnetic Fields," Phys Rev E Stat Nonlin Soft Matter Phys. 80(1 Pt 2):016312 (2009) (6 pages).
Martin et al., "The Epidemiology of Sepsis in the United States from 1979 Through 2000," N Engl J Med. 348(16):1546-1554 (2003).
Martin et al., "Development of a PCR-based line probe assay for identification of fungal pathogens," J Clin Microbiol. 38(10):3735-3742 (2000).
Martin, "Theory of Strong Intrinsic Mixing of Particle Suspensions in Vortex Magnetic Fields," Phys Rev E Stat Nonlin Soft Matter Phys. 79(1 Pt 1):011503 (2009) (12 pages).
Massin et al., "Planar Microcoil-based Magnetic Resonance Imaging of Cells" Transducers, Solid-state Sensors, Actuators and Microsystems 12th International Conference, Jun. 8-12, Boston, MA. 2:967-970 (2003).
Massin et al., "Planar Microcoil-Based Microfluidic NMR Probes," J Magn Reson. 164(2):242-255 (2003).
Masson et al., "Combined Enzymic-Jaffe Method for Determination of Creatinine in Serum," Clin Chem. 27(1):18-21 (1981).
McCusker et al., "Improved Method for Direct PCR Amplification from Whole Blood," Nucleic Acids Res. 20(24):6747 (1992) (1 page).
McDowell et al., "Operating Nanoliter Scale NMR Microcoils in a 1 Tesla Field," J Magn Reson. 188(1):74-82 (2007).
Mercier et al., "Direct PCR from Whole Blood, Without DNA Extraction," Nucleic Acids Res. 18(19):5908 (1990).
Metwally et al., "Improving Molecular Detection of Candida DNA in Whole Blood: Comparison of Seven Fungal DNA Extraction Protocols Using Real-Time PCR," J Med Microbiol. 57(Pt 3):296-303 (2008).
Morrell et al., "Delaying the Empiric Treatment of Candida Bloodstream Infection Until Positive Blood Culture Results are Obtained: A Potential Risk Factor for Hospital Mortality," Antimicrob. Agents Chemother. 49(9):3640-3645 (2005).
Moser et al., "On-Chip Immuno-Agglutination Assay with Analyte Capture by Dynamic Manipulation of Superparamagnetic Beads," Lab Chip. 9(22):3261-3267 (2009).

Niemeyer et al., "Self-Assembly of DNA-streptavidin Nanostructures and Their Use as Reagents in Immuno-PCR" Nucleic Acids Res. 27(23):4553-4561 (1999).
Panaccio et al., "FoLT PCR: A Simple PCR Protocol for Amplifying DNA Directly from Whole Blood," Biotechniques 14(2):238-240, 242, 243 (1993).
Pappas et al., "Cellular Separations: a Review of New Challenges in Analytical Chemistry," Anal Chim. Acta. 601(1):26-35 (2007).
Park et al., "Determination of Nanoparticle Vehicle Unpackaging by MR Imaging of a T(2) Magnetic Relaxation Switch," Biomaterials 29(6):724-732 (2008).
Peake et al., "Measurement of Serum Creatinine—Current Status and Future Goals," Clin Biochem Rev. 27(4):173-184 (2006).
Peck et al., "RF Microcoils Patterned Using Microlithographic Techniques for Use as Microsensors in NMR," Engineering in Medicine and Biology Society, Proceedings of the 15th annual international conference of the IEEE, pp. 174-175 (1993).
Perez et al., "DNA-based Magnetic Nanoparticle Assembly Acts as a Magnetic Relaxation Nanoswitch Allowing Screening of DNA-cleaving Agents," J. Am. Chem. Soc. 124(12):2856-2857 (2002).
Perez et al., "Integrated Nanosensors to Determine Levels and Functional Activity of Human Telomerase," Neoplasia 10(10):1066-1072 (2008).
Perez et al., "Peroxidase Substrate Nanosensors for MR Imaging", Nano Lett. 4(1):119-122 (2004).
Perez et al., "Magnetic Relaxation Switches Capable of Sensing Molecular Interactions," Nat Biotechnol. 20(8):816-820 (2002).
Perez et al., "Use of Magnetic Nanoparticles as Nanosensors to Probe for Molecular Interactions," Chembiochem. 5(3):261-264 (2004).
Perez et al., "Viral-Induced Self-Assembly of Magnetic Nanoparticles Allows the Detection of Viral Particles in Biological Media," J Am Chem Soc. 125(34):10192-10193 (2003).
Pryce et al., "Real-Time Automated Polymerase Chain Reaction (PCR) to Detect Candida Albicans and Aspergillus Fumigatus DNA in Whole Blood from High-Risk Patients," Diagn Microbiol Infect Dis. 47(3):487-496 (2003).
Ramadan et al., "On-Chip Micro-electromagnets for Magnetic-based Bio-molecules Separation," J Magn Magn Mater. 281(2-3):150-172 (2004).
Renaud et al., "Implantable Planar rf Microcoils for NMR Microspectroscopy," Sens Actuators A Phys. 99(3):244-248 (2002).
Rida et al., "Long-Range Transport of Magnetic Microbeads Using Simple Planar Coils Placed in a Uniform Magnetostatic Field," Appl. Phys. Lett. 83(12):2396-2398 (2003).
Rosenstraus et al., "An Internal Control for Routine Diagnostic PCR: Design, Properties, and Effect on Clinical Performance," J. Clin. Microbiol. 36(1):191-197 (1998).
Routley et al., "The HALO System—A Light Weight Portable Imaging System," Magn Reson Imaging. 22(8):1145-1151 (2004).
Ruttimann et al., "DNA Polymerases from the Extremely Thermophilic Bacterium Thermus Thermophilus HB-8," Eur J Biochem. 149(1):41-46 (1985).
Seeber et al., "Triaxial Magnetic Field Gradient System for Microcoil Magnetic Resonance Imaging," Rev. Sci. Instrum. 71(11):4263-4272 (2000).
Shapiro et al., "Dynamic Imaging with MRI Contrast Agents: Quantitative Considerations," Magn Reson Imaging. 24(4):449-462 (2006).
Siegel et al., "Affinity Maturation of Tacrolimus Antibody for Improved Immunoassay Performance," Clin Chem. 54(6):1008-1017 (2008).
Sillerud et al., "1H NMR Detection of Superparamagnetic Nanoparticles at 1T Using a Microcoil and Novel Tuning Circuit," J Magn Reson. 181(2):181-190 (2006).
Skurup et al., "New Creatinine Sensor for Point-of-Care Testing of Creatinine Meets the National Kidney Disease Education Program Guidelines," Clin Chem Lab Med. 46(1):3-8 (2008).
Stöcklein et al., "Enzyme Kinetic Assays with Surface Plasmon Resonance (BIAcore) Based on Competition Between Enzyme and Creatinine Antibody," Biosens Bioelectron. 15(7-8):377-382 (2000).
Sullivan et al., "A Highly Specific Test for Creatinine," J Biol Chem. 233(2):530-534 (1958).

(56) References Cited

OTHER PUBLICATIONS

Sun et al., "Experimental Study on T2 Relaxation Time of Protons in Water Suspensions of Iron-oxide Nanoparticles: Waiting Time Dependence," J Magn Magn Mater. 321(18):2971-2975 (2009).
Syms et al., "MEMS Helmholtz Coils for Magnetic Resonance Imaging," J Micromech Microeng. 15(7): S1-S9 (2005) (10 pages).
Taktak et al., "Electrode Chemistry Yields a Nanoparticle-based NMR Sensor for Calcium," Langmuir 24(14): 7596-7598 (2008).
Taktak et al., "Multiparameter Magnetic Relaxation Switch Assays," Anal Chem. 79(23):8863-8869 (2007).
Tanaka et al., "Properties of Superparamagnetic Iron Oxide Nanoparticles Assembled on Nucleic Acids," Nucleic Acids Symp Ser (Oxf). (52):693-694 (2008).
Taur et al., "Effect of Antifungal Therapy Timing on Mortality in Cancer Patients with Candidemia," Antimicrob Agents Chemother. 54(1):184-190 (2010).
Thorne et al., "Analytic Validation of a Quantitative Real-Time PCR Assay to Measure CMV Viral Load in Whole Blood," Diagn Mol Pathol. 16(2):73-80 (2007).
Tong et al., "Coating Optimization of Superparamagnetic Iron Oxide Nanoparticles for High T2 Relaxivity," Nano Lett. 10(11):4607-4613 (2010).
Tsourkas et al., "Magnetic Relaxation Switch Immunosensors Detect Enantiomeric Impurities," Angew. Chem. Int. Ed. Engl. 43(18):2395-2399 (2004).
Ulvik et al., "Single Nucleotide Polymorphism (SNP) Genotyping in Unprocessed Whole Blood and Serum by Real-Time PCR: Application to SNPs Affecting Homocysteine and Folate Metabolism," Clin Chem. 47(11):2050-2053 (2001).
van Bentum et al., "Towards Nuclear Magnetic Resonance microspectroscopy and micro-imaging," Analyst. 129(9):793-803 (2004).
Vasseur et al., "Inter-area and Inter-AS MPLS Traffic Engineering," IETF Internet draft (2004) (33 pages).
Vollenhofer-Schrumpf et al., "A simple nucleic acid hybridization/latex agglutination assay for the rapid detection of polymerase chain reaction amplicons," J Microbiol Methods. 68(3):568-576 (2007).
Von Lilienfeld-Toal et al., "Utility of a Commercially Available Multiplex Real-Time PCR Assay to Detect Bacterial and Fungal Pathogens in Febrile Neutropenia," J Clin Microbiol. 47(8):2405-2410 (2009).
Wallemacq et al., "Improvement and Assessment of Enzyme-Linked Immunosorbent Assay to Detect Low FK506 Concentrations in Plasma or Whole Blood Within 6 Hours," Clin Chem. 39(6):1045-1049 (1993).
Wang et al., "A Novel Strategy to Engineer DNA Polymerases for Enhanced Processivity and Improved Performance in vitro," Nucleic Acids Res. 32(3):1197-1207 (2004).
Weetall et al., "Antibodies Immobilized on Inorganic Supports," Appl Biochem Biotechnol. 22(3):311-330 (1989).
Weetall, "Preparation of Immobilized Proteins Covalently Coupled Through Silane Coupling Agents to Inorganic Supports," Appl Biochem Biotechnol. 41(3):157-188 (1993).
Weissleder et al., "Cell-Specific Targeting of Nanoparticles by Multivalent Attachment of Small Molecules," Nat Biotechnol. 23(11):1418-1423 (2005).
Wensink et al., "High Signal to Noise Ratio in Low Field NMR on chip, Simulations and Experimental Results" Micro Electro Mechanical Systems 17th IEEE International Conference, Netherlands, pp. 407-410 (2004).
Wildgruber et al., "Monocyte Subset Dynamics in Human Atherosclerosis can be Profiled with Magnetic Nano-Sensors" PLoS One. 4(5):e5663 (2009) (9 pages).
Wilson et al., "Creatine and Creatinine in Whole Blood and Plasma," J Biol Chem. 29:413-423 (1917).
Wu et al., "1H-NMR Spectroscopy on the Nanoliter Scale for Static and On-Line Measurements," Anal. Chem. 66(22):3849-3857 (1994).
Xing et al., "Immobilization of Biomolecules on the Surface of Inorganic Nanoparticles for Biomedical Applications," Sci. Technol. Adv. Mater. 11(1): 014101 (2010) (17 pages).

Yigit et al., "Smart "Turn-On" Magnetic Resonance Contrast Agents Based on Aptamer-Functionalized Superparamagnetic Iron Oxide Nanoparticles," Chembiochem. 8(14):1675-1678 (2007).
Zhang et al., "A Probe Design for the Acquisition of Homonuclear, Heteronuclear, and Inverse Detected NMR Spectra from Multiple Samples," J Magn Reson. 153(2):254-258 (2001).
Zhao et al., "Magnetic Sensors for Protease Assays," Angew. Chem. Int. Ed. Engl. 42(12):1375-1378 (2003).
International Search Report and Written Opinion of the International Searching Authority for International Application No. PCT/US11/56933, dated May 10, 2012 (23 pages).
International Search Report and Written Opinion of the International Searching Authority for International Application No. PCT/US11/56936, dated May 17, 2012 (15 pages).
International Search Report for International Application No. PCT/IB2008/052597, dated Nov. 11, 2008 (1 page).
International Search Report for International Application No. PCT/US2008/073346, dated Nov. 7, 2008 (1 page).
Office Action for U.S. Appl. No. 13/363,916, dated Aug. 2, 2012 (64 pages).
Office Action for U.S. Appl. No. 13/402,566, dated Oct. 29, 2012 (60 pages).
Office Action for U.S. Appl. No. 13/646,402, dated Mar. 14, 2013 (53 pages).
Office Action for U.S. Appl. No. 13/402,566, dated Jan. 22, 2013 (27 pages).
Office Action for U.S. Appl. No. 13/649,839, dated Mar. 14, 2013 (48 pages).
Ferrer et al., "Detection and identification of fungal pathogens by PCR and by ITS2 and 5.8S ribosomal DNA typing in ocular infections," J Clin Microbiol. 39(8):2873-2879 (2001).
Fredricks et al., "Comparison of six DNA extraction methods for recovery of fungal DNA as assessed by quantitative PCR," J Clin Microbiol. 43(10):5122-5128 (2005).
International Preliminary Report on Patentability for International Patent Application No. PCT/US2011/056933, dated Apr. 23, 2013 (16 pages).
Office Action for U.S. Appl. No. 13/402,566, dated May 30, 2013 (33 pages).
International Preliminary Report on Patentability for International Patent Application No. PCT/US2011/056936, dated Jun. 18, 2013 (11 pages).
Office Action for U.S. Appl. No. 29/390,300, dated Jun. 27, 2012 (32 pages).
Office Action for Canadian Patent Application No. 142812, dated Aug. 27, 2012 (3 pages).
International Search Report and Written Opinion of the International Searching Authority for International Patent Application No. PCT/US13/31774, dated Jul. 25, 2013 (9 pages).
Liu et al., "Self-contained, fully integrated biochip for sample preparation, polymerase chain reaction amplification, and DNA microarray detection," Anal Chem. 76(7):1824-1831 (2004).
Extended European Search Report for European Application No. 11835088.3, dated Mar. 19, 2014 (11 pages).
Tsukamoto et al., "Development of a Squid system using field reversal for rapidly detecting bacteria," IEEE Transactions on Applied Superconductivity. 19(3):853-856 (2009).
International Preliminary Report on Patentability and Written Opinion for International Patent Application No. PCT/US2013/031774, dated Oct. 21, 2014 (6 pages).
Office Action for Chinese Application No. 201180061890.1, dated Nov. 4, 2014 (20 pages).
Examination Report for Australian Application No. 2011317073, dated Jun. 16, 2014 (4 pages).
Lott et al., "Sequence analysis of the internal transcribed spacer 2 (ITS2) from yeast species within the genus *Candida*," Curr Microbiol. 36(2):63-9 (1998).
Goel et al., "Molecular beacon: a multitask probe," J Appl Microbiol. 99(3):435-42 (2005).
Khlif et al., "Detection and identification of *Candida* sp. by PCR in candidemia diagnosis," J Mycol Med. 17(4): 256-260 (2007).
Notice of Reasons for Rejection for Japanese Patent Application No. 2013-535053, dated Sep. 2, 2015 (6 pages).

(56) References Cited

OTHER PUBLICATIONS

Morgenthaler et al., "Sensitive immunoluminometric assay for the detection of procalcitonin," Clin Chem. 48(5):788-90 (2002).
Ito et al., "Treatment of Candida infections with amphotericin B lipid complex," Clin Infect Dis. 40 Suppl 6:S384-91 (2005).
Cleary et al., "Amphotericin B enzyme-linked immunosorbent assay," Antimicrob Agents Chemother. 40(3):637-41 (1996).
Emery, "Investigation of CMV disease in immunocompromised patients," J Clin Pathol. 54(2):84-8 (2001).
Naber, "*Staphylococcus aureus* bacteremia: epidemiology, pathophysiology, and management strategies," Clin Infect Dis. 48 (Suppl 4):S231-7 (2009).
Partial European Search Report for European Application No. 15002772.0, dated Nov. 4, 2015 (7 pages).
Extended European Search Report for European Application No. 15002772.0, dated Feb. 22, 2016 (12 pages).
Partial Supplementary European Search Report for European Application No. 13779063.0, dated Feb. 17, 2016 (8 pages).
Extended European Search Report for European Patent Application No. 13779063.0, dated Jun. 7, 2016 (17 pages).
International Preliminary Report on Patentability for International Application No. PCT/US2015/060340, dated May 16, 2017 (10 pages).
Extended European Search Report for European Application No. 17205422.3, dated Jan. 22, 2018 (10 pages).
Josephson et al., "High-efficiency intracellular magnetic labeling with novel superparamagnetic-Tat peptide conjugates," Bioconjug Chem. 10(2):186-91 (1999).
Leal-Klevezas et al., "Single-step PCR for detection of *Brucella* spp. from blood and milk of infected animals," J Clin Microbiol. 33(12):3087-90 (1995).
Lewin et al., "A simple method for DNA extraction from leukocytes for use in PCR," Biotechniques. 13(4):522-3 (1992) (4 pages).
Mäkiranta et al., "Modeling and simulation of magnetic nanoparticle sensor," Proceedings of the 2005 IEEE, Engineering in Medicine and Biology 27th Annual Conference, Shanghai, China, Sep. 1-4,1256-59 (2005).
Neely et al., "T2 magnetic resonance enables nanoparticle-mediated rapid detection of candidemia in whole blood," Sci Transl Med. 5(182):182ra54 (includes supplemental information) (2013) (10 pages).
Matsuda et al., "Sensitive quantitative detection of commensal bacteria by rRNA-targeted reverse transcription-PCR," Appl Environ Microbiol. 73(1):32-9 (includes supplemental information) (2007) (9 pages).
Chang et al., "Rapid identification of yeasts in positive blood cultures by a multiplex PCR method," J Clin Microbiol. 39(10):3466-71 (2001).
Office Action for Canadian Patent Application No. 2,815,085, dated Aug. 7, 2019 (6 pages).
Office Action for U.S. Appl. No. 15/990,400, dated Oct. 3, 2019 (257 pages).
Nguyen et al., "Performance of the T2Bacteria Panel for Diagnosing Bloodstream Infections: A Diagnostic Accuracy Study," Ann Intern Med. 170(12):845-852 (2019) (11 pages).
Examination Report for Australian Application No. 2018204483, dated Nov. 12, 2019 (3 pages).
Summons to attend oral proceedings pursuant to Rule 115(1) EPC for European Patent Application No. 17205422.3, dated Nov. 13, 2019 (5 pages).

* cited by examiner

FIB. 4B

FIG. 6 (cont.)

SEQ ID NO: 52

```
                          SEQUENCE LISTING

<160> NUMBER OF SEQ ID NOS: 52

<210> SEQ ID NO 1
<211> LENGTH: 31
<212> TYPE: DNA
<213> ORGANISM: Candida albicans

<400> SEQUENCE: 1
ggtcaaagtt tgaagatata cgtggttgac c                                   31

<210> SEQ ID NO 2
<211> LENGTH: 29
<212> TYPE: DNA
<213> ORGANISM: Candida tropicalis

<400> SEQUENCE: 2
ctagcaaaat aagcgttttt ggatgctag                                      29

<210> SEQ ID NO 3
<211> LENGTH: 30
<212> TYPE: DNA
<213> ORGANISM: Candida glabrata

<400> SEQUENCE: 3
cagcacgcac aaaacactca cttattgctg                                     30

<210> SEQ ID NO 4
<211> LENGTH: 30
<212> TYPE: DNA
<213> ORGANISM: Candida parapsilosis

<400> SEQUENCE: 4
gtcgaatttg gaagaagttt tggtttcgac                                     30

<210> SEQ ID NO 5
<211> LENGTH: 31
<212> TYPE: DNA
<213> ORGANISM: Candida krusei

<400> SEQUENCE: 5
```

-continued cctgatttga ggtcgagctt tttgtatcag g                                           31

<210> SEQ ID NO 6
<211> LENGTH: 25
<212> TYPE: DNA
<213> ORGANISM: Candida albicans

<400> SEQUENCE: 6
ggtcaaagtt tgaagatata cgtgg                                                  25

<210> SEQ ID NO 7
<211> LENGTH: 23
<212> TYPE: DNA
<213> ORGANISM: Candida tropicalis

<400> SEQUENCE: 7
ctagcaaaat aagcgttttt gga                                                    23

<210> SEQ ID NO 8
<211> LENGTH: 25
<212> TYPE: DNA
<213> ORGANISM: Candida glabrata

<400> SEQUENCE: 8
cagcacgcac aaaacactca cttat                                                  25

<210> SEQ ID NO 9
<211> LENGTH: 24
<212> TYPE: DNA
<213> ORGANISM: Candida parapsilosis

<400> SEQUENCE: 9
gtcgaatttg gaagaagttt tggt                                                   24

<210> SEQ ID NO 10
<211> LENGTH: 25
<212> TYPE: DNA
<213> ORGANISM: Candida krusei

<400> SEQUENCE: 10
cctgatttga ggtcgagctt tttgt                                                  25

<210> SEQ ID NO 11
<211> LENGTH: 20
<212> TYPE: DNA
<213> ORGANISM: Candida

<400> SEQUENCE: 11
ggcatgcctg tttgagcgtc                                                        20

<210> SEQ ID NO 12
<211> LENGTH: 29
<212> TYPE: DNA
<213> ORGANISM: Candida

<400> SEQUENCE: 12
gcttattgat atgcttaagt tcagcgggt                                              29

<210> SEQ ID NO 13
<211> LENGTH: 23
<212> TYPE: DNA
<213> ORGANISM: Candida  albicans

<400> SEQUENCE: 13
acccagcggt ttgagggaga aac                                           23

<210> SEQ ID NO 14
<211> LENGTH: 30
<212> TYPE: DNA
<213> ORGANISM: Candida albicans

<400> SEQUENCE: 14
aaagtttgaa gatatacgtg gtggacgtta                                    30

<210> SEQ ID NO 15
<211> LENGTH: 21
<212> TYPE: DNA
<213> ORGANISM: Candida krusei

<400> SEQUENCE: 15
cgcacgcgca agatggaaac g                                             21

<210> SEQ ID NO 16
<211> LENGTH: 23
<212> TYPE: DNA
<213> ORGANISM: Candida krusei

<400> SEQUENCE: 16
aagttcagcg ggtattccta cct                                           23

<210> SEQ ID NO 17
<211> LENGTH: 27
<212> TYPE: DNA
<213> ORGANISM: Candida krusei

<400> SEQUENCE: 17 agcttttgt tgtctcgcaa cactcgc                                        27

<210> SEQ ID NO 18
<211> LENGTH: 26
<212> TYPE: DNA
<213> ORGANISM: Candida glabrata

<400> SEQUENCE: 18
ctaccaaaca caatgtgttt gagaag                                        26

<210> SEQ ID NO 19
<211> LENGTH: 31
<212> TYPE: DNA
<213> ORGANISM: Candida glabrata

<400> SEQUENCE: 19
cctgatttga ggtcaaactt aaagacgtct g                                  31

<210> SEQ ID NO 20
<211> LENGTH: 24
<212> TYPE: DNA
<213> ORGANISM: Candida
<220> FEATURE:
<221> NAME/KEY: misc_feature
<222> LOCATION: (22)..(22)
<223> OTHER INFORMATION: n is 5'5-Nitroindole

<400> SEQUENCE: 20
agtcctacct gatttgaggt cnaa                                          24

```
<210> SEQ ID NO 21
<211> LENGTH: 21
<212> TYPE: DNA
<213> ORGANISM: Candida
<220> FEATURE:
<221> NAME/KEY: misc_feature
<222> LOCATION: (4)..(4)
<223> OTHER INFORMATION: n is 5'5-Nitroindole

<400> SEQUENCE: 21
ccgngggttt gagggagaaa t                                               21

<210> SEQ ID NO 22
<211> LENGTH: 33
<212> TYPE: DNA
<213> ORGANISM: Candida

<400> SEQUENCE: 22
aaagttatga ataaattgt ggtggccact agc                                   33

<210> SEQ ID NO 23
<211> LENGTH: 22
<212> TYPE: DNA
<213> ORGANISM: Candida

<400> SEQUENCE: 23 acccggggt ttgagggaga aa                                               22

<210> SEQ ID NO 24
<211> LENGTH: 24
<212> TYPE: DNA
<213> ORGANISM: Candida

<400> SEQUENCE: 24
agtcctacct gatttgaggt cgaa                                            24

<210> SEQ ID NO 25
<211> LENGTH: 21
<212> TYPE: DNA
<213> ORGANISM: Candida

<400> SEQUENCE: 25
ccgagggttt gagggagaaa t                                               21

<210> SEQ ID NO 26
<211> LENGTH: 30
<212> TYPE: DNA
<213> ORGANISM: Candida dubliniensis

<400> SEQUENCE: 26
aataaaatgg gcgacgccag agaccgcctt                                      30

<210> SEQ ID NO 27
<211> LENGTH: 25
<212> TYPE: DNA
<213> ORGANISM: Candida  dubliniensis

<400> SEQUENCE: 27
gcatctccgc cttataccac tatca                                           25

<210> SEQ ID NO 28
<211> LENGTH: 23
<212> TYPE: DNA
<213> ORGANISM: Candida lusitaniae
```

```
<400> SEQUENCE: 28
ggttgatatt tcggagcaac gcc                                              23

<210> SEQ ID NO 29
<211> LENGTH: 25
<212> TYPE: DNA
<213> ORGANISM: Candida lusitaniae

<400> SEQUENCE: 29
gtcctacctg atttgagggc gaaat                                            25

<210> SEQ ID NO 30
<211> LENGTH: 38
<212> TYPE: DNA
<213> ORGANISM: Candida guillermondi

<400> SEQUENCE: 30
gcaaacgcct agtccgacta agagtatcac tcaatacc                              38

<210> SEQ ID NO 31
<211> LENGTH: 36
<212> TYPE: DNA
<213> ORGANISM: Candida guillermondi

<400> SEQUENCE: 31
tgtaaggccg ggccaacaat accagaaata tcccgc                                36

<210> SEQ ID NO 32
<211> LENGTH: 21
<212> TYPE: DNA
<213> ORGANISM: Candida krusei

<400> SEQUENCE: 32
ccgagagcga gtgttgcgag a                                                21

<210> SEQ ID NO 33
<211> LENGTH: 21
<212> TYPE: DNA
<213> ORGANISM: Candida krusei

<400> SEQUENCE: 33
tctcgcaaca ctcgctctcg g                                                21

<210> SEQ ID NO 34
<211> LENGTH: 23
<212> TYPE: DNA
<213> ORGANISM: Candida albicans

<400> SEQUENCE: 34
ggtaacgtcc accacgtata tct                                              23

<210> SEQ ID NO 35
<211> LENGTH: 23
<212> TYPE: DNA
<213> ORGANISM: Candida albicans

<400> SEQUENCE: 35
agatatacgt ggtggacgtt acc                                              23

<210> SEQ ID NO 36
<211> LENGTH: 28
<212> TYPE: DNA
<213> ORGANISM: Candida glabrata
```

```
<400> SEQUENCE: 36
gggagggata agtgagtgtt ttgtgcgt                                          28

<210> SEQ ID NO 37
<211> LENGTH: 28
<212> TYPE: DNA
<213> ORGANISM: Candida glabrata

<400> SEQUENCE: 37
acgcacaaaa cactcactta tccctccc                                          28

<210> SEQ ID NO 38
<211> LENGTH: 24
<212> TYPE: DNA
<213> ORGANISM: Candida parapsilosis

<400> SEQUENCE: 38
ggtacaaact ccaaaacttc ttcc                                              24

<210> SEQ ID NO 39
<211> LENGTH: 24
<212> TYPE: DNA
<213> ORGANISM: Candida parapsilosis

<400> SEQUENCE: 39
ggaagaagtt ttggagtttg tacc                                              24

<210> SEQ ID NO 40
<211> LENGTH: 26
<212> TYPE: DNA
<213> ORGANISM: Candida tropicalis

<400> SEQUENCE: 40
gctagtggcc accacaattt atttca                                            26

<210> SEQ ID NO 41
<211> LENGTH: 26
<212> TYPE: DNA
<213> ORGANISM: Candida tropicalis

<400> SEQUENCE: 41
tgaaataaat tgtggtggcc actagc                                            26

<210> SEQ ID NO 42
<211> LENGTH: 237
<212> TYPE: DNA
<213> ORGANISM: Candida

<400> SEQUENCE: 42
ggcatgcctg tttgagcgtc gtttccatct tgcgcgtgcg cagagttggg ggagcggagc       60
ggacgacgtg taaagagcgt cggagctgcg actcgcctga aagggagcga agctggccga     120
gcgaactaga cttttttttca gggacgcttg gcggccgaga gcgagtgttg cgagacaaca    180
aaaagctcga cctcaaatca ggtggaatac ccgctgaact taagcatatc aataagc        237

<210> SEQ ID NO 43
<211> LENGTH: 228
<212> TYPE: DNA
<213> ORGANISM: Candida

<400> SEQUENCE: 43
```

```
ggcatgcctg tttgagcgtc gtttctccct caaaccgctg ggtttggtgt tgagcaatac    60
gacttgggtt tgcttgaaag acggtagtgg taaggcggga tcgctttgac aatggcttag   120
gtctaaccaa aaacattgct tgcggcggta acgtccacca cgtatatctt caaactttga   180
cctcaaatca ggtggactac ccgctgaact taagcatatc aataagcg               228

<210> SEQ ID NO 44
<211> LENGTH: 306
<212> TYPE: DNA
<213> ORGANISM: Candida

<400> SEQUENCE: 44
ggcatgcctg tttgagcgtc atttccttct caaacacatt gtgtttggta gtgagtgata    60 ctcgttttg agttaacttg aaattgtagg ccatatcagt atgtgggaca cgagcgcaag   120
cttctctatt aatctgctgc tcgtttgcgc gagcggcggg ggttaatact gtattaggtt   180
ttaccaactc ggtgttgatc tagggaggga taagtgagtg ttttgtgcgt gctgggcaga   240
cagacgtctt taagtttgac ctcaaatcag gtgggttacc cgctgaactt aagcatatca   300
ataagc                                                              306

<210> SEQ ID NO 45
<211> LENGTH: 200
<212> TYPE: DNA
<213> ORGANISM: Candida

<400> SEQUENCE: 45
ggcatgcctg tttgagcgtc atttccttct caaaccctcg ggtttggtgt tgagcgatac    60
gctgggtttg cttgaaagaa aggcggagta taaactaatg gataggtttt ttccactcat   120
tggtacaaac tccaaaactt cttccaaatt cgacctcaaa tcaggtggac tacccgctga   180
acttaagcat atcaataagc                                               200

<210> SEQ ID NO 46
<211> LENGTH: 217
<212> TYPE: DNA
<213> ORGANISM: Candida

<400> SEQUENCE: 46
ggcatgcctg tttgagcgtc atttctccct caaaccccccg ggtttggtgt tgagcaatac    60
gctaggtttg tttgaaagaa tttaacgtgg aaacttattt taagcgactt aggtttatcc   120
aaaaacgctt atttttgctag tggccaccac aatttatttc ataactttga cctcaaatca   180
ggtggactac ccgctgaact taagcatatc aataagc                            217

<210> SEQ ID NO 47
<211> LENGTH: 200
<212> TYPE: DNA
<213> ORGANISM: Candida

<400> SEQUENCE: 47
ggcatgcctg tttgagcgtc atttctccct caaaccctcg ggtttggtgt tgagcgatac    60
gctgggtttg cttgaaagaa aggcggagta taaactaatg gataggtttt ttccactcat   120
tggtacaaac tccaaaactt cttccaaatt cgacctcaaa tcaggtggac tacccgctga   180
acttaagcat atcaataagc                                               200

<210> SEQ ID NO 48
<211> LENGTH: 215
```

<212> TYPE: DNA
<213> ORGANISM: Candida

<400> SEQUENCE: 48

```
ggcatgcctg tttgagcgtc atttctccct caaaccccg ggtttggtgt tgagcaatac      60
gctaggtttg tttgaagaat ttaacgtgga aacttatttt aagcgactta ggtttatcca     120
aaaacgctta ttttgctagt ggcaccacaa tttatttcat aactttcacc tcaaatcagg    180
tccactaccc gctgaactta agcatatcaa taagc                                215
```

<210> SEQ ID NO 49
<211> LENGTH: 153
<212> TYPE: DNA
<213> ORGANISM: Candida

<400> SEQUENCE: 49

```
ggcatgcctg tttgagcgtc atttgcatcc cctctaaccc ccggttaggc gttgctccga     60
aatatcaacc gcgctgtcaa acacgtttac agcacgacat ttcgccctca aatcaggtgg    120
actacccgct gaacttaagc atatcaataa gcg                                  153
```

<210> SEQ ID NO 50
<211> LENGTH: 256
<212> TYPE: DNA
<213> ORGANISM: Candida

<400> SEQUENCE: 50

```
ggcatgcctg tttgagcgtc atttctctct caaaccccg ggtttggtat tgagtgatac      60
tcttagtcgg actaggcgtt tgcttgaagg gcatggcatg ggtagtactg gatagtgctg    120
tcgacctctc aatgtattag gtttatccaa ctcgttgaat ggtgtggcgg gatatttctt    180
ggtattgttg gcccggcctt acaacaacca aacaagtttg acctcaaatc aggtggaata    240
cccgctgaac ttaagc                                                     256
```

<210> SEQ ID NO 51
<211> LENGTH: 222
<212> TYPE: DNA
<213> ORGANISM: Candida
<220> FEATURE:
<221> NAME/KEY: misc_feature
<222> LOCATION: (71)..(71)
<223> OTHER INFORMATION: n is a, c, g, or t
<220> FEATURE:
<221> NAME/KEY: misc_feature
<222> LOCATION: (82)..(82)
<223> OTHER INFORMATION: n is a, c, g, or t
<220> FEATURE:
<221> NAME/KEY: misc_feature
<222> LOCATION: (87)..(88)
<223> OTHER INFORMATION: n is a, c, g, or t
<220> FEATURE:
<221> NAME/KEY: misc_feature
<222> LOCATION: (92)..(92)
<223> OTHER INFORMATION: n is a, c, g, or t
<220> FEATURE:
<221> NAME/KEY: misc_feature
<222> LOCATION: (107)..(107)
<223> OTHER INFORMATION: n is a, c, g, or t
<220> FEATURE:
<221> NAME/KEY: misc_feature
<222> LOCATION: (111)..(111)
<223> OTHER INFORMATION: n is a, c, g, or t
<220> FEATURE:
<221> NAME/KEY: misc_feature
<222> LOCATION: (114)..(114)
<223> OTHER INFORMATION: n is a, c, g, or t
<220> FEATURE:

```
<221> NAME/KEY: misc_feature
<222> LOCATION: (116)..(116)
<223> OTHER INFORMATION: n is a, c, g, or t
<220> FEATURE:
<221> NAME/KEY: misc_feature
<222> LOCATION: (118)..(118)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: misc_feature
<222> LOCATION: (144)..(144)
<223> OTHER INFORMATION: n is a, c, g, or t
<220> FEATURE:
<221> NAME/KEY: misc_feature
<222> LOCATION: (147)..(148)
<223> OTHER INFORMATION: n is a, c, g, or t
<220> FEATURE:
<221> NAME/KEY: misc_feature
<222> LOCATION: (150)..(152)
<223> OTHER INFORMATION: n is a, c, g, or t
<220> FEATURE:
<221> NAME/KEY: misc_feature
<222> LOCATION: (158)..(158)
<223> OTHER INFORMATION: n is a, c, g, or t
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (221)..(222)
<223> OTHER INFORMATION: n is a, c, g, or t

<400> SEQUENCE: 51
ggcatgcctg tttgagcgtc atttctccct caaaccccg ggtttggtgt tgagcgatac     60
cctgggtttg nttgaagagc gnagcgnnga gncggactat aagctantgg nttngntnta   120
tccacacatt gctaganacg ctancgnncn nnacaaanta cttcaaantt tgacctcaaa   180
tcaggtggac tacccgctga acttaagcat atcaataagc nn                      222

<210> SEQ ID NO 52
<211> LENGTH: 71
<212> TYPE: DNA
<213> ORGANISM: Candida

<400> SEQUENCE: 52
ccgccttacc actaccgtct ttcaagcaac ccaagtcgta ttgctcaaca ccaaacccag    60
cggtttgagg g                                                        71
```

COMPOSITIONS AND METHODS FOR DETECTION OF CANDIDA SPECIES

BACKGROUND OF THE INVENTION

*Candida* species are commensal organisms of humans, usually found on the mucous membranes of the gut, oral cavity, and vaginal introitus, and in warm moist skin folds. *Candida* is the most commonly identified causative agent of oral or vaginal thrush. *Candida* can also cause life-threatening infections in hospital patients. In particular, *Candida* can cause invasive diseases in hosts with altered immunity, such as in patients with HIV infection, patients that have received organ or bone marrow transplants, and in patients experiencing neutropenia after cancer immunotherapy. Patients on intensive regimens of cancer therapy, patients on prolonged broad spectrum antibiotic therapy, patients using invasive devices, and patients on prolonged hospital stays are also at high risk for such infections.

Conventional methods for identifying *Candida* species in patients include morphology and assimilation tests involving blood cultures. These tests can be time consuming, laborious, and often produce false negative results, which adversely affect the targeting of anti-fungal treatment and related point-of-care decisions. In addition, these methods may require extensive, specialized equipment and highly trained operators. These methods may further be limited by their sensitivity or the number of *Candida* species that can be detected simultaneously.

Accordingly, there is a need for compositions, methods, and kits for detecting the presence of *Candida* species in a biological sample in a timely, accurate, and efficient manner.

SUMMARY OF THE INVENTION

The invention features nucleic acid probes and primers that include the sequence of any one of SEQ ID NOs: 1 to 41 (e.g., nucleic acid probes having the sequence of any one of SEQ ID NOs: 1 to 10, such as any one of SEQ ID NOs: 1 to 5), and nucleic acid probes and primers having at least 90%, 95%, 97%, 99%, or more sequence identity to these probes and primers.

The nucleic acid probes and primers can be used to detect a *Candida* species (e.g., *Candida albicans*, *Candida tropicalis*, *Candida krusei*, *Candida glabrata*, *Candida parapsilosis*, *Candida dubliniensis*, *Candida lusitaniae*, and *Candida guillermondi*) in a biological sample. In several embodiments, the nucleic acid probes of the invention include a detection moiety (e.g., a fluorescent label) that is conjugated to the probe. In other embodiments, the nucleic acid probes are conjugated to a magnetic nanoparticle. In another embodiment, the probes of the invention (e.g., SEQ ID NOs: 1 to 5) may be molecular beacon probes that may include a fluorescent label (e.g., FAM, TAMRA, HEX, TMR, Cy3, Cy5, and other spectrally distinguishable dyes) and a quencher (e.g., DDQ-I, Dabcyl, Eclipse, Iowa Black FQ, BHQ-1, QSY-7, BHQ-2, DDQ-II, Iowa Black RQ, QSY-21, BHQ-3). In yet another embodiment, the probes of the invention (e.g., SEQ ID NOs: 1 to 5) may be a "shared-stem" molecular beacon probe. In other embodiments, the nucleic acid probes of the invention (e.g., SEQ ID NOs: 6 to 10) may be conjugated to magnetic nanoparticles.

The invention features a method for detecting at least one *Candida* species (e.g., *Candida albicans*, *Candida tropicalis*, *Candida krusei*, *Candida glabrata*, *Candida parapsilosis*, *Candida dubliniensis*, *Candida lusitaniae*, and *Candida guillermondi*) in a biological sample (e.g., soil, water, food, and tissue or fluid sample from an organism, such as a human). The method includes contacting the biological sample with at least one nucleic acid probe having a sequence selected from any one of SEQ ID NOs: 1 to 41 (e.g., SEQ ID NOs: 1-10, such as SEQ ID NOs: 1-5) under conditions which allow the at least one probe to hybridize to a nucleic acid molecule of the *Candida* species; and detecting hybridization between the at least one probe and the nucleic acid molecule, thereby detecting the at least one *Candida* species. In an embodiment of the method, the probe is a *Candida albicans* probe and has the sequence of SEQ ID NO: 1 or SEQ ID NO: 6; the probe is a *Candida tropicalis* probe and has the sequence of SEQ ID NO: 2 or SEQ ID NO: 7; the probe is a *Candida glabrata* probe and has the sequence of SEQ ID NO: 3 or SEQ ID NO: 8; the probe is a *Candida parapsilosis* probe and has the sequence of SEQ ID NO: 4 or SEQ ID NO: 9; the probe is a *Candida krusei* probe and has the sequence of SEQ ID NO: 5 or SEQ ID NO: 10. In several embodiments, the method features nucleic acid probes that are fluorescently labeled. These nucleic acid probes may be molecular beacon probes (e.g., probes having the sequence of any one of SEQ ID NOs: 1 to 5) that further include a quencher. According to the method of the invention, hybridization of the nucleic acid probe to target *Candida* species nucleic acid molecules produces fluorescence which may be detected in, e.g., a fluorescence based assay (e.g, a real-time or end-point PCR assay) using, e.g., an instrument capable of detecting fluorescence (e.g., a real-time or end-point thermal cycler, or a plate reader). In one embodiment, the method features one or more probes (e.g., 2, 3, 4, or 5 or more probes) that may be labeled with the same or different fluorescent labels (e.g., molecular beacon probes labeled with spectrally distinguishable fluors), and the one or more probes may each be contacted with the sample for use in the same assay, e.g., in a multiplex assay to detect up to five different *Candida* species (e.g., *Candida albicans*, *Candida tropicalis*, *Candida glabrata*, *Candida parapsilosis*, and *Candida krusei*) in a biological sample.

The invention also features a method of using nucleic acid probes conjugated to magnetic nanoparticles (e.g., SEQ ID NOs: 6 to 10 and 13 to 31) to detect *Candida* species in, e.g., an NMR based assay (e.g., an aggregation or disaggregation assay) using an NMR instrument. The method includes contacting the biological sample with at least one nucleic acid probe having a sequence selected from any one of SEQ ID NOs: 6 to 31 (e.g., SEQ ID NOs: 6-10) under conditions which allow the at least one probe to hybridize to a nucleic acid molecule of the *Candida* species; and detecting hybridization between the at least one probe and the nucleic acid molecule, thereby detecting the at least one *Candida* species. In an alternate embodiment of the method, probes conjugated to magnetic nanoparticles can be used in pairwise combinations in an NMR assay to detect *Candida* species, e.g., a probe having the sequence of SEQ ID NO: 6 can be used with a probe having the sequence of any one of SEQ ID NOs: 13 and 14 to detect *Candida albicans*; a probe having the sequence of SEQ ID NO: 7 can be used with a probe having the sequence of any one of SEQ ID NOs: 20 to 25 to detect *Candida tropicalis*; a probe having the sequence of SEQ ID NO: 8 can be used with a probe having the sequence of any one of SEQ ID NOs: 18 and 19 to detect *Candida glabrata*; a probe having the sequence of SEQ ID NO: 9 can be used with a probe having the sequence of any one of SEQ ID NOs: 20 to 25 to detect *Candida parapsilosis*; and/or a probe having the sequence of SEQ ID NO: 10 can be used with a probe having the sequence of any one of SEQ ID NOs: 15 to 17 to detect *Candida krusei*. Binding of probes to target *Candida* nucleic acid molecule can be detected by measuring the NMR relaxation rate in an NMR instrument.

The invention also features primers for DNA sequencing based detection of *Candida* species in a biological sample. In several embodiments, the primer is a *Candida krusei* primer having the sequence of SEQ ID NO: 32 or SEQ ID NO: 33; the primer is a *Candida albicans* primer having the sequence of SEQ ID NO: 34 or SEQ ID NO: 35; the primer is a *Candida glabrata* primer having the sequence of SEQ ID NO: 36 or SEQ ID NO: 37; the primer is a *Candida parapsilosis* primer having the sequence of SEQ ID NO: 38 or SEQ ID NO: 39; or the primer is a *Candida tropicalis* primer having the sequence of SEQ ID NO: 40 or SEQ ID NO: 41. Sequencing may also be preceded by prior amplification using SEQ ID NO: 11 and SEQ ID NO: 12. Alternatively, the sequencing could be done using SEQ ID NO: 11 and SEQ ID NO: 12 and species identification conducted based on analysis of the DNA sequence (i.e., using BLAST).

The invention also features a method of using *Candida* specific primers (e.g., one or more of the DNA primers of SEQ ID NOs: 32 to 41) to detect a *Candida* species in a biological sample. The method may include use of the primers one or more of the primers for DNA sequencing. In several embodiments, the primer is a *Candida krusei* primer having the sequence of SEQ ID NO: 32 or SEQ ID NO: 33; the primer is a *Candida albicans* primer having the sequence of SEQ ID NO: 34 or SEQ ID NO: 35; the primer is a *Candida glabrata* primer having the sequence of SEQ ID NO: 36 or SEQ ID NO: 37; the primer is a *Candida parapsilosis* primer having the sequence of SEQ ID NO: 38 or SEQ ID NO: 39; or the primer is a *Candida tropicalis* primer having the sequence of SEQ ID NO: 40 or SEQ ID NO: 41.

The invention also features fluorescence based methods of using the nucleic acid probes and primers described above (e.g., the nucleic acid molecules of any one or more of SEQ ID NOs: 1 to 41) to detect *Candida* species in a biological sample. These methods include amplifying and sequencing target nucleic acid molecules from *Candida* species in a biological sample. In several embodiments, the methods include, e.g., a TaqMan probe based assay (e.g., real-time or end-point PCR based TaqMan assay using probes having sequence of SEQ ID NOs: 1 to 5); strand-displacement probe based assays (e.g., using probes having sequence of SEQ ID NOs: 1 to 10); PCR assays using DNA binding dyes (e.g., real-time PCR based assay using SYBR® green dye and probes having sequence of SEQ ID NOs: 1 to 41); and in situ hybridization assays using fluorescently labeled species-specific probes (e.g., using probes having sequence of SEQ ID NOs 1 to 41). In several embodiments, the nucleic acid probes having the sequence of any one of SEQ ID NOs: 6-10, and 13-31 may have a detection label (e.g., a fluorescent label), such that the fluorescence detection is via a secondary step (e.g., a digoxigenin label for antibody-based detection using fluorescently labeled anti-digoxigenin antibodies, or a biotin label for detection using fluorescent streptavdin). Alternatively the detection readout may be non-fluorescent. For example, nucleic acid probes having the sequence of any one of SEQ ID NOs: 6-10 and 13-31 may have non-fluorescent detection labels, such as a radioactive isotope for autoradiographic detection, digoxigenin for antibody-based detection using a horse-radish peroxidase (HRP) conjugated anti-digoxigenin antibody, and biotin for streptavidin based detection using HRP conjugated straptividin.

In other embodiments, the fluorescence based methods for detecting the presence of at least one *Candida* species in a biological sample includes the use of molecular beacon probes (e.g., those probes having the sequences of any one of SEQ ID NOs: 1 to 41, and particularly SEQ ID NOs: 1 to 5) having a fluorescent label, which may be the same or different. Following contacting of the probe to the sample that includes nucleic acid molecules from the at least one *Candida* species and hybridization of the probe to the nucleic acid molecules, the presence of the at least one *Candida* species is detected by heating the sample through a melting temperature (Tm) of at least one of the probes to obtain a melting curve. A decrease in fluorescence of the sample at the Tm of at least one the probes indicates the presence of the at least one *Candida* species. Preferably, the molecular beacon probes used in the methods have melting temperatures that vary by at least 1° C., such that a separate melt curve can be obtained for each molecular beacon probe. In particular embodiments, e.g., in which the methods are performed using the PCR conditions set for in Example 1, a decrease in fluorescence at a Tm of ~62-67° C. (e.g., ~64° C.) in the presence of the probe having the sequence of SEQ ID NO: 1 indicates the presence of *Candida albicans* in the sample; a decrease in fluorescence at a Tm of ~55-61° C. (e.g., ~58° C.) in the presence of the probe having the sequence of SEQ ID NO: 2 indicates the presence of *Candida tropicalis* in the sample; a decrease in fluorescence at a Tm of ~65-71° C. (e.g., ~67° C.) in the presence of the probe having the sequence of SEQ ID NO: 3 indicates the presence of *Candida glabrata* in the sample; a decrease in fluorescence at a Tm of ~60-65° C. (e.g., ~62° C.) in the presence of the probe having the sequence of SEQ ID NO: 4 indicates the presence of *Candida parapsilosis* in the sample; and a decrease in fluorescence at a Tm of ~66-72° C. (e.g., ~69° C.) in the presence of the probe having the sequence of SEQ ID NO: 5 indicates the presence of *Candida krusei* in the sample. Many conditions may affect the Tm of a probe during a melting curve analysis, e.g., the salt(s) and salt concentration(s) present in the reaction, the presence of intercalating agents, and the pH of the reaction. Accordingly, the melting temperatures indicated above for SEQ ID NOs: 1-5 are not meant to be limiting and may differ depending upon the conditions used in the method.

In yet other embodiments, one or more of the nucleic acid probes of the invention (e.g., any one of the nucleic acid probes having the sequence of SEQ ID NOs: 1 to 10 and 13 to 41) may be used in an array or microarray based platform for detecting one or more *Candida* species in a biological sample.

Each of the methods of the invention may further include steps for processing samples (e.g., biological samples), which may include one or more of the following: mixing the sample with a lysis agent solution (e.g., a detergent or a hypotonic solution); centrifuging the sample to form a supernatant and a pellet; discarding some or all of the supernatant; and/or resuspending the pellet to form an extract containing the fungal cells. In yet other embodiments, the processing steps may further include one or more of the following: optionally washing the pellet (e.g., with TE buffer) prior to resuspending the pellet; lysing fungal cells of the extract by chemical methods (e.g., using any combination of enzymes, or detergents, or surfactants), mechanical methods (e.g., using beads such as glass beads, bead beating, use of a finned tube in combination with beads, using beads in an agitation mill, use of beads with a chelating agent, use of glass shards, use of solid particles, use of beads or solid particles with mechanical or magnetic vortex centrifugation use of ultrasound, and/or use of sonication), or methods involving temperature changes (e.g., use of heat (e.g., a temperature in the range of about 85° C. to about 125° C., such as a temperature of about 95° C.), use of freeze-thaw, and/or use of freeze-boil) to form a lysate; and/or placing the lysate in a detection tube. Other processing steps may optionally include amplifying nucleic acids present in a processed sample to form an amplified lysate solution; adding all or a portion of the amplied lysate solution to a detection tube that includes one or more *Candida* specific nucleic acid probes or primers and allowing contact between the target nucleic acid molecules in the lysate and the one or more *Candida* specific nucleic acid probes or primers under conditions that allow hybridization of the nucleic acid probe(s) with the target nucleic acid molecules; and detecting hybridization of the nucleic acid probe(s) or primers to the *Candida* target nucleic acid molecules whereby the detection of binding of the *Candida* species-specific probe(s) with *Candida* target nucleic acid molecules present in the biological sample indicates the presence of the *Candida* species in the biological sample.

In another embodiment, the amplified lysate solution described above may be further processed to isolate the *Candida* nucleic acid molecules, e.g., by using an ion exchange column (such as a Qiagen column), glass or silica-base reverse phase adsorption/desorption, SPRI technology, phenol-chloroform extraction and ethanol precipitation, and/or the CTAB method.

In several embodiments, each of the methods of the invention may further include an amplification step for increasing the amount of the target *Candida* nucleic acid molecules to be detected in the biological sample. The amplification may include enzymatic amplification by, e.g., a PCR reaction. Primers having the sequence of SEQ ID NOs: 11 and 12 may be used as pan-*Candida* universal forward and reverse primers, respectively, to produce a *Candida* amplicon. In other embodiments, primers having the sequences of SEQ ID NOs: 6 to 41 can be used in combination with the pan-*Candida* universal primers to produce *Candida* species amplicons. The amplification may be symmetric to produce a double stranded amplicon or the amplification may be asymmetric to produce a single stranded amplicon.

In several embodiments, each of the methods of the invention for detecting at least one *Candida* species in a biological sample can be completed within at least about 5 hours or less (e.g., within 4.0 hours, 3.5 hours, 3.0 hours, 2.5 hours, 2 hours, 1.5 hours, or 1 hour or less). In still other embodiments, each of the methods of the invention can be used to detect at least one *Candida* species in a sample when present at a concentration of at least about 4 *Candida* cells/mL (e.g., 5, 6, 7, 8, 9, 10, 15, 20, 25, 30, 35, 40, 45, or 50 *Candida* cells/mL).

In another embodiment of the compositions and methods of the invention, the biological sample is, e.g., a soil, water, or food sample or a tissue or fluid sample from an organism, such as a human (e.g., whole blood, sweat, tears, urine, saliva, semen, serum, plasma, cerebrospinal fluid (CSF), feces, vaginal fluid or tissue, sputum, nasopharyngeal aspirate or swab, lacrimal fluid, mucous, or epithelial swab (buccal swab), tissues, organs, bone, teeth, and tumors).

In another embodiment, the invention features a kit which includes at least one nucleic acid probe or primer having a sequence selected from any of SEQ ID NOs: 1 to 41 and further includes one or more reagents for attachment of fluorescent label or magnetic nanoparticle to the probe, and/or one or more reagents for sample lysis, fungal lysis, isolation of *Candida* nucleic acid, detection of *Candida* species, and nucleic acid amplification.

BRIEF DESCRIPTION OF THE DRAWINGS

FIG. 1A shows the binding of a conventional molecular beacon probe. FIG. 1B shows the binding of a shared-stem molecular beacon probe of the present invention. A shared-stem molecular beacon probe is designed so that 1) a stem-loop hairpin is formed by the 5' and 3' ends of the probe, 2) a fluorophore and quencher are attached to the 5' and 3' ends and sufficient quenching will occur when the hairpin structure is formed, 3) the probes have a "loop" sequence that is specific for the target *Candida* sequence to be identified in the assay, and 4) sufficient fluorophore signal may be detected upon hybridization of the molecular beacon probe to the specific target sequence of *Candida*. The molecular beacon probes are designed to have a melting temperature (Tm) that is about 5 to 10 degrees (e.g., ~7 degrees) higher than the annealing temperature of amplification primers that may be present with the molecular beacon probes in an assay sample, and the molecular beacon probes are thermodynamically characterized to form no self dimers or heterodimers with other probes or primers (e.g., pan-*Candida* universal PCR primers) that may be present in an assay sample.

FIG. 2A shows the detection of *Candida krusei* in a sample using purified genomic DNA. FIG. 2B shows the detection of *Candida krusei* in a sample prepared from a cell lysate.

FIGS. 3A-3C are titration curves showing detection of *Candida parapsilosis* (FIG. 3A), *Candida tropicalis* (FIG. 3B), and *Candida krusei* (FIG. 3C) using various amounts of purified genomic DNA. FIGS. 3D-3F are titration curves showing detection of *Candida parapsilosis* (FIG. 3D), *Candida tropicalis* (FIG. 3E), and *Candida krusei* (FIG. 3F) using a cell lysate.

FIGS. 4A-4D are graphs showing titration curves for detection of *Candida albicans* and *Candida glabrata* in real-time PCR reactions. FIGS. 4A and 4B are titration curves showing detection of *Candida albicans* (FIG. 4A) and *Candida glabrata* (FIG. 4B) using various amounts of purified genomic DNA. FIGS. 4C and 4D are titration curves showing detection of *Candida albicans* (FIG. 4C) and *Candida glabrata* (FIG. 4D) using a cell lysate.

DETAILED DESCRIPTION OF THE INVENTION

Figure 1A:
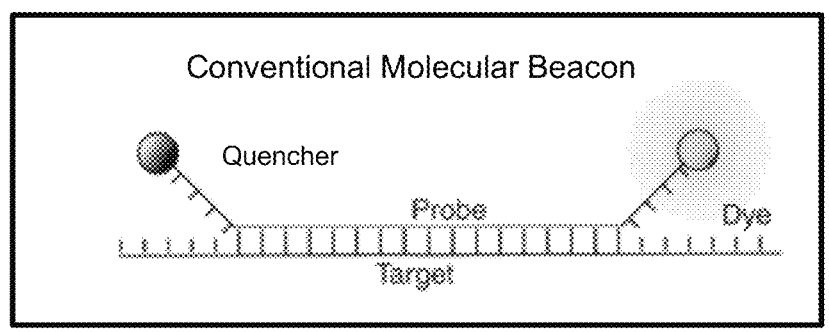
FIGS. 1A and 1B are schematics showing binding of molecular beacon probes to a target nucleic acid molecule.

The invention features compositions, methods, and kits for detecting at least one *Candida* species in a variety of media and biological samples, including, for example, biofluids, tissue samples, culture samples (e.g., a blood culture), food products, water samples, and soil samples. For example, the biological sample may include samples which have been processed to remove patient tissue and/or cellular debris or samples that are substantially unprocessed, such as a whole blood sample. The biological sample may further include cell suspensions or lysates that are produced by the methods of the invention. The biological sample may further include any sample which contains at least one nucleic acid molecule of *Candida* species; or any sample in which the nucleic acid molecules of *Candida* species have been substantially isolated, enriched or purified; or any sample in which the nucleic acid molecules of *Candida* species have been amplified and enriched as an amplicon.

The methods of the invention for detecting a *Candida* species can be performed with little to no sample preparation. In addition, the methods may be performed as a singleplexed assay to detect a single *Candida* species or as a multiplexed assay that allows for detection of multiple *Candida* species in a single sample. The methods of the invention allow for rapid and accurate detection of *Candida* in a biological sample (e.g., a tissue or fluid sample from a patient), which may be used to facilitate point-of-care clinical decision making. The methods described herein can be used to provide clinically and epidemiologically meaningful targeting of anti-fungal drug therapy to patients in need thereof and to provide optimal therapeutic outcome.

The compositions of the invention for use in the detection of a *Candida* species (e.g., one or more of *Candida albicans, Candida tropicalis, Candida krusei, Candida glabrata, Candida parapsilosis, Candida dubliniensis, Candida lusitaniae,* and *Candida guillermondi*) in a biological sample include probes (e.g., molecular beacon probes and NMR assay probes) that can be used to detect nucleic acid molecules of the *Candida* species (e.g., in a real-time probe-based nucleic acid detection assay). The methods of the invention involve contacting a sample that includes a nucleic acid molecule of at least one *Candida* species with at least one probe that is capable of hybridizing to the nucleic acid molecule and detecting hybridization between the probe and the nucleic acid molecule. In multiplexed assays, the sample may be contacted with two or more probes (e.g., probes to any two, three, four, or five or more of the *Candida* species listed above) in order to detect hybridization between the probes and the nucleic acid molecules.

The methods of the invention may be fluorescence based detection methods using fluorescently labeled species-specific probes (e.g., molecular beacon probes), such that hybridization between the probe and the nucleic acid molecule of the *Candida* species may result in a fluorescent signal that can then detected by an appropriate detection device (e.g., a real-time thermal cycler or other fluorescence detection devices known in the art). For example, the probes may be fluorescently labeled molecular beacon probes designed to hybridize to *Candida* species-specific target nucleic acid molecules for detection of specific *Candida* species in a biological sample. Each *Candida* species-specific probe may be labeled with a fluorescent probe that distinguishes that probe from the other *Candida* species-specific probe(s) (e.g., based on differences in the excitation or emission spectra of the different probes). Alternatively, the probes may all include the same fluorescent label, in which case distinguishing the hybridization of each *Candida* species-specific probe to its targets is determined by other techniques, such as differences between the melting temperature (Tm) of each *Candida* species-specific probe, as is discussed below.

The methods of the invention may further include amplifying nucleic acid molecules of the *Candida* species present in the biological sample prior to detection of the *Candida* nucleic acid molecules. Amplification can be used to increase the amount of the *Candida* nucleic acid molecules present in the biological sample in case the original amount of *Candida* target nucleic acid molecules in the biological sample is below the detection limit of the probe(s). Typically such amplification may be done using one or more amplification primers. Any nucleic acid amplification method known in the art (e.g., polymerase chain reaction (PCR)) may be used. Preferably, the amplification method includes the use of primers that amplify nucleic acid molecules of at least one *Candida* species present in the biological sample.

Other methods of the invention include the use of fluorescently labeled probes and/or primers of the invention for detection of at least one *Candida* species in a biological sample in fluorescence based detection assays, for example, in situ hybridization assays. Another detection method employs use of a double strand specific intercalating dye, such as SYBR® (Molecular Probes, Eugene, Oreg.). The fluorescence based assays may be performed in conjunction with real-time PCR detection. The invention also features one or more probes and primers of the invention for use as TaqMan probes in a real-time PCR assay or an end-point PCR assay. Finally, the *Candida* specific primers of the invention (e.g., any one or more of SEQ ID NOs: 1 to 10 and 13 to 41) may be used in sequencing based assays or in array or microarray based platforms in order to detect the presence of at least one *Candida* species in a biological sample.

The methods of the invention also include NMR based assays using *Candida* species-specific probes conjugated to magnetic nanoparticles. For example, in such an assay a sample may be contacted with at least one *Candida* species-specific probe that is conjugated to a magnetic nanoparticle, such that hybridization between the probe and the nucleic acid molecule of the *Candida* species may produce an NMR signal that may be detected by NMR spectroscopy. Other aspects of the compositions, methods, and kits of the invention are described below.

Compositions and Methods for Detecting *Candida* Species in Biological Samples.

The invention features compositions, methods, and kits for detecting at least one *Candida* species in a biological sample. The invention features *Candida* species-specific nucleic acid probes having the sequence of any one of SEQ ID NOs: 1 to 10 and 13 to 31, and probes having at least 90%, preferably at least 95%, more preferably at least 97%, and most preferably at least 99% or more identity to these sequences, that may be employed in a number of assays to detect one or more (for e.g., 2, 3, 4, 5, 6, 7, 8, or more) *Candida* species in a biological sample. For example, the probes may be used to detect one or more of *Candida albicans, Candida tropicalis, Candida krusei, Candida glabrata, Candida parapsilosis, Candida dubliniensis, Candida lusitaniae,* and *Candida guillermondi,* in any combination, in a biological sample.

The methods of the invention include the use of one or more *Candida* specific probes and/or primers for detecting the presence of a *Candida* target nucleic acid molecule present in a biological sample. The methods include one or more of the following steps: (a) providing a biological sample; (b) mixing the sample with a lysis agent solution; (c) centrifuging the sample to form a supernatant and a pellet; (d) discarding some or all of the supernatant; and (e) resuspending the pellet to form an extract containing the fungal cells, optionally washing the pellet (e.g., with TE buffer) prior to resuspending the pellet and optionally repeating step (c); (f) lysing cells of the extract by chemical or mechanical methods to form a lysate; (g) placing the lysate of step (f) in a detection tube; (h) optionally amplifying nucleic acids therein to form an amplified lysate solution; (i) adding to the detection tube one or more *Candida* specific nucleic acid probes and contacting the target nucleic acid molecules in the lysate with one or more *Candida* specific nucleic acid probes under conditions that allow hybridization of the probe(s) (also referred to as binding of the probe(s)) to the target nucleic acid molecules, and (j) detecting hybridization of the probe(s) to the *Candida* target nucleic acid molecules by methods described below. The detection of binding of the *Candida* species-specific probe(s) with *Candida* target nucleic acid molecules present in the biological sample indicates the presence of the *Candida* species in the biological sample. The methods of the invention provide rapid and accurate readouts of the presence of at least one species of *Candida* in the sample. Two or more probes of the invention may be used in the methods of the invention to perform a multiplexing assay that provides for the detection of two or more *Candida* species (e.g., 2, 3, 4, or 5 or more of the *Candida* species described herein) in the biological sample.

In certain embodiments, steps (a) through (h) are completed within at least about 5 hours or less (e.g., within 4.0 hours, 3.5 hours, 3.0 hours, 2.5 hours, 2 hours, 1.5 hours, or 1 hour or less). In particular embodiments, the methods allow for (i) at least 95% correct detection at less than or equal to 5 *Candida* cells/mL in samples spiked into 50 individual healthy patient blood samples; (ii) at least 95% correct detection at less than or equal to 5 *Candida* cells/mL in samples spiked into 50 individual unhealthy patient blood samples; (iii) greater than or equal to 80% correct detection in clinically positive patient samples (e.g., *Candida* positive by another technique, such as by cell culture) starting with 2 mL of biological sample; and/or (iv) at least 90% correct detection in biological samples containing at least 5 *Candida* cells/mL. The invention provides methods in which *Candida* species can be detected at pathogen concentration of, e.g., at least 3 *Candida* cells/mL (e.g., 4, 5, 6, 7, 8, 9, 10, 15, 20, 25, 30, 35, 40, 45, or 50 *Candida* cells/mL) in the sample with a coefficient of variation of less than 15% (e.g., 10 cells/mL with a coefficient of variation of less than 15%, 10%, 7.5%, or 5%; or 25 cells/mL with a coefficient of variation of less than 15%, 10%, 7.5%, or 5%; or 50 cells/mL with a coefficient of variation of less than 15%, 10%, 7.5%, or 5%; or 100 cells/mL with a coefficient of variation of less than 15%, 10%, 7.5%, or 5%). The methods of the invention may be used to detect the presence of *Candida* in a biological sample having a volume in the range of, e.g., 0.05 to 10.0 mL (e.g., a biological sample having a volume in the range of 0.05 to 0.25 mL, 0.25 to 0.5 mL, 0.25 to 0.75 mL, 0.4 to 0.8 mL, 0.5 to 0.75 mL, 0.6 to 0.9 mL, 0.65 to 1.25 mL, 1.25 to 2.5 mL, 2.5 to 3.5 mL, 3.0 to 4.0 mL, or 3.0 to 10 mL).

Species-Specific *Candida* Probes of the Invention

Compositions of the invention include *Candida* species-specific nucleic acid probes that can bind to target sequences within the endogenous nucleic acid sequences of specific *Candida* species. The nucleic acid probes of the invention are designed to hybridize to endogenous nucleic acid molecules of *Candida* species and to provide accurate detection of at least one *Candida* species in a biological sample tested. The nucleic acid probes can be used individually in a detection assay or two or more nucleic acid probes (e.g., 3, 4, or 5 or more probes) can be used in combination, e.g., in a multiplex fluorescence assay, or in an NMR aggregation assay, to detect one or more *Candida* species in the biological sample.

The nucleic acid probes of the invention include: 5'-GGT CAA AGT TTG AAG ATA TAC GTG GTT GAC C-3' (SEQ ID NO: 1) for detecting *Candida albicans*, 5'-CTA GCA AAA TAA GCG TTT TTG GAT GCT AG-3' (SEQ ID NO: 2) for detecting *Candida tropicalis*, 5'-CAG CAC GCA CAA AAC ACT CAC TTA TTG CTG-3' (SEQ ID NO: 3) for detecting *Candida glabrata*, 5'-GTC GAA TTT GGA AGA AGT TTT GGT TTC GAC-3' (SEQ ID NO: 4) for detecting *Candida parapsilosis*, 5'-CCT GAT TTG AGG TCG AGC TTT TTG TAT CAG G-3' (SEQ ID NO: 5) for detecting *Candida krusei*, 5'-GGT CAA AGT TTG AAG ATA TAC GTG G-3' (SEQ ID NO: 6) for detecting *Candida albicans*, 5'-CTA GCA AAA TAA GCG TTT TTG GA-3' (SEQ ID NO: 7) for detecting *Candida tropicalis*, 5'-CAG CAC GCA CAA AAC ACT CAC TTA T-3' (SEQ ID NO: 8)

for detecting *Candida glabrata*, 5'-GTC GAA TTT GGA AGA AGT TTT GGT-3' (SEQ ID NO: 9), for detecting *Candida parapsilosis*, 5'-CCT GAT TTG AGG TCG AGC TTT TTG T-3' (SEQ ID NO: 10) for detecting *Candida krusei*, 5'-AATAAAATGGGCGACGCCAGA-GACCGCCTT-3'(SEQ ID NO: 26) and 5'-GCATCTCCGCCTTATACCACTATCA-3' (SEQ ID NO: 27) for detecting *Candida dubliniensis*, 5'-GGTTGATAT-TCGGAGCAACGCC-3' (SEQ ID NO: 28) and 5'-GTCC-TACCTGATTTGAGGGCGAAAT-3' (SEQ ID NO: 29) for detecting *Candida lusitaniae*, 5'-GCAAACGCCTAGTCCGACTAAGAGTATCACT-CAATACC-3' (SEQ ID NO: 30) and 5'-TGTAAGGCCGGGC-CAACAATACCAGAAATATCCCGC-3' (SEQ ID NO: 31) for detecting *Candida guillermondi*, 5'-CCGAGAGCGAGTGTTGCGAGA-3' (SEQ ID NO: 32) and 5'-TCTCGCAACACTCGCTCTCGG-3' (SEQ ID NO: 33) for detecting *Candida krusei*, 5'-GGTAACGTCCAC-CACGTATATCT-3' (SEQ ID NO: 34) and 5'-AGA-TATACGTGGTGGACGTTACC-3' (SEQ ID NO: 35) for detecting *Candida albicans*, 5'-GGGAGGGATAAGT-GAGTGTGTGCGT-3' (SEQ ID NO: 36) and 5'-ACGCACAAAACACTCACTTATCCCTCCC-3' (SEQ ID NO: 37) for detecting *Candida glabrata*, 5'-GGTA-CAAACTCCAAAACTTCTTCC-3' (SEQ ID NO: 38) and 5'-GGAAGAAGTTTGGAGTTTGTACC-3' (SEQ ID NO: 39) for detecting *Candida parapsilosis*, and 5'-GCTAGTGGCCACCACAATITATITCA-3' (SEQ ID NO: 40) and 5'-TGAAATAAATTGTGTGGCCACTAGC-3' (SEQ ID NO: 41) for detecting *Candida tropicalis*. The invention features the probes described above, as well as probes having at least 90%, 95%, 97%, 99%, or more sequence identity to these probes.

In a further embodiment, one or more of the probes described above may be used in combination with any one of the *Candida* species-specific probes having the sequences of SEQ ID NOs: 13 to 25, which are described in International Application Nos. PCT/US2011/56933 and PCT/US2011/56936, both of which are incorporated herein by reference. These probes include: 5'-ACC CAG COG TTT GAG GGA GAA AC-3' (SEQ ID NO: 13) and 5'-AAA GTT TGA AGA TAT ACG TGG TGG ACG TTA-3' (SEQ ID NO: 14) for detecting *Candida albicans*; 5'-CGC ACG CGC AAG ATG GAA ACG-3' (SEQ ID NO: 15), 5'-AAG TTC AGC GGG TAT TCC TAC CT-3' (SEQ ID NO: 16) and 5'-AGC TTT TTG TTG TCT CGC AAC ACT CGC-3' (SEQ ID NO: 17) for detecting *Candida krusei*; 5'-CTA CCA AAC ACA ATG TGT TG AGA AG-3' (SEQ ID No: 18) and 5'-CCT GAT TTG AGG TCA AAC TTA AAG ACG TCT 0-3' (SEQ ID NO: 19) for detecting *Candida glabrata*; 5'-AGT CCT ACC TGA TTT GAG GTCNitIndAA-3' (SEQ ID NO: 20), 5'-CCG NitIndGG OTT TGA GGG AGA AAT-3' (SEQ ID NO: 21), 5'-AAA GTT ATG AAATAA ATT GTG GTG GCC ACT AGC-3' (SEQ ID NO: 22), 5'-ACC CGG GGGTTT GAG GGA GAA A-3' (SEQ ID NO: 23), 5'-AGT CCT ACC TGA TTT GAG GTC GAA-3' (SEQ ID NO: 24), and 5'-CCG AGG GTT TGA GGG AGA AAT-3' (SEQ ID NO: 25) for detecting either *Candida parapsilosis* or *Candida tropicalis*. In other embodiments, reverse complement versions of one or more of the nucleic acid molecules of SEQ ID NOs 1 to 41 may also be used as probes for detecting *Candida* species in a biological sample or as primers for amplying one or more *Candida* nucleic acid molecules in a biological sample in an amplification step.

In addition, *Candida* specific nucleic acid molecules with at least 90% sequence identity (or at least 90%, 95%, 97%, 99%, or more sequence identity) to the sequences of SEQ ID NOs: 1 to 41, or to the reverse complement sequences of SEQ ID NOs: 1 to 41, may be used for detecting, amplifying, or both amplifying and detecting *Candida* species nucleic acid molecules in a biological sample.

The *Candida* species-specific probes of the invention may also include a detection label (e.g., a fluorescent detection label) or may be conjugated to a magnetic nanoparticle for use in the methods of the invention for detecting at least one *Candida* species in a biological sample. Detection labels and magnetic nanoparticles for use in the present invention, and methods for using probes of the invention that include a detection label or that are conjugated to a magnetic nanoparticle, are described in detail below.

Composition and Methods for Fluorescence-Based Detection of *Candida* Species in Biological Samples The invention features *Candida* species-specific nucleic acid probes that can bind to target sequences within the endogenous nucleic acid sequences of *Candida*. These probes can be used to detect the presence of specific species of *Candida* in biological samples. The probes may be labeled with a fluorescent label (also referred to as a fluorophore) and applied to a *Candida* lysate prepared from the biological sample. Preferably, the fluorophore-labeled probe emits a fluorescent signal upon hybridization of the probe to its target sequence and a fluorescent signal is not produced by unbound probe, e.g., as described in U.S. Patent Application No. US 2010/0221710A1 (incorporated herein by reference). The fluorescent signal produced upon hybridization between probe and target nucleic acid of the *Candida* species can be detected in a fluorescence detection device (e.g., a real time thermal cycler or other detection device known in the art). Each of the *Candida* species-specific probes described herein may be differentially labeled with fluorphores with spectrally distinguishable emission spectra for use in a multiplex fluorescence detection assay. In such a multiplex assay, two or more fluorescently labeled nucleic acid probes (e.g., 3, 4, or 5 or more probes), each having a different fluorophore attached, can be used in combination to rapidly and accurately detect multiple different *Candida* species in a biological sample.

The *Candida* species-specific probes of the present invention may also be used as "molecular beacons." Methods to prepare and use molecular beacons are fully described in, e.g., U.S. Pat. Nos. 5,118,801, 5,312,728, and 5,925,517, each of which is incorporated herein by reference. Typically, molecular beacon probes have a fluorophore attached at the 5' end of the probe and a non-fluorescent quencher attached at the 3' end of the probe. Molecular beacons further contain complementary sequences at the 5' and 3' ends allowing these two ends to hybridize. The two ends flank a middle intervening "loop" sequence. The 5' and 3' ends of the molecular beacon can hybridize to each other and form an intramolecular stem structure and the middle intervening sequence region forms a "loop." The "loop" part of the molecular beacon can hybridize to the target nucleic acid.

Under conditions (e.g., an appropriate temperature range) when the "loop" part of the probe cannot hybridize with the target nucleic acid sequence, the 5' and 3' ends of the probe form the intramolecular stem structure. As a result, the proximity between the fluorophore and quencher causes the quencher to absorb any fluorescence emitted by the fluorophore and no fluorescence is produced. However, under different conditions (e.g., an appropriate temperature range) that allow the "loop" part of the probe to hybridize to the target nucleic acid sequence, the stem structure is not formed, the fluorophore is separated from the quencher and, as a result, a fluorescent signal is produced.

The molecular beacon probes of the present invention are designed to detect specific nucleic acid target sequences in *Candida* species via species-specific "loop" sequences. Use of different fluorophore labels on the 5' end of each of the species-specific probes can allow use of multiple molecular beacon probes in a multiplex assay to simultaneously and rapidly detect multiple *Candida* species in a biological sample. Alternatively, each of the *Candida* species-specific probes described herein can be prepared as molecular beacon probes and labeled with the same fluorphore or with fluorophores having overlapping emission spectra for use in a multiplex fluorescence detection assay. Since each of the *Candida* species-specific molecular beacon probes have a different melting temperature (Tm), hybridization of each of the *Candida* species-specific molecular beacon probes to their target nucleic acid molecules can be detected by assaying fluorescence through a range of temperatures that includes the Tm of each probe used.

For example, a sample containing nucleic acid molecules from a *Candida* species may be contacted with a *Candida albicans* specific molecular beacon probe having a Tm of ~64° C. (e.g., a Tm of 62-67° C.) and a HEX fluorophore and a *Candida glabrata* specific molecule beacon probe having a Tm of ~67° C. (e.g., a Tm of 65-71° C.) and a HEX fluorophore. Fluorescence in the sample may be due to binding of the *C. albicans* or the *C. glabrata* probes or both. To determine which probe(s) are bound to their target nucleic acid molecules, the temperature of the sample may be raised from, e.g., 40° C. to 80° C. while detecting changes in fluorescence in the sample. If *C. albicans* nucleic acid molecules are present in the sample, there will be a change in fluorescence as the sample temperature increases through 64° C. In this case, half of the *Candida albicans*-specific molecular beacon probes will dissociate from their target nucleic acid molecules, which will result in a decrease in fluorescence as the probe melts off and the stem-loop structure reforms and quenches the fluorescence of those probes. If *C. glabrata* nucleic acid molecules are present in the sample, there will be a decrease in fluorescence as the temperature is increased through 67° C. In this case, half of the *C. glabrata* probes will dissociate from their target nucleic acid molecules, which will result in a decrease in fluorescence as the probe melts off and the stem-loop structure reforms and quenches the fluorescence of those probes. There would be no melt curves in the absence of *Candida* nucleic acid molecules. Similarly, no change in fluorescence around 64° C. would indicate the absence of *Candida albicans* nucleic acid molecules, while no change in fluorescence around 67° C. would indicate the absence of *Candida glabrata*.

The amount of *Candida* specific target nucleic acid molecules present in a biological sample may be sufficient for detection according to the methods of the present invention (e.g., by contact with the species-specific probes of the invention) without the need for amplification of the target nucleic acid molecules. However, it may be preferable to increase the amount of target nucleic acid molecules present in the biological sample prior to detection (e.g., if the amount of target nucleic acid molecules present in the biological sample is below the detection limit of the probe (s)). In this case, an optional amplification step may be performed to amplify the target nucleic acid molecules of the *Candida* species, which will increase the amount of the target nucleic acid molecules present in the biological sample that may be bound by the probe(s). Typically, such amplication may be performed prior to contact with the probe by using, e.g., PCR or any other amplification methods known in the art.

The amplification reaction mixture may include, e.g., (1) the target nucleic acid molecule(s) and (2) forward and/or reverse amplification primers specific for the target nucleic acid molecule(s). The forward and/or reverse primers may include, for example, the sequence 5'-GGC ATG CCT GT TGA GCG TC-3' (SEQ ID NO: 11) and the sequence 5'-GCT TAT TGA TAT GCT TAA GTT CAG CGG GT-3' (SEQ ID NO: 12), each of which is universal to multiple *Candida* species, as described in International Application Nos. PCT/US2011/56933 and PCT/US2011/56936. These primers are referred to herein as "pan-*Candida* primers." Alternatively, the forward and/or reverse primers can include primers that recognize species-specific target nucleic acids and can have the sequence of any one of SEQ ID NOs: 6 to 10 and 13 to 25. The amplification produces a *Candida* amplicon in the reaction mixture. The amplification may include substantially more forward or reverse primers if the amplification is to be asymmetric, or both a forward and a reverse primer in equimolar ratios, if the amplification is to be symmetric, as described in detail below.

In a further embodiment, the detection probe(s) may be added at any time during the amplification step. For example, a fluorescently labeled molecular beacon probe (or probes in a multiplex assay) may be added to a sample prior to amplification (e.g., prior to, or substantially simultaneously with, addition of the amplification primer(s)) so that during the amplification step the probe binds to its target and a fluorescent signal can be detected in real time. A real-time PCR machine may used in such an assay and allows continuous monitoring of the fluorescence every time the species-specific probe hybridizes with its target nucleic acid sequence. Alternatively, a fluorescently labeled molecular beacon probe (or probes in a multiplex assay) can be added to a sample after an amplification step, and under conditions that allow the probe to hybridize with its target *Candida* amplicon, whereby hybridization of the probe to an amplicon of a *Candida* target nucleic acid molecule can be detected by recording the resulting fluorescent signal.

The detection device for detecting a fluorescent signal may include any device that can provide temperature conditions for probe hybridization and that can detect a fluorescent readout when the hybridization occurs. For example, such a device may include a thermal cycler (e.g., a real-time thermal cycler). Alternatively, the device can be a fluorescent plate reader, a flow-cytometer detecting particles with conjugated capture probes, a fluorescence microscope, or a microarray-based capture/detection, each with the ability to maintain the samples at a specific temperature range and the ability to detect and record fluorescent signals.

Fluorescently Labeled Species-Specific *Candida* Probes

Nucleic acid probes of the invention having the sequence of any one of SEQ ID NOs: 1 to 5 (or probes having at least 90%, 95%, 97%, or 99% or more sequence identity to the sequence of SEQ ID NOs: 1 to 5) may be used in an assay to detect at least one *Candida* species in a biological sample. Preferably, such probes include a detection label, such as a fluorophore. The fluorophore can be conjugated to the 5' end or the 3'end of the probe, or alternatively it can be attached internally within the probe. Fluorophores that are known in the art and can be used for conjugation to probes of the invention, as well as the different types of devices that may be used to detect such probes (e.g., different types of thermal cyclers), are described in, e.g., Table 2 of Marras (*Methods Mol. Biol.* 335:3-16, 2006 (incorporated herein by reference)). Preferred examples of a fluorophore for labeling of the probes of the invention include, for example, FAM, TAMRA, HEX, TMR, Cy3, and Cy5. For multiplexing assays utilizing multiple probes for the simultaneous detection of multiple *Candida* species, it may be preferable to attach fluorophores with spectrally distinguishable emission spectra onto each species-specific probe in order to discriminate between binding of each probe to its respective target. Alternatively, as described above; multiplex assays may also be performed using multiple different *Candida* species specific probes that are labeled with the same fluorophore. Fluorescently labeled probes may include, without limitation, TaqMan probes (also known in the art as 5' nuclease probes), strand-displacement probes, or molecular beacon probes.

The fluorescently labeled probes of the invention having sequences of SEQ ID NOS: 1 to 5 (or probes having at least 90%, 95%, 97%, or 99% or more sequence identity to the sequence of SEQ ID NOs: 1 to 5) can be molecular beacon probes that may further include a quencher attached to the probe in addition to the fluophore, as described above. For example, the fluorophore can be attached to the 5' end of the probe and the quencher can be attached to the 3' end of the probe or vice versa. The choice of the specific quencher depends on the specific fluorophore that is attached to the probe. Examples of quenchers that can be conjugated to the molecular beacon probes of the invention include, for example, DDQ-I, Dabcyl, Eclipse, Iowa Black FQ, BHQ-1, QSY-7, BHQ-2, DDQ-II, Iowa Black RQ, QSY-21, BHQ-3. Examples of preferred fluorescent-quencher pairs used in the art are described in, e.g., Marras (supra; see Table 2 therein), and include, without limitations, FAM-BHQ-1, TET-BHQ-1, HEX-BHQ-1, FAM-Dabcyl, TET-Dabcyl, and HEX-Dabcyl.

Figure 1B:
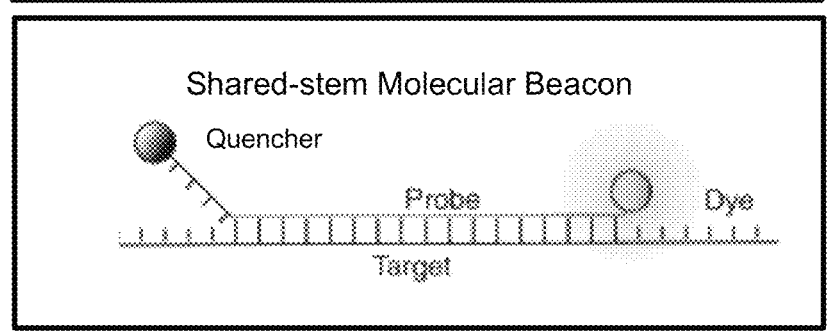

Nucleic acid probes of the invention having the sequence of SEQ ID NOs: 1 to 5 (or probes having at least 90%, 95%, 97%, or 99% or more sequence identity to the sequence of SEQ ID NOs: 1 to 5) may be conventional molecular beacon probes (see FIG. 1A) or "shared-stem" molecular beacon probes (see FIG. 1B). Shared-stem probes have one or more of the following characteristics:

1) About five to ten nucleotides (for e.g., 4, 5, 6, 7, 8, or 9 nucleotides; preferably 5 or 6 nucleotides) at the 5' end that are complementary to about five to ten nucleotides (for e.g., 4, 5, 6, 7, 8, or 9 nucleotides; preferably 5 or 6 nucleotides) at the 3' end such that the 5' and 3' ends of the probe can hybridize to form a "stem" structure;

2) A species-specific sequence of about 17 to 30 nucleotides in length (for e.g., 15, 16, 17, 18, 19, 20, 21, 22, 23, 24, 25, 26, 27, 28, 29, or 30 nucleotides) that resides in the middle "loop" region of the probe, that has limited secondary structure, and that can bind to specific target sequences in the endogenous nucleic acid of each *Candida* species;

3) A shared-stem design such that the 5' end of the nucleic acid probe has the ability to hybridize to a target sequence within the endogenous nucleic acid of each *Candida* species, whereas about 1 to 20 nucleotides (e.g., about 5-6 nucleotides) of the 3' stem region do not hybridize with the endogenous nucleic acid of *Candida*; and 4) A predicted stem Tm of ~50° C. and a probe/target duplex Tm of between 50° C. and 75° C. (e.g., ~60° C.).

When the probe is a molecular beacon probe that includes a fluorophore and a quencher, the shared-stem feature of the probe improves signal to background ratios, improves sensitivity due to increased stability of the molecular beacon probe-target duplex, potentially enhances fluorogenic signals, and reduces the secondary structure in the probe backbone.

Each of the species-specific molecular beacon probes may be labeled with a different fluorophore (e.g., FAM, TAMRA, HEX, TMR, Cy3 and Cy5), such that the molecular beacon probes may be applied simultaneously to a single sample in a multiplex assay that allows simultaneous detection of multiple *Candida* species based on spectral resolution of the emission maxima for the different fluorescent labels. The molecular beacon probes are designed to minimize heterodimer formation between the beacons so the detection is amenable to multiplexing using different fluorophores, as described above.

Probes of the invention having the sequence of SEQ ID NOs: 1 to 5 (or probes having at least 90%, 95%, 97%, or 99% or more sequence identity to the sequence of SEQ ID NOs: 1 to 5) may be used in combination with an optional PCR based amplification step. The amplification step, when performed in the methods of the invention, may be symmetric or asymmetric PCR. Symmetric PCR can be performed using the pan-*Candida* universal primers as the forward and reverse primers, which can amplify a *Candida* amplicon to increase the amount of all *Candida* species target nucleic acid molecules present in the biological sample. Symmetric PCR may also utilize the pan-*Candida* universal forward primer in combination with the complement of one or more of SEQ ID NOs: 6 to 10 and 13 to 25, or the pan-*Candida* universal reverse primer in combination with the one or more of SEQ ID NOs: 6 to 10 and 13 to 25. Asymmetric PCR can be performed using the pan-*Candida* forward or reverse primer, one or more of SEQ ID NOs: 6 to 10 and 13 to 25 as the forward primer, or one or more of the complement of SEQ ID NOs: 6 to 10 and 13 to 25 as the reverse primer.

For example, *Candida* specific target nucleic acid molecules prepared from a suspension of lysed *Candida* cells can be added to a tube containing an asymmetric PCR master mix that includes the pan *Candida* primers and the molecular beacon probe(s). The reaction tube may then be placed in a real-time thermal cycler machine programmed to perform multiple rounds of amplification of the target nucleic acid molecules characteristic of the *Candida* species present in the mix. This allows continuous monitoring of the fluorescence every time the probe hybridizes with its target nucleic acid sequence.

The molecular beacon probes may be designed to have a Tm about 7 degrees (for e.g., 3, 4, 5, 6, 7, 8, 9, or 10 degrees) higher than the annealing temperature of the primers and are thermodynamically characterized to form no self or heterodimers with the pan-*Candida* universal primers or the primers of SEQ ID NOs: 6 to 10 and 13 to 25. The limit of detection of these molecular beacon probes is about 3 cells/m (for e.g., at least 1, 2, 3, 4, 5, 6, 7, 8, 9, 10, 15, 20, 25, 30, 35, 40, 45, or 50 cells/mL).

The amplification reaction may also be performed using pairwise combinations of one of the universal primers and a primer selected from any one of SEQ ID NOs: 13 to 25. The concentration of one of the primers may be in excess compared to the other for asymmetric PCR. Such pairwise combinations may be designed based-on the desired *Candida* species amplicon and the genomic position of the probe- and the primer sequences. Such pairwise combinations may include, without limitation, the universal forward primer in combination with: a) a reverse primer having the reverse complement of primer of SEQ ID NO: 13 for amplifying a *Candida albicans* amplicon, b) a reverse primer having the reverse complement sequence of SEQ ID NOs: 20 to 25 for amplifying a *Candida tropicalis* or *Candida parapsilosis* amplicon, c) a reverse primer having the reverse complement sequence of SEQ ID NOs: 18 or 19 for amplifying a *Candida glabrata* amplicon, and d) a reverse primer having the reverse complement sequence of SEQ ID NOs: 15 to 17 for amplifying a *Candida krusei* amplicon.

Alternatively, the universal reverse primer may be used in combination with: a) a forward primer having the sequence of SEQ ID NO: 13 for amplifying a *Candida albicans* amplicon, b) a forward primer having the sequence of SEQ ID NOs: 20 to 25 for amplifying a *Candida tropicalis* or *Candida parapsilosis* amplicon, c) a forward primer having the sequence of SEQ ID NOs: 18 or 19 for amplifying a *Candida glabrata* amplicon, and d) a forward primer having the sequence of SEQ ID NOs: 15 to 17 for amplifying a *Candida krusei* amplicon.

Alternate Methods for Detecting *Candida* Species Using Probes and Primers of the Invention In a further embodiment of the invention, all probes and primers described above can be used by methods known in the art for detecting, amplifying and sequencing target nucleic acid molecules from *Candida* species in samples. For example, probes having the sequence of any one of SEQ ID NOs: 6 to 10, and 13-41 can be used to detect one or more *Candida* species in a biological sample in one or more of the following methods: a) a TaqMan probe based assay (e.g., real-time PCR based TaqMan assay), b) strand-displacement probe based assays, c) PCR assays using DNA binding dyes (e.g., real-time PCR based assay using SYBR® green dye), d) in situ hybridization assays using fluorescently labeled species-specific probes, e) sequencing based assays (e.g., dideoxy-sequencing using probes having SEQ ID NOs: 32 to 41), and f) array or microarray based assays. Probes having the sequence of any one of SEQ ID NOs: 6-10, and 13-41 may have detection labels such that the fluorescence detection is via a secondary step. In such cases, the detection labels on the probe may include, without limitation, digoxigenin label for antibody-based detection using fluorescent labeled anti-digoxigenin antibodies, or biotin label for detecting using fluorescent streptavdin. Probes having the sequence of any one of SEQ ID NOs: 6-10, and 13-41 may also have non-fluorescent detection labels including, but not limited to, radioactive isotopes for autoradiographic detection, digoxigenin for antibody-based detection using a horse-radish peroxidase (HRP) or alkaline phosphatase conjugated anti-digoxigenin antibody, and biotin for streptavidin based detection using HRP or alkaline phosphatase conjugated streptavidin. Non-fluorescent methods for detecting probe binding, such as autoradiographic detection, HRP- or alkaline phosphatase-based detection, colorimetric or chemiluminescent detection, and detection using array or microarray platforms are well known in the art and can be adapted by those of skill in the art to the methods described herein for detecting *Candida* species in a biological sample.

Compositions and Methods for Detecting *Candida* Species in an NMR Based Assay

An alternate method for detecting *Candida* species in a biological sample may include the use of an NMR based assay using species-specific probes that are designed to be compatible with such assays. Use of NMR based assays to detect *Candida* species are described in, e.g., International Application No. PCT/US2011/56933 and International Application No. PCT/US2011/56936.

The present invention features probes having the sequence of any one of SEQ ID NOs: 6 to 10 and 26 to 31 that are conjugated to magnetic nanoparticles for use in an NMR based assay for detecting at least one *Candida* species in a biological sample. These nucleic acid probes of the invention include, e.g., 5'-GGT CAA AGT TTG AAG ATA TAC GTG G-3' (SEQ ID NO: 6) for detecting *Candida albicans*, 5'-CTA GCA AAA TAA GCG TTT TTG GA-3' (SEQ ID NO: 7) for detecting *Candida tropicalis*, 5'-CAG CAC GCA CAA AAC ACT CAC TTA T-3' (SEQ ID NO: 8) for detecting *Candida glabrata*, 5'-GTC GAA TIT GGA AGA AGT TTT GGT-3' (SEQ ID NO: 9), for detecting *Candida parapsilosis*, 5'-CCT GAT TTG AGG TCG AGC TTT TG T-3' (SEQ ID NO: 10) for detecting *Candida krusei*, 5'-AATAAAATGGGCGACGCCAGAGACCGCCTT-3' (SEQ ID NO: 26) and 5'-GCATCTCCGCCTTATACCAC-TATCA-3' (SEQ ID NO: 27) for detecting *Candida dubliniensis*, 5'-GGTTGATATTTCGGAGCAACGCC-3' (SEQ ID NO: 28) and 5'-GTCCTACCTGATTTGAGGGCGAAAT-3' (SEQ ID NO: 29) for detecting *Candida lusitaniae*, and 5'-GCAAACGCCTAGTCCGACTAAGAGTATCACT-CAATACC-3' (SEQ ID NO: 30) and 5'-TGTAAGGCCGGGC-CAACAATACCAGAAATATCCCGC-3' (SEQ ID NO: 31) for detecting *Candida guillermondi*. Probes having sequences with at least 90%, e.g., at least 95%, 97%, and 99% or more sequence identity to the sequences of SEQ ID NOs: 6 to 10 and 26 to 31 and that are bound to nanoparticles are also included in the present invention.

As further described in International Application No. PCT/US2011/56933 and International Application No. PCT/US2011/56936, the NMR assay may be an "aggregation assay" in which magnetic nanoparticles can include one or more populations having a first probe and a second probe conjugated to their surface, the first probe operative to bind to a first segment of the target nucleic acid and the second probe operative to bind to a second segment of the target nucleic acid. Upon probe hybridization to the target nucleic acid, the magnetic particles form aggregates.

The terms "aggregation" and "aggregate" are used interchangeably in the context of the magnetic particles described herein and mean that two or more magnetic particles are brought into close proximity to one another as a result of target nucleic aid molecule binding by the nanoparticle-conjugated probes. Hybridization between probe and target nucleic acid may be detected in a nuclear magnetic resonance (NMR) instrument by measuring the "NMR relaxation rate," as described in International Application No. PCT/US2011/56933 and International Application No. PCT/US2011/56936. NMR relaxation rate refers to a measurement of any of the following in a sample: $T_1$, $T_2$, $T_1/T_2$ hybrid, $T_{1rho}$, $T_{2rho}$, and $T_2^*$. The methods of the invention are designed to produce an NMR relaxation rate characteristic of whether a target nucleic acid from *Candida* is present in a biological sample. In some instances the NMR relaxation rate is characteristic of the quantity of target nucleic acid present in the sample. In addition to the "aggregation" assay described above, the probes can be used in "disaggregation" assays, according to methods described in International Application No. PCT/US2011/56933 and International Application No. PCT/US2011/56936.

The *Candida* lysate containing the target nucleic acid may be contacted with magnetic nanoparticles conjugated to species specific probes having the sequence of any one or more of SEQ ID NOs: 6 to 10 and 26 to 31, or their complements, and used in combination with magnetic nanoparticles conjugated with species-specific probes having the sequence of SEQ ID NOs: 13 to 25. For example, the probe of SEQ ID NO: 6 may be used in combination with a probe having the sequence of any one of SEQ ID NO: 13 or 14 for detecting *Candida albicans*; the probe of SEQ ID NO: 7 may be used in combination with a probe having the sequence of any one of SEQ ID NOs: 20 to 25 for detecting *Candida tropicalis*; the probe of SEQ ID NO: 8 may be used in combination with a probe having the sequence of any one of SEQ ID NO:18 or 19 for detecting *Candida glabrata*; the probe of SEQ ID NO: 9 may be used in combination with a probe having the sequence of any one of SEQ ID NOs: 20 to 25 for detecting *Candida parapsilosis*; and the probe of SEQ ID NO: 10 may be used in combination with a probe having the sequence of any one of SEQ ID NOs: 15 to 17 for detecting *Candida krusei*.

The NMR based detection methods may also include an optional amplification step, which may be performed to amplify the target nucleic acid prior to or substantially during contacting of the biological sample with the probe-nanoparticle conjugate. The amplification step of this method may include one or more of the following steps:
  (a) performing one or more cycles of amplification with one or more of the *Candida* specific PCR primers described above in a detection tube,
  (b) addition of the probe-nanoparticle conjugate,
  (c) exposing the amplification reaction mixture, or an aliquot thereof, to conditions permitting the aggregation or disaggregation of the superparamagnetic particles,
  (d) detecting hybridization between probes and target nucleic acid by NMR and measuring the NMR signal from the detection tube,
  (e) repeating steps (a)-(d) until a desired amount of amplification is obtained; and
  (f) on the basis of the result of step (d), quantifying the amplicons present at the corresponding cycle of amplification.

The amplification can be performed using combinations of the pan-*Candida* universal primers. Optionally, probes having sequences of any one or more of SEQ ID NOs: 6 to 10 and 13 to 31 may also be used as forward and/or reverse primers (in a symmetric or an asymmetric amplification reaction) or in combination with one of the pan-*Candida* primers (in a symmetric or an asymmetric amplification reaction) to produce a *Candida* amplicon. The amplification may be performed using pairwise combinations of one of the universal primers and a primer selected from any one of SEQ ID NOs: 6 to 10 and 13 to 31 (or its complement). Such pairwise combinations may be designed based on the desired *Candida* species amplicon and the genomic positions of the probe and the primer sequences to be used. Such pairwise combinations may include, without limitation, use of the universal forward primer in combination with: a) a reverse primer having the complement of any one of SEQ ID NOs: 6 or 13 for amplifying a *Candida albicans* amplicon; b) a reverse primer having the complement sequence any one of SEQ ID NOs: 7, 9, or 20 to 25 for amplifying a *Candida tropicalis* or *Candida parapsilosis* amplicon; c) a reverse primer having the complement sequence of any one of SEQ ID NOs: 8, 18, or 19 for amplifying a *Candida glabrata* amplicon; d) a reverse primer having the complement sequence of any one of SEQ ID NOs: 10 or 15 to 17 for amplifying a *Candida krusei* amplicon; e) a reverse primer having the complement sequence of any one of SEQ ID NO: 26 or 27 for amplifying a *Candida dubliniensis* amplicon; f) a reverse primer having the complement sequence of any one of SEQ ID NO: 28 or 29 for amplifying a *Candida lusitaniae* amplicon; g) a reverse primer having the complement sequence of any one of SEQ ID NO: 30 or 31 for amplifying a *Candida guillermondi* amplicon.

Alternatively, the universal reverse primer may be used in combination with: a) a forward primer having the sequence of any one of SEQ ID NO: 6 or 13 for amplifying a *Candida albicans* amplicon; b) a forward primer having the sequence of any one of SEQ ID NOs: 7, 9, or 20 to 25 for amplifying a *Candida tropicalis* or *Candida parapsilosis* amplicon; c) a forward primer having the sequence of any one of SEQ ID NOs: 8, 18, or 19 for amplifying a *Candida glabrata* amplicon; d) a forward primer having the sequence of any one of SEQ ID NOs: 10 or 15 to 17 for amplifying a *Candida krusei* amplicon; e) a forward primer having the sequence of any one of SEQ ID NOs: 26 or 27 for amplifying a *Candida dubliniensis* amplicon; f) a forward primer having the sequence of SEQ ID NO: 28 or 29 for amplifying a *Candida lusitaniae* amplicon; g) a forward primer having the sequence of any one of SEQ ID NO: 30 or 31 for amplifying a *Candida guillermondi* amplicon.

The probe-nanoparticle conjugate can be added to the amplification mix prior to, or during, the PCR reaction, such that the probe-nanoparticle conjugates are present during the PCR reaction and under appropriate conditions can bind with the target nucleic acid. Alternatively, the probe-nanoparticle conjugate can be added to the *Candida* lysate after the amplification step to detect the amplified *Candida* target nucleic acid.

The term "magnetic particle" refers to particles including materials of high positive magnetic susceptibility such as paramagnetic compounds, superparamagnetic compounds, and magnetite, gamma ferric oxide, or metallic iron. The magnetic nanoparticles may have a mean diameter of from 150 nm to 1200 nm (for e.g., 150, 250, 350, 450, 550, 650, 750, 850, 950, 1050, 1150, and 1200 nm) and are typically a composite material including multiple metal oxide crystals and an organic matrix. The magnetic particles of the invention may have a surface decorated with functional groups that can be conjugated to, e.g., one or more nucleic acid probes of having the sequence of any one of SEQ ID NOs: 6 to 10 and 13-31, their complements, or probes having at least 90%, 95%, 97%, 99%, or more sequence identity to the sequences of SEQ ID NOs: 6 to 10 and 13-31 and their complements. The base particle for use in the methods of the invention can be any of the commercially available particles further described in, e.g., Table 2 of the International Application No. PCT/US2011/56933. The magnetic nanoparticle maybe modified using protein blockers, as described in the International Application No. PCT/US2011/56933, in order to reduce non-specific binding.

The nucleic acid probes of the invention can be linked to the metal oxide of the nanoparticle through covalent attachment to a functionalized polymer or to non-polymeric surface-functionalized metal oxides. In the latter method, the magnetic particles can be synthesized according to the method of, e.g., Albrecht et al., (*Biochimie*, 80:379, 1998; incorporated herein by reference), which includes coupling dimercapto-succinic acid to the iron oxide to provide a carboxyl functional group.

Where the probes of the invention are attached to magnetic particles via a functionalized polymer associated with the metal oxide, preferably the polymer is hydrophilic. In certain embodiments, the probe-conjugated nanoparticles may be made-using probes that have terminal amino, sulfhydryl, or phosphate groups and superparamagnetic iron oxide magnetic particles bearing amino or carboxy groups on a hydrophilic polymer. Several methods for synthesizing carboxy and amino derivatized-magnetic particles are known in the art.

Probes of the invention may also be attached to a magnetic nanoparticle via ligand-protein binding interaction, such as biotin-streptavidin, in which the ligand is covalently attached to the oligonucleotide and the protein to the particle, or vice versa. This approach can allow for more rapid reagent preparation for NMR assays.

Amplification of Nucleic Acid Molecules of *Candida*

As is discussed above, the methods of the invention can optionally include an amplification step in which specific regions of the *Candida* genome are amplified to form a *Candida* species amplicon.

The terms "amplification" or "amplify" or derivatives thereof as used herein to mean one or more methods known in the art for copying a target or template nucleic acid, thereby increasing the number of copies of the target or template nucleic acid. Amplification may be exponential or linear. Amplification may also be asymmetric (only the sense or antisense strand is copied) or symmetric (both the sense and antisense strands are copied). Nucleic acid molecules amplified in this manner form an "amplified region" or "amplicon."

The amplification reaction increases the number of copies of *Candida* target nucleic acid molecules present in a *Candida* lysate solution. Preferably, amplification of the *Candida* target nucleic acid molecules produces a lysate solution that includes from 40% (w/w) to 95% (w/w) target nucleic acid (e.g., from 40 to 60%, from 60 to 80%, or from 85 to 95% (w/w) target nucleic acid) and from 5% (w/w) to 60% (w/w) nontarget nucleic acid (e.g., from 5 to 20%, from 20 to 40%, or from 40 to 60% (w/w) nontarget nucleic acid). The species-specific nucleic acid probes described above can be added to the lysate solution (prior to or after amplification) for hybridization to the target nucleic acid molecules and for detection of specific *Candida* species present in the biological sample.

Figure 6:
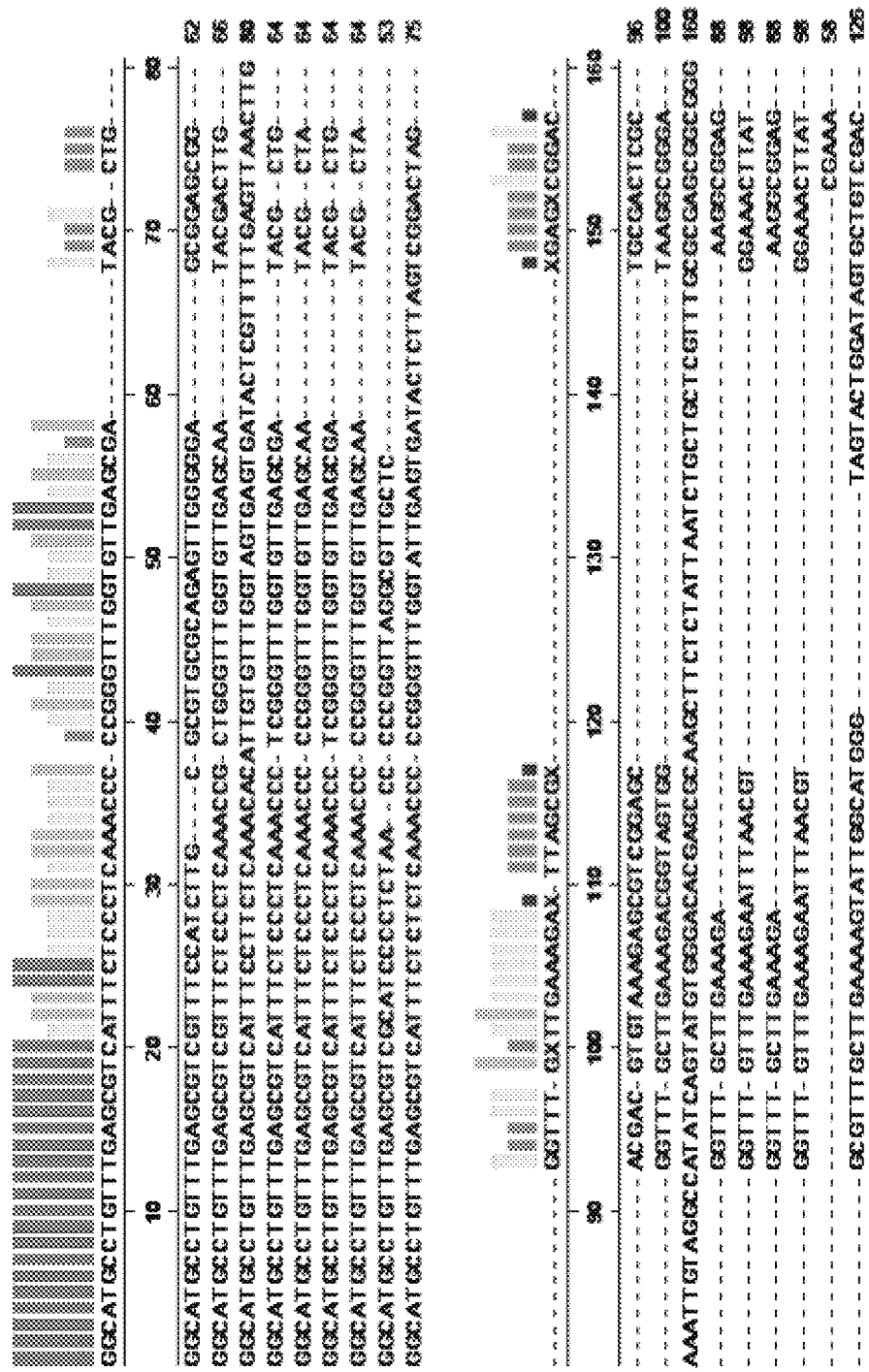
FIG. 6 is a schematic showing alignment of *Candida* amplicon sequences that are generated by amplification using the pan-*Candida* primers. The alignment shows species-specific differences within this amplicon. Shown are sequences for *C. krusei* (pan fungal amplicon; SEQ ID NO. 42), *C. albicans* (pan fungal amplicon; SEQ ID NO: 43), *C. glabrata* (pan fungal amplicon; SEQ ID NO: 44), *C. parapsilosis* (pan *candida* amplicon; SEQ ID NO. 45), *C. tropicalis* (pan *candida* amplicon; SEQ ID NO: 46), *C. parapsilosis* (pan *candida* amplicon, SEQ ID NO: 47), *C. tropicalis* (pan *candida* amplicon, SEQ ID NO: 48), *C. lusitaniae* (ITS2; SEQ ID NO: 49), *C. guillermondi* (amplicon 2; SEQ ID NO: 50), and a majority sequence (SEQ ID NO: 51).

In the context of the present invention, amplification produces *Candida* species amplicons. For example, as shown in FIG. 6, amplification with the pan-*Candida* primers produces an amplicon which has regions which differ in sequence between *Candida* species and regions which share a common sequence between all *Candida* species. The regions that are different can be used to differentiate between *Candida* species.

Primers for amplification can be readily designed by those skilled in the art to target a specific template nucleic acid sequence. In certain preferred embodiments, the resulting amplicons are short and allow for rapid cycling and generation of copies. The size of the amplicon can vary as needed to provide the ability to discriminate target nucleic acids from non-target nucleic acids. For example, amplicons can be less than about 1,000 nucleotides in length. Desirably the amplicons are from 100 to 500 nucleotides in length (e.g., 100 to 200, 150 to 250, 300 to 400, 350 to 450, or 400 to 500 nucleotides in length).

While the exemplary methods described hereinafter relate to amplification using polymerase chain reaction ("PCR"), numerous other methods are known in the art for amplification of nucleic acids (e.g., isothermal methods, rolling circle methods). Alternate methods for amplification are described in further detail in, e.g., the International Application No. PCT/US2011/56933 and International Application No. PCT/US2011/56936.

Amplification may be performed by methods including a polymerase chain reaction (PCR) and the amplification reaction mixture may include, e.g., (1) the target nucleic acid molecule(s), (2) forward and/or reverse amplification primers specific for the target nucleic acid molecule(s), and (3) a detection probe(s) that can bind to target sequences within the amplified target nucleic acid (the amplicon). In certain embodiments, the invention features the use of polymerase enzymes compatible with complex biological samples such as whole blood, e.g., NEB Hemoklentaq, DNAP Omniklentaq, Kapa Biosystems whole blood enzyme, Thermo-Fisher Finnzymes Phusion enzyme.

In certain embodiments, the primers can include the pan-*Candida* primer sequences where the forward and reverse primer have the sequence 5'-GGC ATG CCT GTT TGA GCG TC-3' (SEQ ID NO: 11) and the sequence 5'-GCT TAT TGA TAT GCT TAA GTT CAG CGG GT-3' (SEQ ID NO: 12), respectively. In other embodiments, specific *Candida* species amplicons may be amplified by the use of appropriate forward and reverse primers that bind to and produce species-specific *Candida* amplicons, as described above.

In certain embodiments the amplification may be asymmetric, in which the concentration of one of the primers in the reaction is higher than the concentration of the other primer. For example, the concentration of the forward amplification primer may be about 4 times (e.g., 2, 3, 4, 5, 10, 20, 50, times) the concentration of the reverse primer, or viceversa. This reaction condition results in preferential amplification of single stranded amplicons. In other embodiments, the amplification may be symmetric. In this case, the PCR reaction may be performed using equal concentrations of the forward and reverse primers, which results in double stranded amplicons. Methods for performing asymmetric and symmetric PCR are known in the art (see, for example, Poddar, *Molecular and Cellular Probes* 14: 25-32, 2000, incorporated herein by reference). In one particular example, the pan-*Candida* universal forward and/or reverse primers can be used in pairwise combinations with any one of the primers having the sequence of SEQ ID NOs: 6-10 and 13-31, or their complements, to produce species-specific *Candida* amplicons.

Biological Samples that can be Tested for the Presence of a *Candida* Species

The compositions, methods, and kits featured in the invention may be used to detect at least one (and preferably two or more) *Candida* species that may be present in a biological sample. By biological sample is meant a variety of media including, but not limited to, biofluids, tissue samples, culture samples (e.g., a blood culture), food products, water samples, and soil samples that contain one or more species of *Candida* cells. For example, the biological sample can be a sample which has been processed to remove cellular and tissue debris and patient nucleic acids, or the biological sample may be a sample that has been processed to partially or fully isolate *Candida* cells from the sample. The biological sample may include, e.g., cell suspensions or cell lysates. The biological sample may also be one that has been substantially unprocessed, such as a whole blood sample. The biological sample may also be any sample in which the nucleic acid molecules of *Candida* have been substantially isolated, enriched by amplification or other methods, or purified. The biological sample can be any sample that contains at least one genome equivalent of *Candida*.

Typically, the sample is human in origin, but alternatively it maybe non-human in origin (such as from an animal). The biological sample is preferably a fluid sample, and can typically comprise a body fluid, but may also be a solid tissue sample. The sample may be, e.g., whole blood, sweat, tears, urine, saliva, semen, serum, plasma, cerebrospinal fluid (CSF), feces, vaginal fluid, sputum, nasopharyngeal aspirate or swab, and lacrimal fluid. The sample can also be mucous or epithelial swab (buccal swab), tissues, organs, bone, teeth, and tumors.

The compositions, methods, and kits of the invention can also be used to monitor and diagnose infectious disease in a multiplexed, automated, no sample preparation system. Examples of pathogens that may be detected using the devices, kits, and methods of the invention include, e.g., *Candida*, e.g., *C. albicans, C. glabrata, C. krusei, C. tropicalis, C. parapsilosis, C. dubliniensis, C. lusitaniae*, and *C. guillermondi*. The methods of the invention can be used to identify and monitor the pathogenesis of disease in a subject, to select therapeutic interventions, and to monitor the effectiveness of the selected treatment.

The methods of the invention an also be used to monitor sepsis or septic shock. Sepsis and septic shock are serious medical conditions that are characterized by a whole-body inflammatory state (systemic inflammatory response syndrome or SIRS) and the presence of a known or suspected infection. Sepsis is defined as SIRS in the presence of an infection, septic shock is defined as sepsis with refractory arterial hypotension or hypoperfusion abnormalities in spite of adequate fluid resuscitation, and severe sepsis is defined as sepsis with organ dysfunction, hypoperfusion, or hypotension. To determine whether a patient has sepsis, it is necessary to identify the presence of a pathogen and to identify bacterial or fundal origin. To most effectively treat a patient, the earliest initiation of appropriate therapy is important to a satisfactory outcome. Antimicrobial and other treatments for sepsis rely on the classification of pathogens at multiple levels, including the identification of an agent as 1) bacterial, viral, fungal, parasitic or otherwise; 2) gram positive, gram negative, yeast, or mold, 3) species, and 4) susceptibility.

Each of these levels of specificity improves the time to initiation of appropriate therapy, and each step further down the track will lead to a narrowing of therapeutic agents to the most specific set. Without absolute susceptibility data; empiric approaches to care rely on the information available about the pathogen (at whichever level) and the pattern of pathogen frequency and susceptibility trends in the hospital of another site of care. Thus, certain categories of pathogens are frequently presumed to be causative until there are more data to refine the pairing of pathogen and therapy. The methods of the present invention can be used to facilitate early diagnosis of fungal (e.g., *Candida*) infection, and thus can provide improved therapeutic outcomes in patients diagnosed using such methods.

Biological Sample Lysis Methods

In any of the methods of the invention for detection of *Candida* species in a biological sample, the disruption of patient cells present in the biological sample can be carried out using a lysis agent (e.g., a lysis buffer, a hypotonic buffer, or a nonionic detergent). Lysis buffers which can be used in the methods of the invention include, without limitation, isotonic solutions of ammonium chloride (optionally including carbonate buffer and/or EDTA), and hypotonic solutions. Alternatively, the lysis agent can be aqueous solution of one or more detergents (e.g., nonionic, ionic, polymeric, and zwitterionic, such as, (e.g., nonyl phenoxy-polyethoxylethanol (NP-40), 4-octylphenol polyethoxylate (Triton-X100), Brij-58), or related surfactants, and mixtures thereof). The lysis agent disrupts at least some of the sample cells, allowing a large fraction of certain components to be separated. For example, if the biological sample is whole blood, the lysis agent disrupts at least some of the red blood cells present in the sample, allowing a large fraction of certain components of whole blood (e.g., certain whole blood proteins) to be separated (e.g., as supernatant following centrifugation) from the *Candida* fungal cells present in the whole blood sample. The *Candida* fungal cells can then be optionally washed to further remove whole blood lysed debris from the sample. The lysed sample may then be centrifuged to produce a supernatant and a pellet. The resulting pellet containing the *Candida* cells may be reconstituted to form a suspension of *Candida* cells, which may be further treated as discussed below.

Fungal Lysis Methods

In any of the methods of the invention for detection of *Candida* species in a biological sample, the isolated *Candida* cells in suspension may be lysed using either chemical or mechanical methods known in the art in order to release the target nucleic acid from the *Candida* cells. For example, chemical lysis methods include, without limitation, treatment of fungal cells with one or more enzymes, such as Zymolyase (see, e.g., Park et al., *J. Clin Microbiol.* 38: 2829-2839, 2000, incorporated herein by reference), or detergents, or surfactants. Alternatively, *Candida* cells may be lysed using mechanical methods known in the art. For example, mechanical lysis methods include, without limitation, use of solid particles, sand, or glass shards, use of glass beads as described in, e.g., Hirose et al., *Biotechnology Techniques* 13: 571-575, 1999 (incorporated herein by reference), use of beads with sonication or mechanical vortex centrifugation or magnetic vortex centrifugation as described in, e.g., U.S. Pat. No. 7,723,095 (incorporated herein by reference), bead beating described in International Application No. PCT/US2011/56933 and International Application No. PCT/US2011/56936, use of a finned tube, e.g., use of a finned tube with beads added to the tube for lysing the sample, as described in U.S. Patent Application No. 61/601,842 (incorporated herein by reference), use of ultrasound as described in, e.g., U.S. Pat. No. 6,686,195 (incorporated herein by reference), heating the sample or applying high pressure as described in, e.g., Chisti and Moo-Young, *Biotechnology/The Science and Business*, Chapter 13, Harwood Academic Publishers, 1999 (incorporated herein by reference), use of solid particles in the presence of chelating agents as described in, e.g., U.S. Pat. No. 7,494,771 B2 (incorporated herein by reference), use of high speed agitation bead mills as described in, e.g., Kula and Schutte, *Biotechnology Progress* 3(1): 31, 1987 (incorporated herein by reference), use of cell wall breaking devices as described in, e.g., U.S. Pat. No. 4,295,613 (incorporated herein by reference), and freeze-boil and freeze-thaw methods (see, e.g., Griffiths et al., *J. Med Microbiol.* 55: 1187-1191, 2006, incorporated herein by reference).

When beads are used to lyse the *Candida* cells, the beads may be 0.5 mm glass beads, 0.7 mm silica beads, 0.1 mm silica beads, 0.7 mm silica beads, yttrium stabilized zirconium oxidized beads, or a mixture of differently sized beads made of inert material (see, e.g., Curran and Evans, *J. Bacteriol.* 43(2): 125, 1942; and Lamanna and Mallette, *J. Bacteriol.* 67(4): 503, 1954, incorporated herein by reference). Typically, the beads are added to the tube containing the *Candida* cells in suspension and the tube is placed in a vortexer (e.g., a Biospec bead beater) and vortexed at maximum speed for 5-15 minutes (e.g., 5 minutes) so that the *Candida* cells are lysed and the endogenous target nucleic acids are released.

If desired, the lysate can be further processed to purify the Candida nucleic acid molecules by methods known in the art which include, without limitations, use of an ion exchange columns, e.g., an anion exchange column, such as a Qiagen column, phenol-chloroform extraction and ethanol precipitation methods as described in Maniatis et al. "Molecular Cloning—A laboratory manual" Cold Spring Harbor Press, 1982 (incorporated herein by reference), use of fungal DNA extraction kits as described in, e.g., Fredricks et al., *J. Clin. Microbiol.* 43 (10): 5122-5128, 2005 (incorporated herein by reference), use of the "CTAB method" as described in Zhang et al., *FEMS Microbiology Letters* 145(2): 261-265, 1996 (incorporated herein by reference), and spry technology.

Kits for Detection of Candida Species

Kits of the invention may include one or more probes and primers having the sequence of any of SEQ ID NOs: 1 to 41 (e.g., SEQ ID NOs: 1 to 5) for detecting Candida species in biological samples. The kits may further include instructions for using one or more of the probes and primers in methods for detecting a Candida species (e.g., *Candida albicans, Candida tropicalis, Candida krusei, Candida glabrata, Candida parapsilosis, Candida dubliniensis, Candida lusitaniae,* and *Candida guillermondi*) in a biological sample.

In addition, the kits may include any combination of reagents for sample lysis, fungal cell lysis, amplification of Candida nucleic acid molecules, and reagents for detection of Candida species appropriate for fluorescence detection and/or NMR based detection.

The kits may also include one or more reagents for fluorescently labeling a probe or probes (e.g., probes having SEQ ID NOs: 1 to 5) or the kits may include a probe or probes that are already fluorescently labeled (e.g., the probes of the kits may be molecular beacon probes having the sequence of any one of SEQ ID NOs: 1 to 5). The kits may also include reagents for conjugating nanoparticles to a probe or probes of the invention (e.g., a probe having the sequence of any one of SEQ ID NOs: 6 to 10 and 13 to 31) or the kits may include a probe or probes that are already conjugated to nanoparticles for use in NMR based detection assays.

Uses for Candida Specific Molecular Beacon Probes

The Candida specific molecular beacon probes described herein can be used in several ways, including the following:

a) If intact fungal cells can be enriched and/or partially or fully purified from a biological matrix (e.g., a biological sample, such as whole blood, serum, sputum, urine, etc.), the Candida specific molecular beacon probes can be used in a method to detect and identify a fungal species in the biological matrix;

b) If fungal DNA can be isolated from any biological sample, the Candida specific molecular beacon probes can be used to detect the Candida DNA, as well as identify the particular fungal species;

c) In a rapid and convenient method for fungal identification in a post blood-culture sample. This could be through direct detection, using the Candida specific molecular beacon probes, of Candida within a small aliquot (~5-50 uL) of the blood culture media and/or removal of 5 mL or less of the media, centrifugation and removal of the supernatant, and resuspension of the cells within TE. This potentially could be done at earlier time points during blood culture incubation to maximize time to result;

d) In a robust and quantitative assay for quantification of fungal cells used to generate Candida spiked whole blood samples from frozen cell bullets;

e) In a high throughput and sensitive tool to quantify and ensure lot to lot reproducibility and stability of Candida external controls; and f) In a high throughput and sensitive orthogonal assay to monitor the enzymatic activity of a polymerase for use in an amplification reaction using Candida specific nucleic acid molecules and/or to monitor the activity and reliability of a PCR master mix (lot to lot reproducibility, shelf life stability, material compatibility, and ship stability).

The following examples are meant to illustrate the invention. They are not meant to limit the invention in any way.

EXAMPLES

Example 1: Detection of *Candida krusei* Using a Species-Specific Molecular Beacon Probe in a Real-Time PCR Assay A general protocol for detecting Candida species using fluorescently labeled molecular beacon probes (e.g., SEQ ID NOs: 1 to 5) is described below. For preparation of Candida cell lysate, 1 mL of PBS, TE, or YPD broth containing spiked Candida cells at concentrations ranging from $10^4$ to 1 Candida cells were added to a tube containing 300 mg of yttrium stabilized zirconium oxide beads. The cells were harvested via centrifugation at 6000G for 5 minutes and the supernatant was removed. The cells were then washed with 150 to 1500 µL of TE buffer and harvested again via centrifugation at 60000. 100 µL of TE buffer was added to the tubes and the tube was placed in a vortexer (Biospec bead beater) at maximum speed for 5 minutes. The resulting Candida lysate was removed and transferred to a clean 1.7 mL polypropylene tube, and was either used directly in a real-time PCR reaction or was further processed using a Qiagen kit to isolate the Candida genomic DNA containing the target nucleic acid molecules.

An asymmetric master mix was prepared using pan-Candida forward and reverse primers, as shown in Table 1.

TABLE 1

| Component | per 100 uL reaction |
|---|---|
| Nuclease free water* | 17.33 |
| 5X reaction Buffer | 20 |
| 10 mM mix | 2 |
| 100 uM Forward Primer | 0.3 |
| 100 uM Reverse Primer | 0.075 |
| 100 uM Molecular beacon | 0.3 |
| Hemoklentaq | 10 |
| sum | 50.00 |

The molecular beacon probe (at a concentration of 300 nM; the molecular beacon probe may be used at a concentration of ~100-600 nM) was added directly to the asymmetric master mix. Fifty microliters of cell lysate or diluted genomic DNA was added directly to the master mix in a 96-well plate and the plate was loaded onto a real-time PCR thermal cycler (i.e. Roche LightCycler). The real-time cycling parameters used for asymmetric amplification are described in Table 2.

TABLE 2

| Pre-incubation: 95 C., 5 minutes, ramp rate: 4.4 degrees C./sec |
| --- |
| Amplification-45 cycles |
| Denaturation: 95 C., 20 sec, ramp rate: 4.4 degrees C./sec |
| Annealing: 60 C., 40 sec, ramp rate: 2.2 degrees C./sec |
| Elongation: 68 C., 30 sec, ramp rate: 4.4. degrees C./sec |
| Melt Curve |
| 95 C., 1 minute, ramp rate: 4.4 degrees C./sec |
| 40 C., 1 minute, ramp rate: 2.2 degrees C./sec |
| 80 C., continuous, ramp rate: 0.29 degrees C./sec |

In this example, a molecular beacon probe specific for *Candida krusei* (having the sequence of SEQ ID NO: 5) was used. Real-time PCR data are provided below for reactions containing 0 to 50,000 genomic equivalents of isolated *Candida krusei* genomic DNA added as template to each reaction. Four replicates for each reaction condition were performed and the mean Cp values (cross-over point), standard deviation of Cp (Std. Cp) and CV (coefficient of variation, n=3 or n=4) were calculated for each experiment described below. The average amplification efficiency and the PCR efficiency for the reactions were also calculated in each case to monitor that the results were not affected by amplification artifacts.

Figure 2A:
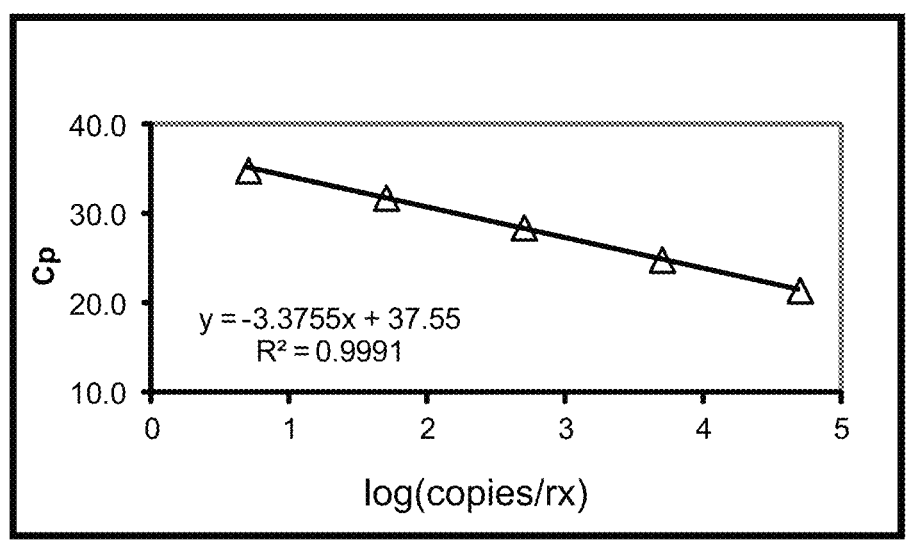
FIGS. 2A and 2B are graphs showing detection of *Candida krusei* in real-time PCR reactions.

As shown in Table 3, and FIG. 2A, the *Candida krusei* molecular beacon probe was used successfully to detect the target nucleic acid molecule in the genomic DNA isolated from *Candida krusei*. The "ND" indicates "not detected" and no Cp was reported.

TABLE 3

| | *C. krusei* genomic | | | | | | |
| --- | --- | --- | --- | --- | --- | --- | --- |
| equivalents/rx | Cp1 | Cp2 | Cp3 | Cp4 | Average | Std Cp | CV |
| 50,000 | 21.36 | 21.29 | 21.34 | 21.5 | 21.37 | 0.09 | 0.4% |
| 5,000 | 24.91 | 24.86 | 24.94 | 24.87 | 24.90 | 0.04 | 0.1% |
| 500 | 28.23 | 28.27 | 28.11 | 28.33 | 28.24 | 0.09 | 0.3% |
| 50 | 31.81 | 31.74 | 31.78 | 31.59 | 31.73 | 0.10 | 0.3% |
| 5 | 35.09 | 34.98 | 34.95 | 35.19 | 35.01 | 0.11 | 0.3% |
| no template | ND | ND | ND | ND | ND | | |
| amplification efficiency = | 1.96 | | | | | | |
| PCR efficiency = | 96% | | | | | | |

The *Candida krusei* specific molecular beacon probe was also used to detect *C. krusei* in a *Candida* lysate prepared as described above. Real-time PCR data are provided below for PCR reactions containing *Candida* lysate prepared using different concentrations of *Candida* cells. The average amplification efficiency and the PCR efficiency for the reactions were also calculated to determine whether use of a lysate as the source of the genetic material affected the amplification and PCR efficiency.

Figure 2B:
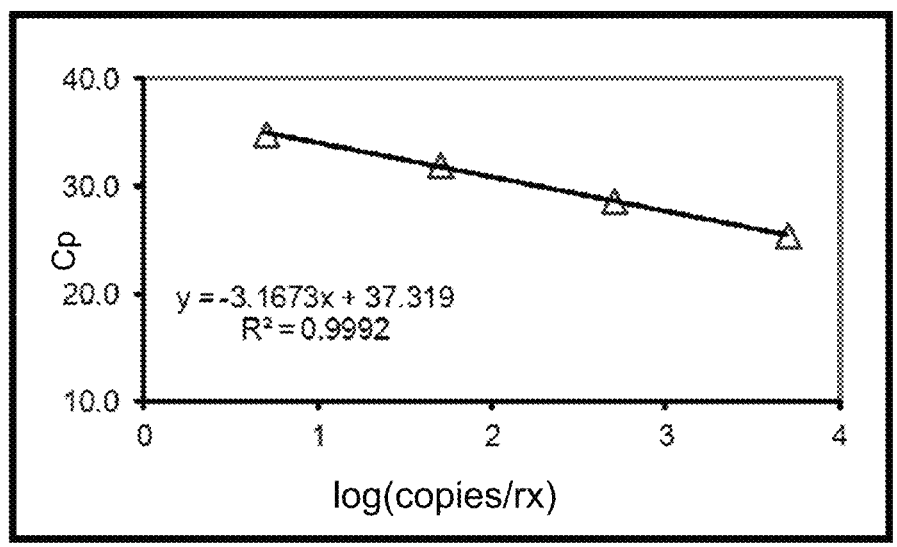

As seen in Table 4 below, the amplification and PCR efficiencies when lysate was used are similar to the results obtained when isolated genomic DNA template was used (see Table 3). Thus, genetic material from a *Candida* cell lysate can be directly used in a PCR reaction to amplify *Candida* target nucleic acid molecules. Also, as shown in FIG. 2B, *Candida krusei* was successfully detected in a sample prepared as a *Candida* lysate using the *C. krusei* specific molecular beacon probe.

TABLE 4

| | *C. krusei* | | | | | | | | | |
| --- | --- | --- | --- | --- | --- | --- | --- | --- | --- | --- |
| | 1rst run | | | | 2nd run | | | | Std | |
| cells/rx | Cp1 | Cp2 | Cp3 | Cp4 | Cp1 | Cp2 | Cp3 | Average | Cp | CV |
| 400 | 27.98 | 27.96 | 27.88 | 27.9 | 28.01 | 28.03 | 27.96 | 27.96 | 0.05 | 0.2% |
| 40 | 31.26 | 31.25 | 31.46 | 31.24 | 31.53 | 31.51 | 31.51 | 31.39 | 0.14 | 0.4% |
| 4 | 34.34 | 34.13 | 33.96 | 34.5 | 34.34 | 34.86 | 34.59 | 34.39 | 0.30 | 0.9% |
| amplification efficiency = | 2.05 | | | | | | | | | |
| PCR efficiency = | 105% | | | | | | | | | |

Figure 3A:
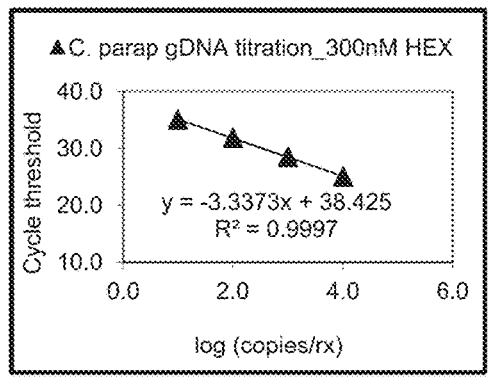
FIGS. 3A-3F are graphs showing titration curves for detection of *Candida* species in real-time PCR reactions.
Figure 3B:
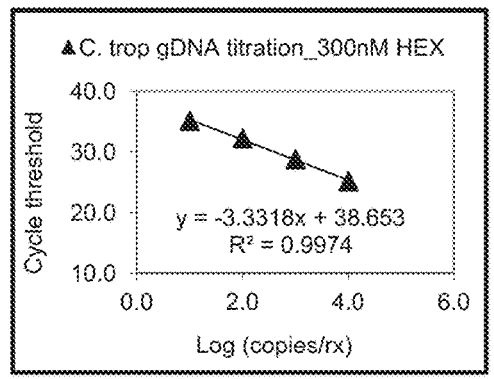
Figure 3C:
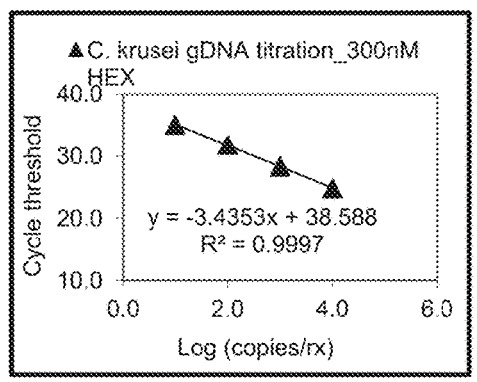
Figure 3D:
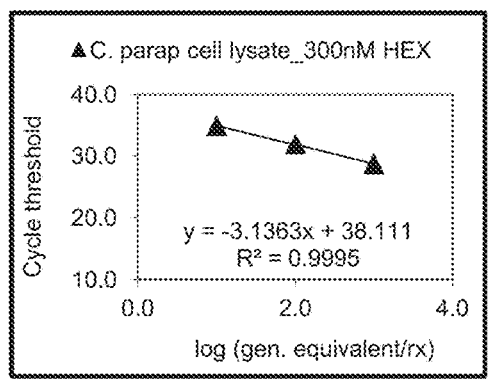
Figure 3E:
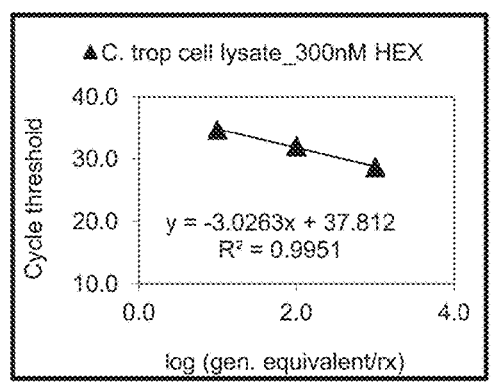
Figure 3F:
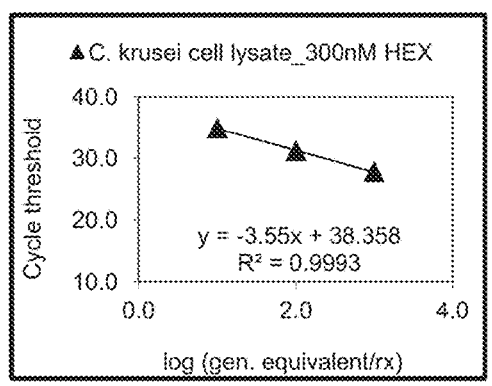

Additional data showing the successful use of a HEX-labeled *C. krusei* probe with genomic *Candida krusei* DNA are shown in Table 5 and FIG. 3C, and additional data showing the successful use of a HEX-labeled *C. krusei* probe with *Candida krusei* are shown in Table 6 and FIG. 3F. The volume of diluted genomic DNA or lysate added in these PCR reactions was 100 ul instead of 50 ul as in the reactions described above.

TABLE 5

| | *C. krusei* gDNA titration_300 nM HEX | | | | | | |
| --- | --- | --- | --- | --- | --- | --- | --- |
| copies/rx | Cp1 | Cp2 | Cp3 | Cp4 | Average | Std Cp | CV |
| 10,000 | 24.77 | 24.84 | 24.8 | 24.8 | 24.79 | 0.04 | 0.1% |
| 1,000 | 28.34 | 28.29 | 28.3 | 28.4 | 28.32 | 0.04 | 0.1% |
| 100 | 31.79 | 31.8 | 31.8 | 31.9 | 31.81 | 0.03 | 0.1% |
| 10 | 35.07 | 35.01 | 35.2 | 35.1 | 35.08 | 0.07 | 0.2% |
| no template | | | | | ND | ND | ND |
| amplification efficiency | 1.95 | | | | | | |
| PCR efficiency | 95% | | | | | | |

TABLE 6

| | C. krusei cell lysate_300 nM HEX | | | | | | |
|---|---|---|---|---|---|---|---|
| genomic equivalent/rx | Log | Cp1 | Cp2 | Cp3 | Cp4 | Average | Std Cp | CV |
| 1,000 | 3.0 | 27.81 | 27.59 | 27.9 | 27.8 | 27.76 | 0.12 | 0.4% |
| 100 | 2.0 | 31.21 | 31.1 | 31.2 | 31.1 | 31.15 | 0.05 | 0.2% |
| 10 | 1.0 | 34.72 | 34.88 | 34.9 | 34.9 | 34.86 | 0.10 | 0.3% |
| no cell lysate | | | | 17.9 | 12.3 | 15.05 | 3.96 | 26.3% |
| amplification efficiency | | 1.91 | | | | | | |
| PCR efficiency | | 91% | | | | | | |

Example 2: Detection of C. parapsilosis Using a Species-Specific Molecular Beacon Probe in a Real-Time PCR Assay A HEX labeled C. parapsilosis probe (having the sequence of SEQ ID NO: 4) was used at 300 nM concentration in a real-time PCR assay that was performed according to the parameters described in Table 1 above. 100 µl of diluted genomic DNA was added to the PCR reaction mix and 45 cycles of amplification were performed with an annealing temperature of 55° C. A titration using different amounts of genomic DNA template was performed. Real-time PCR data are provided in Table 7 below for reactions containing 0 to 10,000 copies of genomic DNA per reaction. Four replicates for each reaction condition were performed and the average Ct values were calculated. The average amplification efficiency and the PCR efficiency for the reactions were also calculated. Table 7 and FIG. 3A show that the C. parapsilosis molecular beacon probe was used successfully to detect the target nucleic acid molecule using genomic DNA isolated from Candida parapsilosis.

TABLE 7

| | C. parapsilosis gDNA titration_300 nM HEX | | | | | | | |
|---|---|---|---|---|---|---|---|---|
| copies/rx | Log | Cp1 | Cp2 | Cp3 | Cp4 | Average | Std Cp | CV |
| 10,000 | 4.0 | 25.01 | 24.96 | 24.99 | 25.09 | 25.01 | 0.06 | 0.2% |
| 1,000 | 3.0 | 28.45 | 28.5 | 28.44 | 28.48 | 28.47 | 0.03 | 0.1% |
| 100 | 2.0 | 31.84 | 31.81 | 31.85 | 31.83 | 31.83 | 0.02 | 0.1% |
| 10 | 1.0 | 35.27 | 35.06 | 34.99 | 34.74 | 35.02 | 0.22 | 0.6% |
| no template | | | | | | ND | ND | ND |
| amplification efficiency | | 1.99 | | | | | | |
| PCR efficiency | | 99% | | | | | | |

Next, a similar assay was performed using a Candida parapsilosis lysate rather than genomic DNA. A titration was performed with 100 ul of a Candida lysate prepared with different concentrations of C. parapsilosis cells. Real-time PCR data are provided below (Table 8) for PCR reactions containing Candida lysate having 0 to 1000 (i.e., 0, 10, 100, or 1,000) genomic equivalents of Candida parapsilosis genomic DNA per reaction. As shown in Table 8 and FIG. 3D, Candida parapsilosis was successfully detected using the C. parapsilosis specific molecular beacon probe at all genomic equivalents prepared using a Candida lysate.

TABLE 8

| | C. parapsilosis cell lysate_300 nM HEX | | | | | | |
|---|---|---|---|---|---|---|---|---|
| genomic equivalent/rx | Log | Cp1 | Cp2 | Cp3 | Cp4 | Average | Std Cp | CV |
| 1,000 | 3.0 | 28.61 | 28.65 | 28.73 | 28.66 | 28.66 | 0.05 | 0.2% |
| 100 | 2.0 | 31.88 | 31.89 | 31.97 | 31.93 | 31.92 | 0.04 | 0.1% |
| 10 | 1.0 | 34.91 | 34.96 | 34.9 | 34.97 | 34.94 | 0.04 | 0.1% |
| no cell lysate | | | | | | | | |
| amplification efficiency | | 2.08 | | | | | | |
| PCR efficiency | | 108% | | | | | | |

Example 3: Detection of C. tropicalis Using a Species-Specific Molecular Beacon Probe in a Real-Time PCR Assay A HEX labeled C. tropicalis probe (having the sequence of SEQ ID NO: 2) was used at 300 nM concentration in a real-time PCR assay that was performed according to the parameters described in Table 1 above. 100 µl of diluted genomic DNA was added to the PCR reaction mix and 45 cycles of amplification were performed with an annealing temperature of 55° C. A titration using different amounts of genomic DNA template was performed. Real-time PCR data are provided in Table 9 for reactions containing 0 to 10,000 (i.e., 0, 100, 1,000, and 10,000) copies of genomic DNA per reaction. Four replicates for each reaction condition were performed and the average Ct values were calculated. The average amplification efficiency and the PCR efficiency for the reactions were also calculated. Table 9 and FIG. 3B show that the C. tropicalis molecular beacon probe was used successfully to detect the target nucleic acid molecule using genomic DNA isolated from Candida tropicalis.

TABLE 9

| | C. tropicalis gDNA titration_300 nM HEX | | | | | | |
|---|---|---|---|---|---|---|---|
| copies/rx | Cp1 | Cp2 | Cp3 | Cp4 | Average | Std Cp | CV |
| 10,000 | 25.41 | 25.03 | 24.99 | 25.26 | 25.17 | 0.20 | 0.8% |
| 1,000 | 28.79 | 28.72 | 28.82 | 28.69 | 28.76 | 0.06 | 0.2% |
| 100 | 32.21 | 32.23 | 32.25 | 32.32 | 32.25 | 0.05 | 0.1% |
| 10 | 35.11 | 35 | 34.96 | 35.38 | 35.11 | 0.19 | 0.5% |
| no template | | | | | ND | ND | ND |
| amplification efficiency | 2.00 | | | | | | |
| PCR efficiency | 100% | | | | | | |

Next, a similar assay was performed using a Candida tropicalis lysate rather than genomic DNA. A titration was performed with 100 ul of a Candida lysate prepared with different concentrations of C. tropicalis cells. Real-time PCR data are provided below (Table 10) for PCR reactions containing *Candida* lysate having 0 to 1000 (i.e., 0, 10, 100, or 1,000) genomic equivalents of *Candida tropicalis* genomic DNA per reaction. As shown in Table 10 and FIG. 3E, *Candida tropicalis* was successfully detected using the *C. tropicalis* specific molecular beacon probe at all genomic equivalents prepared using a *Candida* lysate.

TABLE 10

| | | | *C. tropicalis* cell lysate 300 nM HEX | | | | | |
|---|---|---|---|---|---|---|---|---|
| genomic equivalent/rx | Log | Cp1 | Cp2 | Cp3 | Cp4 | Average | Std Cp | CV |
| 1,000 | 3.0 | 28.57 | 28.67 | 28.59 | 28.61 | 28.61 | 0.04 | 0.2% |
| 100 | 2.0 | 31.99 | 31.92 | 32.06 | 32.05 | 32.01 | 0.06 | 0.2% |
| 10 | 1.0 | 35.07 | 34.57 | 34.55 | 34.46 | 34.66 | 0.28 | 0.8% |
| no cell lysate | | | | | | ND | ND | ND |
| amplification efficiency | | 2.14 | | | | | | |
| PCR efficiency | | 114% | | | | | | |

Figure 4A:
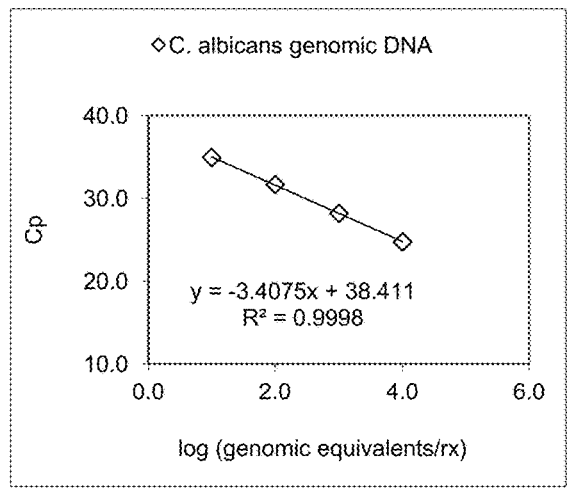
Figure 4A:
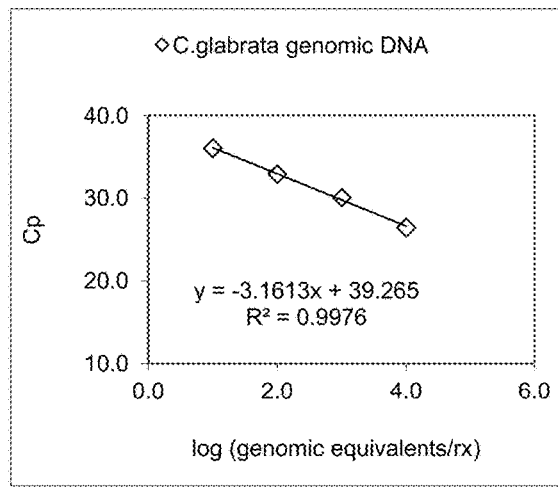

Example 4: Detection of *C. albicans* Using a Species-Specific Molecular Beacon Probe in a Real-Time PCR Assay A HEX labeled *C. albicans* probe (having the sequence of SEQ ID NO: 1) was used at 300 nM concentration in a real-time PCR assay that was performed according to the parameters described in Table 1 above. 100 μl of diluted genomic DNA was added to the PCR reaction mix and 45 cycles of amplification were performed with an annealing temperature of 60° C. A titration using different amounts of genomic DNA template was performed. Real-time PCR data are provided in Table 11 for reactions containing 0 to 10,000 copies (i.e., 0, 10, 100, 1,000, or 10,000) of genomic DNA per reaction. Four replicates for each reaction condition were performed and the average Ct values were calculated. The average amplification efficiency and the PCR efficiency for the reactions were also calculated. Table 11 and FIG. 4A show that the *C. albicans* molecular beacon probe was used successfully to detect the target nucleic acid molecule using genomic DNA isolated from *Candida albicans*.

TABLE 11

| | | | *C. albicans* genomic DNA | | | | | |
|---|---|---|---|---|---|---|---|---|
| copies/rx | Log | Cp1 | Cp2 | Cp3 | Cp4 | Average | Std Cp | CV |
| 10,000 | 4.0 | 24.57 | 24.71 | 24.7 | 25 | 24.75 | 0.18 | 0.7% |
| 1,000 | 3.0 | 28.01 | 28.15 | 28.19 | 28.45 | 28.20 | 0.18 | 0.7% |
| 100 | 2.0 | 31.59 | 31.63 | 31.65 | 31.86 | 31.68 | 0.12 | 0.4% |
| 10 | 1.0 | 34.86 | 34.14 | 35.02 | 35.75 | 34.94 | 0.66 | 1.9% |
| no template | | | | | | ND | ND | ND |
| amplification efficiency | | 1.97 | | | | | | |
| PCR efficiency | | 97% | | | | | | |

Figure 4C:
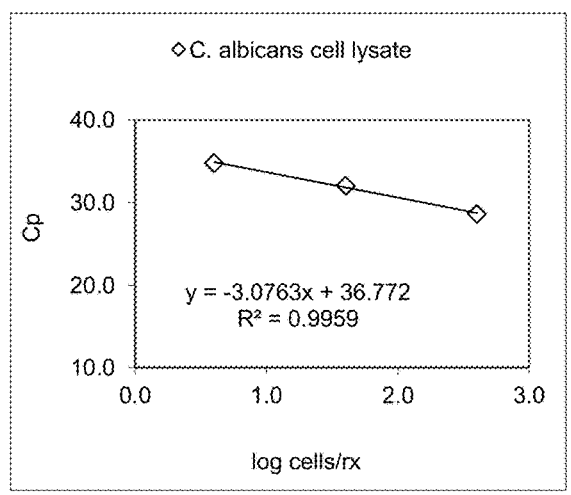

Next, a similar assay was performed using a *Candida albicans* lysate rather than genomic DNA. A titration was performed with 100 ul of a *Candida* lysate prepared with different concentrations of *C. albicans* cells. Real-time PCR data are provided below (Table 12) for PCR reactions containing *Candida* lysate which provide 0 to 400 (i.e., 0, 4, 40, or 400) genomic equivalents of *Candida albicans* genomic DNA per reaction. As shown in Table 12 and FIG. 4C, *Candida albicans* was successfully detected using the *C. albicans* specific molecular beacon probe at all genomic equivalents prepared using a *Candida* lysate.

TABLE 12

| | | | *C. albicans* cell lysate | | | | | |
|---|---|---|---|---|---|---|---|---|
| cells/rx | Log | Cp1 | Cp2 | Cp3 | Cp4 | Average | Std Cp | CV |
| 400 | 2.6 | 28.59 | 28.68 | 28.66 | 28.68 | 28.65 | 0.04 | 0.1% |
| 40 | 1.6 | 32.15 | 32.1 | 32.02 | 32.02 | 32.07 | 0.06 | 0.2% |
| 4 | 0.6 | 34.84 | 34.86 | 34.66 | 34.86 | 34.81 | 0.10 | 0.3% |
| no cell lysate | | | | 16.27 | | 16.27 | ND | ND |
| amplification efficiency | | 2.11 | | | | | | |
| PCR efficiency | | 111% | | | | | | |

Example 5: Detection of *C. glabrata* Using a Species-Specific Molecular Beacon Probe in a Real-Time PCR Assay A HEX labeled *C. glabrata* probe (having the sequence of SEQ ID NO: 3) was used at 300 nM concentration in a real-time PCR-assay that was performed according to the parameters described in Table 1 above. 100 μl of diluted genomic DNA was added to the PCR reaction mix and 45 cycles of amplification were performed with an annealing temperature of 60° C. A titration using different amounts of genomic DNA template was performed. Real-time PCR data are provided in Table 13 for reactions containing 0 to 10,000 (i.e., 0, 10, 100, 1,000, or 10,000) copies of genomic DNA per reaction. Four replicates for each reaction condition were performed and the average Ct values were calculated. The average amplification efficiency and the PCR efficiency for the reactions were also calculated. Table 13 and FIG. 4B show that the *C. glabrata* molecular beacon probe was used successfully to detect the target nucleic acid molecule using genomic DNA isolated from *Candida glabrata*.

TABLE 13

| | | | *C. glabrata* genomic DNA | | | | | |
|---|---|---|---|---|---|---|---|---|
| copies/rx | Log | Cp1 | Cp2 | Cp3 | Cp4 | Average | Std Cp | CV |
| 10,000 | 4.0 | 26.55 | 26.38 | 26.38 | 26.46 | 26.44 | 0.08 | 0.3% |
| 1,000 | 3.0 | 30.02 | 30.05 | 30.02 | 30.18 | 30.07 | 0.08 | 0.3% |
| 100 | 2.0 | 33.02 | 32.97 | 32.78 | 32.84 | 32.90 | 0.11 | 0.3% |
| 10 | 1.0 | 36.47 | 34.22 | 36.73 | 36.72 | 36.04 | 1.22 | 3.4% |
| no template | | | | | | ND | ND | ND |
| amplification efficiency | | 2.07 | | | | | | |
| PCR efficiency | | 107% | | | | | | |

Figure 4D:
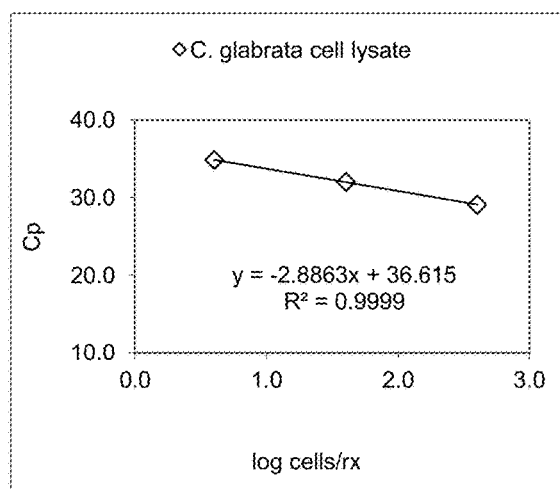
Figure 5A:
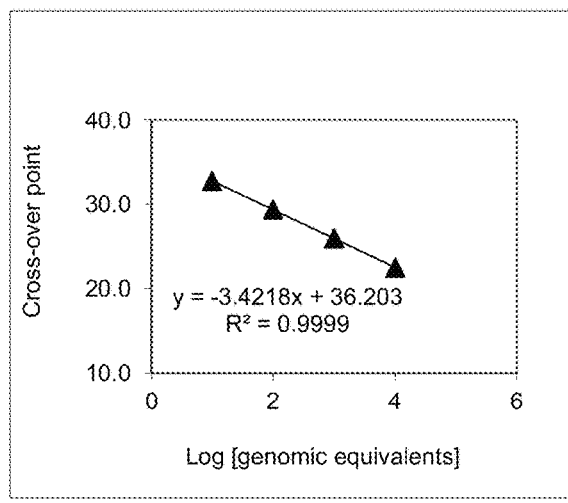
FIGS. 5A-5D are graphs showing the use of multiple molecular beacon probes in a multiplex assay to detect one or more *Candida* species in a sample. In this case, the genomic DNA of *Candida parapsilosis* and *Candida tropicalis* are present in a single reaction and amplified in the presence of a single beacon (FIGS. 5A and 5C, SEQ ID NO: 4 and SEQ ID NO: 2, respectively labeled with FAM and HEX) or with both beacons within the same reaction and emissions are observed in parallel using two channels (FIG. 5B and FIG. 5D).
Figure 5B:
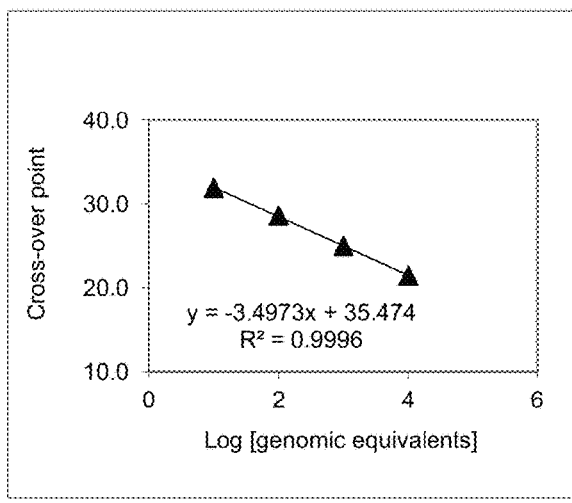
Figure 5C:
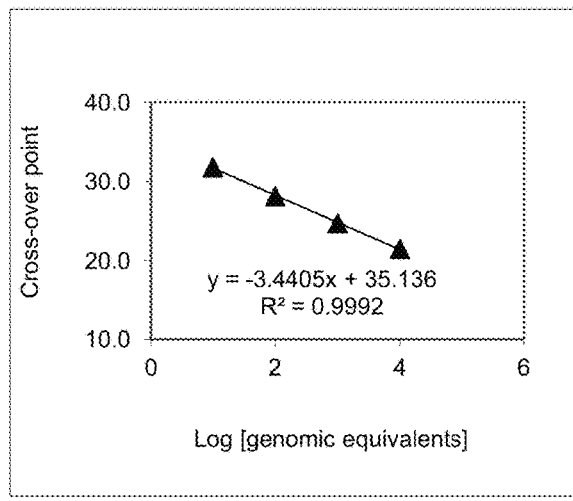
Figure 5D:
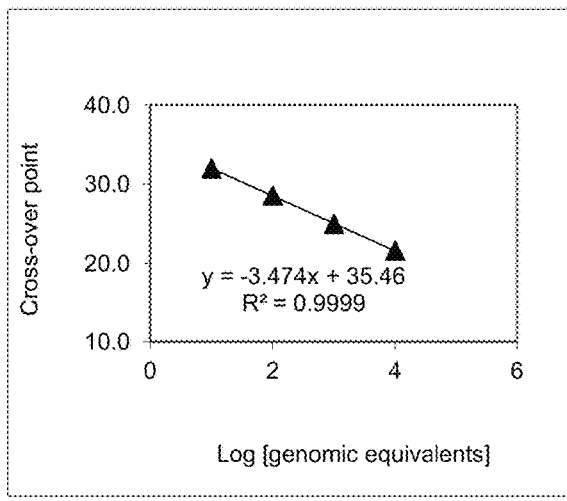

Next, a similar assay was performed using a *Candida glabrata* lysate rather than genomic DNA. A titration was performed with 100 ul of a *Candida* lysate prepared with different concentrations of *C. glabrata* cells. Real-time PCR data are provided below (Table 14) for PCR reactions containing *Candida* lysate which provide 0 to 400 (i.e., 0, 4, 40, or 400) genomic equivalents of *Candida glabrata* genomic DNA per reaction. As shown in Table 14 and FIG. 4D, *Candida glabrata* was successfully detected using the *C. glabrata* specific molecular beacon probe at all genomic equivalents prepared using a *Candida* lysate.

TABLE 14

| cells/rx | Log | Cp1 | Cp2 | Cp3 | Cp4 | Average | Std Cp | CV |
|---|---|---|---|---|---|---|---|---|
| C. glabrata cell lysate | | | | | | | | |
| 400 | 2.6 | 29 | 29.15 | 29.24 | 28.95 | 29.09 | 0.13 | 0.5% |
| 40 | 1.6 | 32.07 | 32.11 | 31.92 | 32.02 | 32.03 | 0.08 | 0.3% |
| 4 | 0.6 | 35.09 | 34.8 | 34.7 | 34.84 | 34.86 | 0.17 | 0.5% |
| no cell lysate | | | | | | ND | ND | ND |
| amplification efficiency | | 2.22 | | | | | | |
| PCR efficiency | | 122% | | | | | | |

The above data in Tables 4 to 14 and in FIGS. 3 and 4 demonstrate that each of the species specific probes can be used to successfully detect specific *Candida* species using either purified genomic DNA as an input in a real-time PCR assay or, alternatively, using a fungal cell lysate as an input in the assay.

Example 6: Multiplexed Real-Time PCR Assay for Detecting Multiple *Candida* Species in a Sample For a multiplexed molecular beacon assays, 300 nM of each species-specific beacon probe (0.3 uL per 100 uL reaction) were added to the PCR master mix. The *C. parapsilosis* and *C. tropicalis* molecular beacons (SEQ ID NO: 4 and SEQ ID NO; 2, respectively) are labeled with a FAM and a HEX fluor, respectively. The beacons are multiplexed in the reaction and detected in their respective channels (488-533 nm for FAM) and (488-610 for HEX). To ensure that the amplification efficiencies were similar between reactions containing a single beacon and reactions containing multiplexed beacons, *C. tropicalis* and *C. parapsilosis* genomic DNA was titrated into reactions at concentrations spanning 1E4 down to 10 copies per 20 uL reaction volume. These reactions included either a single beacon for detection (shown in Table 15 for *C. parapsilosis* and Table 17 for *C. tropicalis*) or the two beacons in the same reaction but detected with different channels (Table 16 and Table 18). In both cases the amplification effiencies were similar for both the single detection reactions and multiplexed detection reactions with no measurable impact on detection sensitivity. Thus, both *C. tropicalis* and *C. parapsilosis* can be detected within a single PCR reaction and potentially all five beacons could be multiplexed in a single reaction enabling detection of the five most clinically relevant *Candida* species within the same well.

TABLE 15

| Channel copies/rx | 483-533 | C. parapsilosis detection single beacon | | | | | |
|---|---|---|---|---|---|---|---|
| rx | Log | Cp1 | Cp2 | Cp3 | Average | Std Cp | CV |
| 10000 | 4 | 21.58 | 21.53 | 21.5 | 21.53667 | 0.040415 | 0.2% |
| 1000 | 3 | 25.01 | 24.96 | 24.97 | 24.98 | 0.026458 | 0.1% |
| 100 | 2 | 28.59 | 28.64 | 28.58 | 28.60333 | 0.032146 | 0.1% |
| 10 | 1 | 31.89 | 31.81 | 32 | 31.9 | 0.095394 | 0.3% |
| no template | | | | | ND | | |
| amplification efficiency = | | 1.9 | | | | | |
| PCR efficiency = | | 93.2% | | | | | |

TABLE 16

| Channel | 483-533 | C. parapsilosis detection mulitplexed reaction | | | | | |
|---|---|---|---|---|---|---|---|
| copies/rx | Log | Cp1 | Cp2 | Cp3 | Average | Std Cp | CV |
| 10000 | 4 | 22.61 | 22.51 | 22.48 | 22.53333 | 0.068069 | 0.3% |
| 1000 | 3 | 26.01 | 25.96 | | 25.985 | 0.035355 | 0.1% |
| 100 | 2 | 29.55 | 29.29 | 29.28 | 29.37333 | 0.15308 | 0.5% |
| 10 | 1 | 32.62 | 32.67 | 32.98 | 32.75667 | 0.195021 | 0.6% |
| no template | | | | | ND | | |
| amplification efficiency = | | 1.96 | | | | | |
| PCR efficiency = | | 96.0% | | | | | |

TABLE 17

| Channel | 488-610 | C. tropicalis detection single beacon | | | | | |
|---|---|---|---|---|---|---|---|
| copies/rx | Log | Cp1 | Cp2 | Cp3 | Average | Std Cp | CV |
| 10000 | 4 | 21.44 | 21.47 | 21.59 | 21.5 | 0.079373 | 0.4% |
| 1000 | 3 | 24.63 | 24.77 | 24.67 | 24.69 | 0.072111 | 0.3% |
| 100 | 2 | 28.23 | 28.01 | 28.08 | 28.10667 | 0.112398 | 0.4% |
| 10 | 1 | 31.92 | 31.65 | 31.86 | 31.81 | 0.141774 | 0.4% |
| no template | | | | | ND | | |
| amplification efficiency = | | 1.95 | | | | | |
| PCR efficiency = | | 95.3% | | | | | |

TABLE 18

| Channel | 488-610 | C. tropicalis detection multiplexed reaction | | | | | |
|---|---|---|---|---|---|---|---|
| copies/rx | Log | Cp1 | Cp2 | Cp3 | Average | Std Cp | CV |
| 10000 | 4 | 21.55 | 21.57 | 21.55 | 21.55667 | 0.011547 | 0.1% |
| 1000 | 3 | 24.96 | 24.89 | 24.99 | 24.94667 | 0.051316 | 0.2% |
| 100 | 2 | 28.72 | 28.5 | 28.51 | 28.57667 | 0.124231 | 0.4% |
| 10 | 1 | 32.12 | 31.84 | 31.89 | 31.95 | 0.149332 | 0.5% |
| no template | | | | | ND | | |
| amplification efficiency = | | 1.94 | | | | | |
| PCR efficiency = | | 94.0% | | | | | |

Example 7: DNA Sequencing-Based Detection of *Candida* Species

Figure 7:
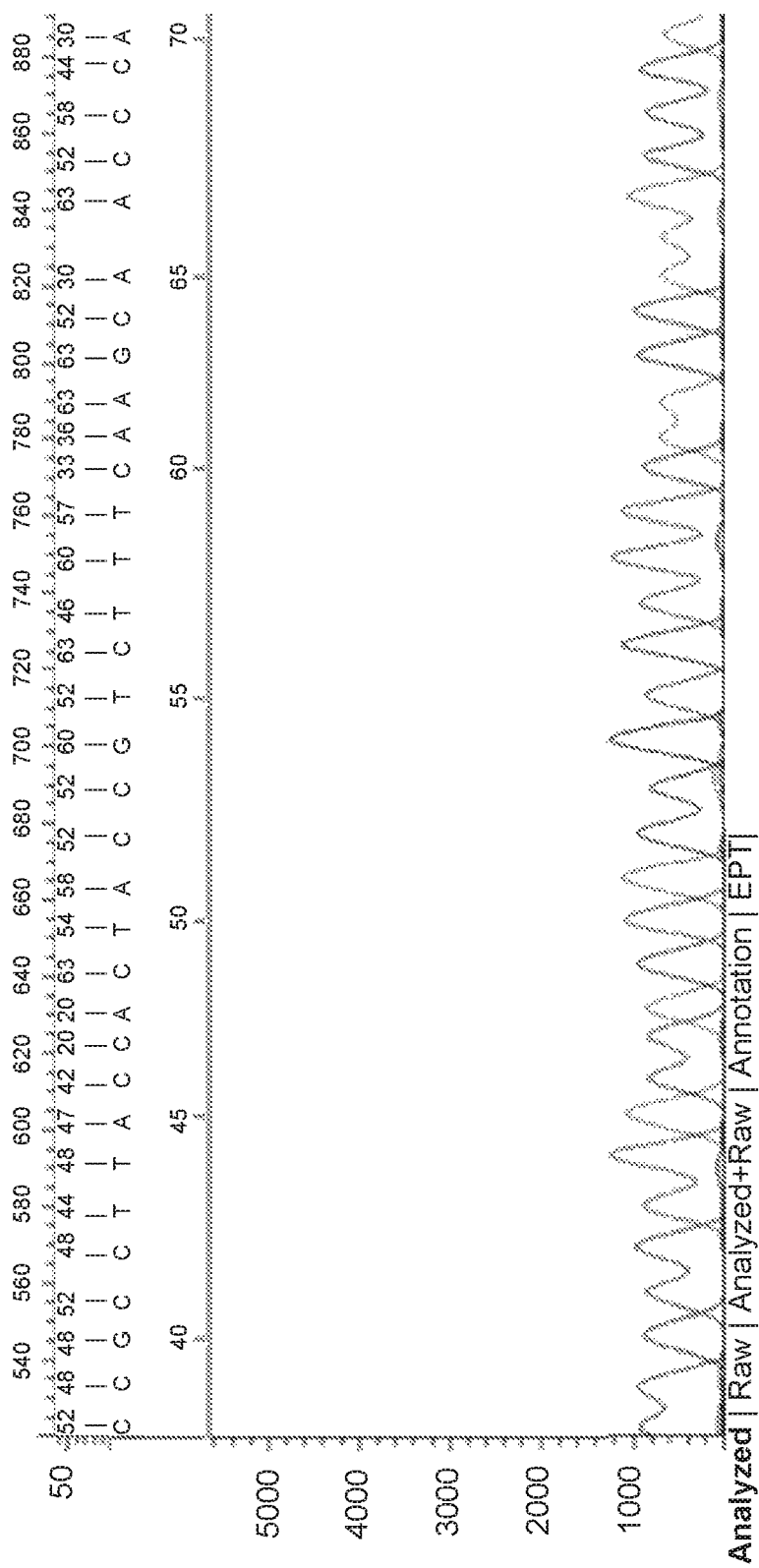
FIG. 7 is a sequence chromatogram generated from amplification within whole blood lysate using the pan-*Candida* forward and reverse primers (SEQ ID NOs: 11 and 12), followed by a phenol/chloroform extraction, a chloroform extraction, and then subsequentSanger Dideoxy terminator sequence analysis using Big Dye Vs.31. (Applied Biosystems, Foster City, Calif.).
Figure 7:
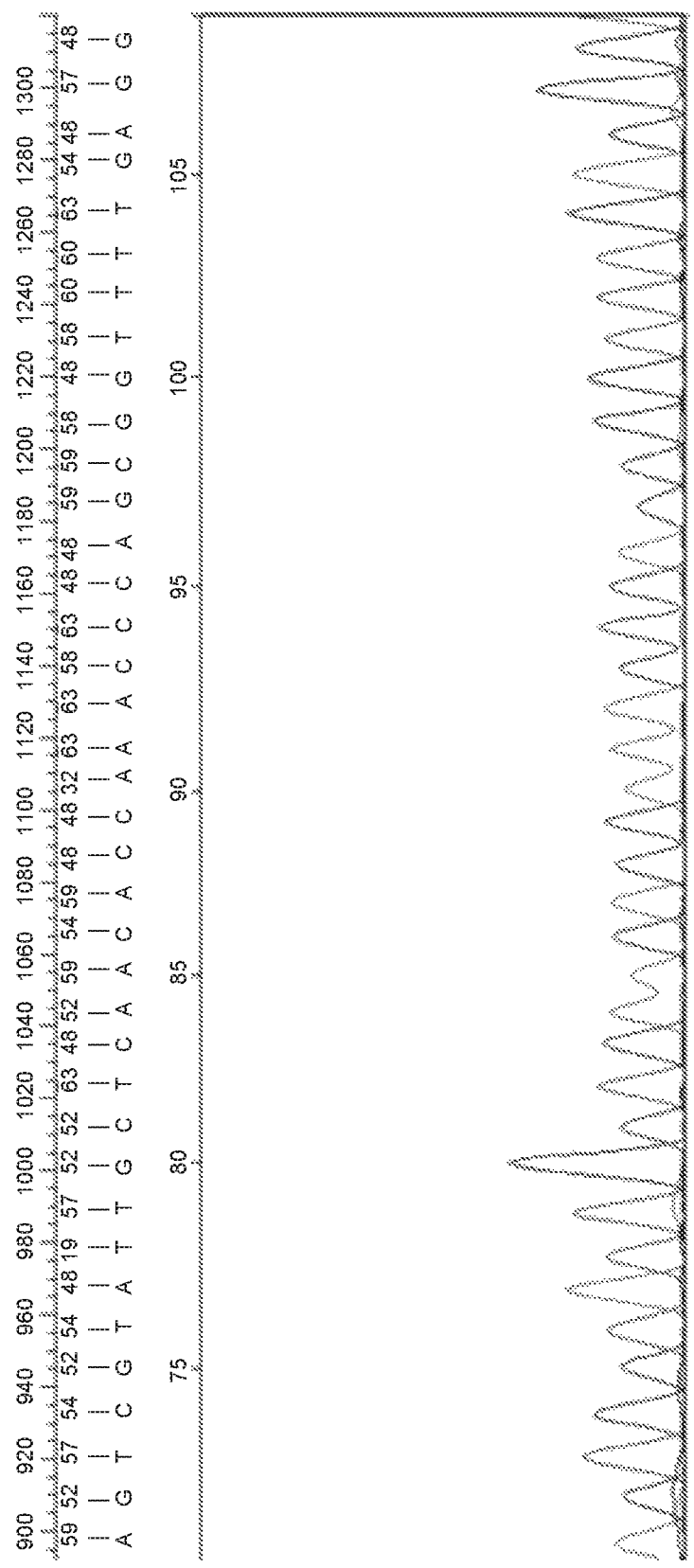

A probe having the sequence of SEQ ID NO: 32 (specific to *C. krusei*) was contacted with nucleic acid molecules that were amplified from within whole blood lysate using the pan-*Candida* forward and reverse primers (SEQ ID NOs: 11 and 12), followed by conducting a phenol/chloroform extraction, a chloroform extraction, and then conducting Sanger Dideoxy Sequencing using Big Dye Terminators on an AB 3730 capillary sequencing instrument. The resulting chromatogram, which is shown in FIG. 7, demonstrates that this method can also be used to of detect *Candida* species using the probes and primers of this invention.

The sequencing-based detection method described above can also be performed using a probe having the sequence of SEQ ID NO: 33 to detect *C. krusei*; a probe having the sequence of SEQ ID NO: 34 or 35 to detect *C. albicans*; a probe having the sequence of SEQ ID NO: 36 or 37 to detect *C. glabrata*; a probe having the sequence of SEQ ID NO: 38 or 39 to detect *C. parapsilosis*; or a probe having the sequence of SEQ ID NO: 40 or 41 to detect *C. tropicalis*.

Example 8: Detection of *C. albicans* Using a Species-Specific Molecular Beacon Probe in a Real-Time PCR Assay A FAM labeled *C. albicans* probe (having the sequence of SEQ ID NO: 1) was used at 300 nM concentration in a real-time PCR assay that was performed according to the parameters described in Table 1 above. 100 µl of diluted genomic DNA was added to the PCR reaction mix and 45 cycles of amplification were performed with an annealing temperature of 60° C. A titration using different amounts of genomic DNA template was performed. Real-time PCR data are provided in Table 19 for reactions containing 0 to 50,000 copies (i.e., 0 (no template), 5, 50, 500, 5,000, or 50,000) of genomic DNA per reaction. Four replicates for each reaction condition were performed and the average Cp values were calculated. The average amplification efficiency (2.03) and the PCR efficiency (103%) for the reactions were also calculated. Table 19 shows that the *C. albicans* molecular beacon probe was used successfully to detect the target nucleic acid molecule using genomic DNA isolated from *C. albicans*.

TABLE 19

| | | | | | | | Std | |
|---|---|---|---|---|---|---|---|---|
| copies/rx | Log | Cp1 | Cp2 | Cp3 | Cp4 | Average | Cp | CV |
| 50000 | 5 | 21.71 | 21.86 | 21.9 | 21.9 | 21.84 | 0.09 | 0.4% |
| 5000 | 4 | 25.24 | 25.06 | 25.23 | 25.27 | 25.20 | 0.09 | 0.4% |
| 500 | 3 | 28.66 | 28.64 | 28.72 | 28.68 | 28.68 | 0.03 | 0.1% |
| 50 | 2 | 31.84 | 31.87 | 31.88 | 31.84 | 31.86 | 0.02 | 0.1% |
| 5 | 1 | 34.39 | 35 | 35 | 35 | 34.80 | 0.31 | 0.9% |

TABLE 19-continued

*C. albicans* detection in singleplex reactions

| copies/rx | Log | Cp1 | Cp2 | Cp3 | Cp4 | Average | Std Cp | CV |
|---|---|---|---|---|---|---|---|---|
| no template | | ND | ND | ND | ND | | | |
| slope | −3.2566 | | | | | | 0.31 | |
| amplification efficiency = | 2.03 | | | | | | | |
| PCR efficiency = | 103% | | | | | | | |

Next, a similar assay was performed using a *C. albicans* lysate rather than genomic DNA. To determine the ability of the molecular beacons to detect *Candida* within crude cell lysates, we prepared lysate from *Candida* cells spiked in 1× phosphate buffered saline (PBS) buffer. *Candida* cells were quantified using a Coulter counter and were spiked into PBS at concentrations ranging from ~520 cells/mL to ~3 cells/mL. The in-vitro spiked solutions were added to a 1 mL polypropylene tube containing 300 mg of yttrium stabilized zirconium oxide beads. The cells were harvested via centrifugation at 6000×G for 5 minutes and the supernatant was removed. 100 uL of 1×TE was added to the tubes and the tubes were subjected to bead beating, as described herein, by placement in a vortexer (Biospec bead beater) at maximum speed for 5 minutes. Fifty microliters of lysate was then transferred into an asymmetric PCR master mix containing the molecular beacon probe, as described in Example 1.

Figure 8A:
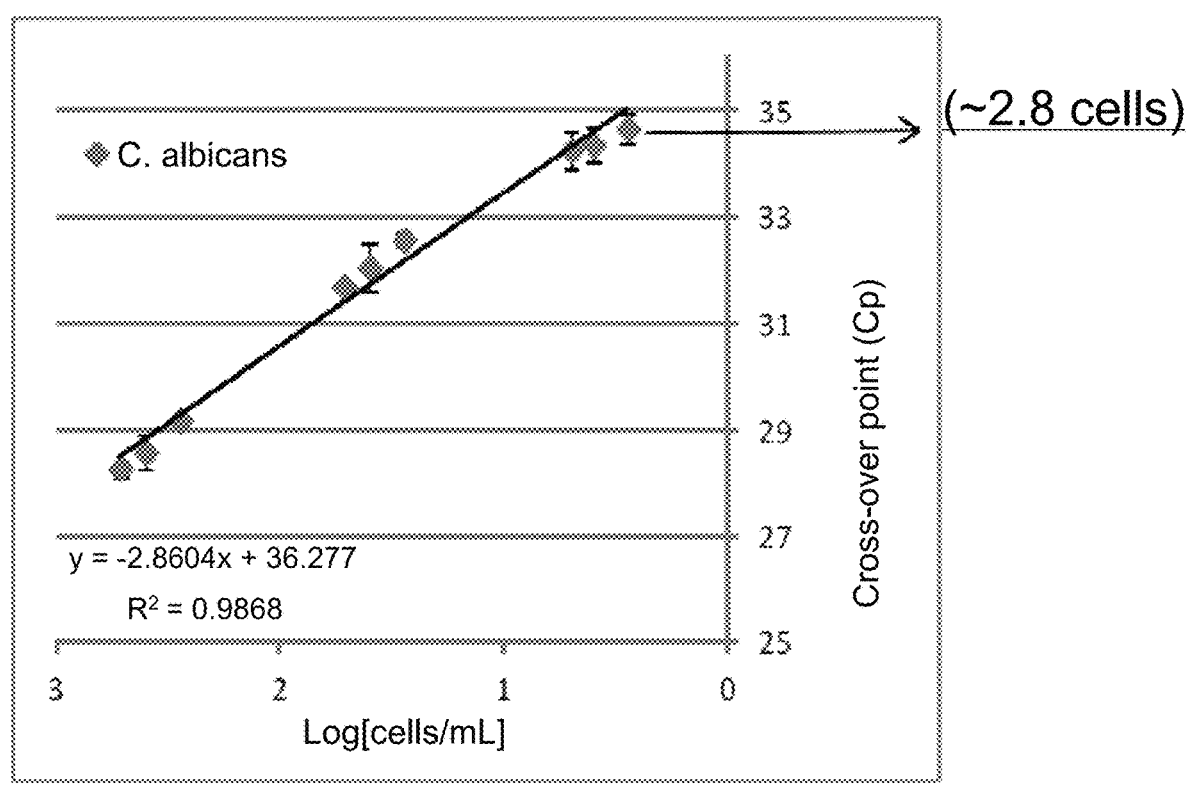
FIGS. 8A-8E are graphs of titration curves showing detection of *Candida albicans* (FIG. 8A), *Candida glabrata* (FIG. 8B), *Candida krusei* (FIG. 8C), *Candida parapsilosis* (FIG. 8D), and *Candida tropicalis* (FIG. 8E) in real-time PCR reactions using genomic DNA obtained from *Candida* cell lysates prepared with cells in an amount ranging from ~520 cells to ~3 cells/mL (see the data in Tables 20, 22, 24, 26, and 28, which was used to produce the graphs of FIGS. 8A-8E, respectively).

Real-time PCR data are provided below (Table 20) for PCR reactions containing *C. albicans* genomic DNA prepared from *C. albicans* lysate using the indicated number of cells/mL. The reactions were set up using lysates prepared over multiple days not the same sample lysate detected over multiple days, thus the variation in the entire process is shown. As shown in Table 20 and FIG. 8A, *C. albicans* was successfully detected using the *C. albicans* specific molecular beacon probe, and semi-quantitative detection of *C. albicans* was possible using as few as ~3 cells/mL.

TABLE 20

| | | *C. albicans* cells/mL | | | | | | | | |
|---|---|---|---|---|---|---|---|---|---|---|
| | | 520 | 400 | 280 | 52 | 40 | 28 | 5.2 | 4 | 2.8 | |
| operator | date | 2.716003 | 2.6021 | 2.44716 | 1.716 | 1.6021 | 1.4472 | 0.699 | 0.6021 | 0.44715803 | 0 |
| NP | May 1, 2012 | | 28.47 | | | 32.83 | | | | | ND |
| | | | 28.45 | | | 32.95 | | | | | ND |
| | | | 28.45 | | | 32.89 | | | | | ND |
| | | | 28.47 | | | 32.86 | | | | | ND |
| NP | Mar. 20, 2012 | | 28.59 | | | 32.15 | | | 34.84 | | ND |
| | | | 28.68 | | | 32.1 | | | 34.86 | | ND |
| | | | 28.66 | | | 32.02 | | | 34.66 | | ND |
| | | | 28.68 | | | 32.02 | | | 34.86 | | ND |
| NP | Mar. 30, 2012 | 28.36 | 28.75 | 29.15 | 31.64 | 31.81 | 32.42 | | 34.03 | 34.66 | ND |
| | | 28.35 | 28.79 | 29.18 | 31.67 | 31.73 | 32.44 | 34.03 | 33.76 | 34.77 | ND |
| | | 28.45 | 28.77 | 29.24 | 31.64 | 31.78 | 32.5 | 34.12 | 34.09 | | ND |
| | | 28.29 | 28.7 | | 31.9 | 31.79 | | 33.97 | 34.18 | | ND |
| NP | Mar. 28, 2012 | 28.48 | 28.77 | 29.15 | 31.83 | 31.8 | 32.69 | 34.88 | 34.54 | 34.99 | ND |
| | | 28.5 | 28.8 | 29.16 | 31.62 | 31.68 | 32.66 | 34.57 | 34.21 | 34.94 | ND |
| | | 28.32 | 28.78 | 29.16 | 31.56 | 31.7 | 32.44 | 34.77 | 34.53 | 34.9 | ND |
| | | 28.28 | 28.78 | 29.15 | 31.71 | 31.73 | 32.78 | 34.32 | 34.55 | 34.81 | ND |
| NP | Apr. 19, 2012 | 28.14 | 28.65 | 29.25 | 31.8 | 31.75 | 32.59 | 34.08 | 34.18 | 34.29 | ND |
| | | 28.12 | 28.57 | 29.28 | 31.75 | 31.84 | 32.63 | 33.98 | 34.03 | 34.42 | ND |
| | | 28.03 | 27.24 | 29.25 | 31.58 | 31.64 | 32.58 | 33.9 | 34.23 | 34.55 | ND |
| | | 28.11 | 28.64 | 29.21 | 31.61 | 31.72 | 32.49 | | 34.23 | 34.31 | ND |
| | mean | 28.28583 | 28.585 | 29.1982 | 31.693 | 32.04 | 32.565 | 34.262 | 34.361 | 34.664 | |
| | sd | 0.155649 | 0.3384 | 0.04916 | 0.1068 | 0.4547 | 0.1175 | 0.3561 | 0.3356 | 0.26000855 | |
| | cv | 0.55% | 1.18% | 0.17% | 0.34% | 1.42% | 0.36% | 1.04% | 0.98% | 0.75% | |

The above data demonstrate that the *C. albicans* molecular beacon probe can be used to successfully detect *C. albican* using either purified genomic DNA as an input in a real-time PCR assay or, alternatively, using a fungal cell lysate as an input in the assay.

Example 9: Detection of *C. glabrata* Using a Species-Specific Molecular Beacon Probe in a Real-Time PCR Assay A HEX labeled *C. glabrata* probe (having the sequence of SEQ ID NO: 3) was used at 300 nM concentration in a real-time PCR assay that was performed according to the parameters described in Table 1 above. 100 µl of diluted genomic DNA was added to the PCR reaction mix and 45 cycles of amplification were performed with an annealing temperature of 60° C. A titration using different amounts of genomic DNA template was performed. Real-time PCR data are provided in Table 21 for reactions containing 0 to 50,000 copies (i.e., 0 (no template), 5, 50, 500, 5,000, or 50,000) of genomic DNA per reaction. Four replicates for each reaction condition were performed and the average Cp values were calculated. The average amplification efficiency (2.23) and the PCR efficiency (123%) for the reactions were also calculated. Table 21 shows that the *C. glabrata* molecular beacon probe was used successfully to detect the target nucleic acid molecule using genomic DNA isolated from *C. glabrata*.

TABLE 21

*C. glabrata* detection in singleplex reactions

| copies/rx | Log | Cp1 | Cp2 | Cp3 | Cp4 | Average | Std Cp | CV |
|---|---|---|---|---|---|---|---|---|
| 50000 | 5 | 23.72 | 23.78 | 23.68 | 23.71 | 23.72 | 0.04 | 0.2% |
| 5000 | 4 | 27.1 | 27.18 | 27.22 | 27.24 | 27.19 | 0.06 | 0.2% |
| 500 | 3 | 30.56 | 30.67 | 30.64 | 30.51 | 30.60 | 0.07 | 0.2% |
| 50 | 2 | 33.17 | 33.46 | 33.44 | 33.55 | 33.41 | 0.16 | 0.5% |
| 5 | 1 | 35 | 35 | 35 | 35 | 35.00 | 0.00 | 0.0% |
| no template | | ND | ND | ND | ND | | | |
| slope | −2.87 | | | | | | | |
| | 0.35 | | | | | | | |
| amplification efficiency = | 2.23 | | | | | | | |
| PCR efficiency = | 123% | | | | | | | |

Next, a similar assay was performed using a *C. glabrata* lysate rather than genomic DNA according to the assay described in Example 8.

Figure 8B:
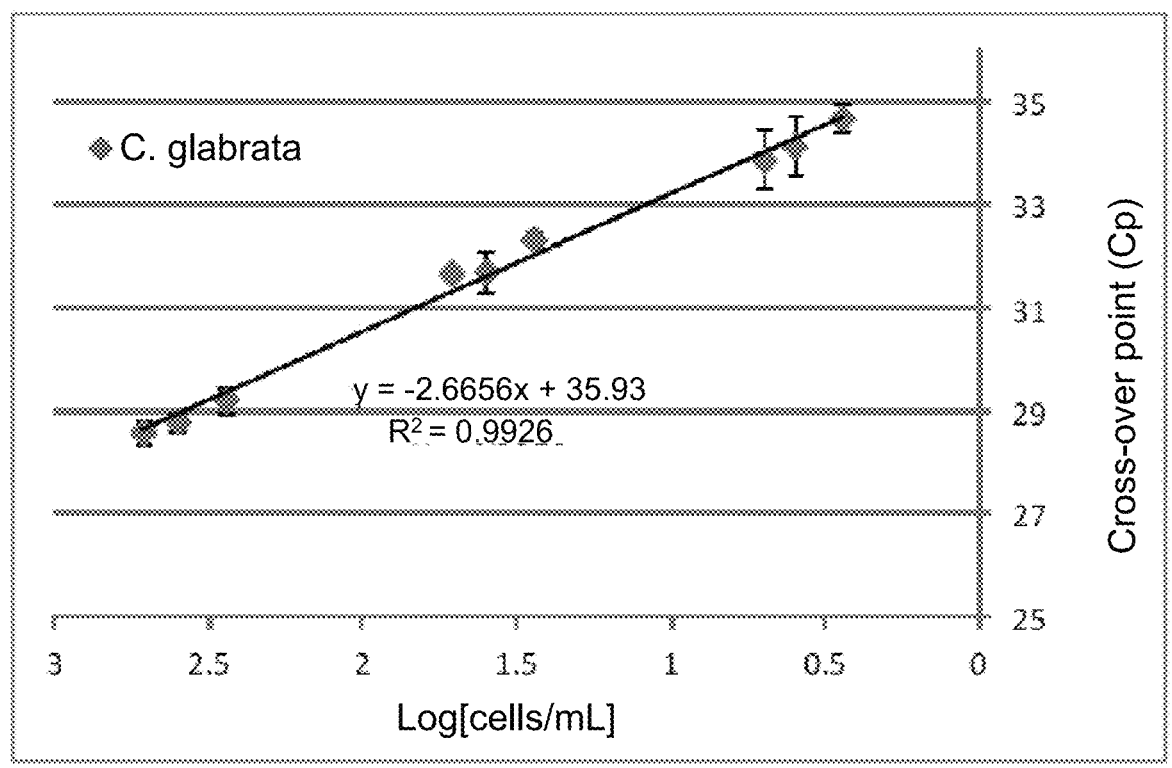

Real-time PCR data are provided below (Table 22) for PCR reactions containing *C. glabrata* genomic DNA prepared from *C. glabrata* lysate using the indicated number of cells/mL. The reactions were set up using lysates prepared over multiple days not the same sample lysate detected over multiple days, thus the variation in the entire process is shown. As shown in Table 22 and FIG. 8B, *C. glabrata* was successfully detected using the *C. glabrata* specific molecular beacon probe, and semi-quantitative detection of *C. glabrata* was possible using as few as ~3 cells/mL.

TABLE 22

| | | *C. glabrata* cells/mL | | | | | | | | |
|---|---|---|---|---|---|---|---|---|---|---|
| | | 520 | 400 | 280 | 52 | 40 | 28 | 5.2 | 4 | 2.8 | |
| operato | date | 2.716003 | 2.60206 | 2.447158 | 1.716003 | 1.60205 | 1.447158 | 0.69897 | 0.60206 | 0.447158 | 0 |
| NP | Mar. 29, 2012 | 28.45 | 28.75 | 29.05 | 31.77 | 31.91 | 32.39 | 34.27 | 34.53 | 34.71 | ND |
| | | 28.55 | 28.76 | 28.94 | 81.86 | 31.95 | 32.39 | 34.07 | 34.54 | 34.97 | ND |
| | | 28.3 | 28.59 | 29.09 | | 31.98 | 32.31 | 34.08 | 34.67 | 34.86 | ND |
| | | 28.51 | | 29.68 | 31.85 | | 32.58 | | | 34.81 | ND |
| | | 28.93 | 29.05 | 29.44 | 31.57 | 31 | 32.23 | 32.76 | 33.45 | 34.24 | ND |
| | | 28.82 | 28.95 | 29.35 | 31.59 | 31.68 | 32.46 | 33.92 | 33.65 | 34.94 | ND |
| | | 28.83 | 28.91 | 29.29 | 31.54 | 31.95 | 32.17 | 34.27 | | 34.38 | ND |
| NP | May 10, 2012 | | 29.86 | | | 32.83 | | | | | ND |
| | | | 29.25 | | | 32.95 | | | | | ND |
| | | | 29.75 | | | 32.89 | | | | | ND |
| | | | 29.74 | | | 32.86 | | | | | ND |
| CW | May 10, 2012 | | 29.65 | | | 32.98 | | | | | ND |
| | | | 29.75 | | | 32.88 | | | | | ND |
| | | | 29.79 | | | 33.03 | | | | | ND |
| | | | 29.74 | | | 33.06 | | | | | ND |
| NP | Mar. 20, 2012 | | 28.69 | | | 35.19 | | | 35.19 | | ND |
| | | | 28.81 | | | 32.18 | | | 35.42 | | ND |
| | | | 28.84 | | | 32.55 | | | 35.24 | | ND |
| | mean | 28.62571 | 28.83667 | 29.26286 | 31.71333 | 31.745 | 32.36143 | 33.895 | 34.168 | 34.70143 | |
| | sd | 0.231722 | 0.168721 | 0.255976 | 0.137502 | 0.380986 | 0.138856 | 0.57183 | 0.571244 | 0.283515 | |
| | cv | 0.81% | 0.59% | 0.87% | 0.43% | 1.20% | 0.43% | 1.69% | 1.67% | 0.82% | |

The above data demonstrate that the *C. glabrata* molecular beacon probe can be used to successfully detect *C. glabrata* using either purified genomic DNA as an input in a real-time PCR assay or, alternatively, using a fungal cell lysate as an input in the assay.

Example 10: Detection of *C. krusei* Using a Species-Specific Molecular Beacon Probe in a Real-Time PCR Assay A HEX labeled *C. krusei* probe (having the sequence of SEQ ID NO: 6) was used at 300 nM concentration in a real-time PCR assay that was performed according to the parameters described in Table 1 above. 100 µl of diluted genomic DNA was added to the PCR reaction mix and 45 cycles of amplification were performed with an annealing temperature of 60° C. A titration using different amounts of genomic DNA template was performed. Real-time PCR data are provided in Table 23 for reactions containing 0 to 50,000 copies (i.e., 0 (no template), 5, 50, 500, 5,000, or 50,000) of genomic DNA per reaction. Four replicates for each reaction condition were performed and the average Cp values were calculated. The average amplification efficiency (2.05) and the PCR efficiency (105%) for the reactions were also calculated. Table 23 shows that the *C. krusei* molecular beacon probe was used successfully to detect the target nucleic acid molecule using genomic DNA isolated from *C. krusei*.

TABLE 23

| | | | | | | | | |
|---|---|---|---|---|---|---|---|---|
| *C. krusei* detection in singleplex reactions | | | | | | | | |
| copies/rx | Log | Cp1 | Cp2 | Cp3 | Cp4 | Average | Std Cp | CV |
| 50000 | 5 | 22.17 | 22.3 | 22.15 | | 22.21 | 0.08 | 0.4% |
| 5000 | 4 | 25.77 | 25.86 | 25.75 | 25.85 | 25.81 | 0.06 | 0.2% |
| 500 | 3 | 29.15 | 29.03 | 29.21 | 29.2 | 29.15 | 0.08 | 0.3% |
| 50 | 2 | 32.17 | 32.25 | 32.2 | 32.34 | 32.24 | 0.07 | 0.2% |
| 5 | 1 | 35 | 35 | 35 | 35 | 35.00 | 0.00 | 0.0% |
| no template | | ND | ND | ND | ND | | | |
| slope | | −3.2019 0.31 | | | | | | |
| amplification efficiency = | | 2.05 | | | | | | |
| PCR efficiency = | | 105% | | | | | | |

Next, a similar assay was performed using a *C. krusei* lysate rather than genomic DNA according to the assay described in Example 8.

Figure 8C:
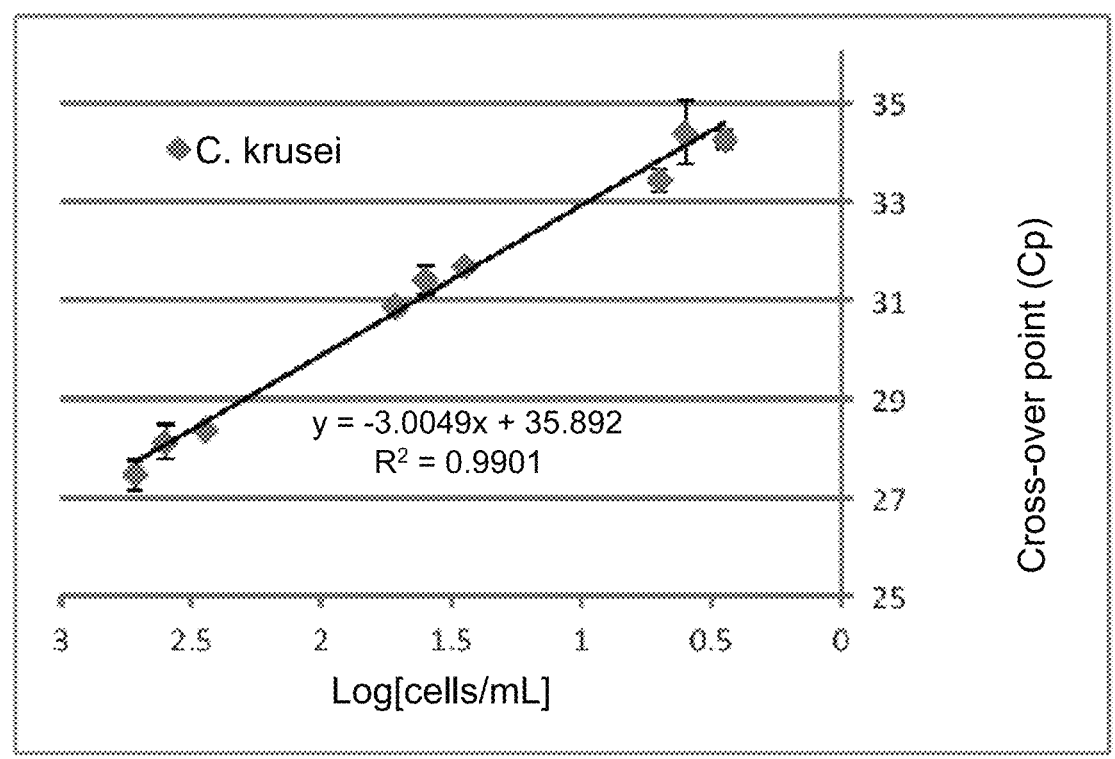

Real-time PCR data are provided below (Table 24) for PCR reactions containing *C. krusei* genomic DNA prepared from *C. krusei* lysate using the indicated number of cells/mL. The reactions were set up using lysates prepared over multiple days not the same sample lysate detected over multiple days, thus the variation in the entire process is shown. As shown in Table 24 and FIG. 8C, *C. krusei* was successfully detected using the *C. krusei* specific molecular beacon probe, and semi-quantitative detection of *C. krusei* was possible using as few as ~3 cells/mL.

TABLE 24

| | | *C. krusei* cell mL | | | | | | | | |
|---|---|---|---|---|---|---|---|---|---|---|
| operator | date | 520 2.716003 | 400 2.60206 | 280 2.447158 | 52 1.716003 | 40 1.60205 | 28 1.447158 | 5.2 0.69897 | 4 0.60206 | 2.8 0.447158 | 0 |
| NP | Mar. 21, 2012 | | 27.81 | | | 31.21 | | | 34.72 | | ND |
| | | | 27.59 | | | 31.1 | | | 34.88 | | ND |
| | | | 27.83 | | | 31.17 | | | 34.91 | | ND |
| | | | 27.77 | | | 13.12 | | | 34.94 | | ND |
| NP | Mar. 23, 2012 | | 28.71 | | | 31.9 | | | 34.81 | | ND |
| | | | 28.83 | | | 31.92 | | | 34.97 | | ND |
| | | | 28.75 | | | 31.85 | | | 34.88 | | ND |
| | | | 28.69 | | | 31.32 | | | 32.8 | | ND |
| NP | Mar. 30, 2012 | 27.85 | 28.01 | 28.43 | 31.19 | 31.53 | 31.67 | 33.47 | 34.34 | 34.28 | ND |
| | | 27.77 | 28.03 | 28.36 | 30.88 | 31.51 | 31.69 | 33.66 | 34.86 | 34.16 | ND |
| | | 27.84 | 27.96 | 28.36 | 30.84 | 31.51 | 31.74 | 33.2 | 34.59 | 34.43 | ND |
| | | 27.24 | 27.98 | | 30.82 | 31.26 | | | 33.95 | 34.34 | ND |
| | | 27.18 | 27.96 | | 30.76 | 31.25 | | | 33.92 | 34.13 | ND |
| | | 27.77 | 22.88 | | 30.85 | 31.46 | | | 33.69 | 33.96 | ND |
| | | 27.32 | 27.9 | | 30.79 | 31.24 | | | 33.78 | 34.5 | ND |
| NP | May 10, 2014 | | 28.2 | | | 31.75 | | | | | ND |
| | | | 28.22 | | | 31.72 | | | | | ND |
| | | | 28.2 | | | 31.74 | | | | | ND |
| | | | 28.35 | | | 31.75 | | | | | ND |
| CW | May 10, 2012 | | 28.48 | | | 31.59 | | | | | ND |
| | | | 28.45 | | | 31.73 | | | | | ND |
| | | | 28.37 | | | 31.7 | | | | | ND |
| | | | 28.56 | | | 31.6 | | | | | ND |
| NP | Mar. 20, 2012 | | 27.74 | | | 30.92 | | | 34.84 | | ND |
| | | | 27.82 | | | 31.07 | | | 34.72 | | ND |
| | | | 27.91 | | | 31.22 | | | 34.52 | | ND |
| | mean | 27.49571 | 28.14316 | 28.38333 | 30.87571 | 31.42333 | 31.7 | 33.44333 | 34.402667 | 34.25714 | |
| | sd | 0.307184 | 0.364662 | 0.040415 | 0.14409 | 0.279148 | 0.036056 | 0.231157 | 0.6403399 | 0.187146 | |
| | cv | 1.12% | 1.30% | 0.14% | 0.47% | 0.89% | 0.11% | 0.69% | 1.86% | 0.55% | |

The above data demonstrate that the *C. krusei* molecular beacon probe can be used to successfully detect *C. krusei* using either purified genomic DNA as an input in a real-time PCR assay or, alternatively, using a fungal cell lysate as an input in the assay.

Example 11: Detection of *C. parapsilosis* Using a Species-Specific Molecular Beacon Probe in a Real-Time PCR Assay A HEX labeled *C. parapsilosis* probe (having the sequence of SEQ ID NO: 5) was used at 300 nM concentration in a real-time PCR assay that was performed according to the parameters described in Table 1 above. 100 µl of diluted genomic DNA was added to the PCR reaction mix and 45 cycles of amplification were performed with an annealing temperature of 60° C. A titration using different amounts of genomic DNA template was performed. Real-time PCR data are provided in Table 25 for reactions containing 0 to 50,000 copies (i.e., 0 (no template), 5, 50, 500, 5,000, or 50,000) of genomic DNA per reaction. Four replicates for each reaction condition were performed and the average Cp values were calculated. The average amplification efficiency (2.10) and the PCR efficiency (110%) for the reactions were also calculated. Table 25 shows that the *C. parapsilosis* molecular beacon probe was used successfully to detect the target nucleic acid molecule using genomic DNA isolated from *Candida parapsilosis*.

TABLE 25

| | | *C. parapsilosis* detection in singleplex rx | | | | | | |
|---|---|---|---|---|---|---|---|---|
| copies/rx | Log | Cp1 | Cp2 | Cp3 | Cp4 | Average | Std Cp | CV |
| 50000 | 5 | 22.55 | 22.43 | 22.47 | 22.45 | 22.48 | 0.05 | 0.2% |
| 5000 | 4 | 25.91 | 25.85 | 25.9 | 25.72 | 25.85 | 0.09 | 0.3% |
| 500 | 3 | 29.2 | 29.2 | 29.25 | 29.25 | 29.23 | 0.03 | 0.1% |
| 50 | 2 | 32.13 | 32.16 | 32.15 | 32.31 | 32.19 | 0.08 | 0.3% |
| 5 | 1 | 35 | 35 | 34.53 | 35 | 34.84 | 0.24 | 0.7% |
| no template | | ND | ND | ND | ND | | | |
| slope | | −3.1079 | | | | | | |
| | | 0.32 | | | | | | |
| amplification efficiency = | | 2.10 | | | | | | |
| PCR efficiency = | | 110% | | | | | | |

Next, a similar assay was performed using a *C. parapsilosis* lysate rather than genomic DNA according to the assay described in Example 8.

Figure 8D:
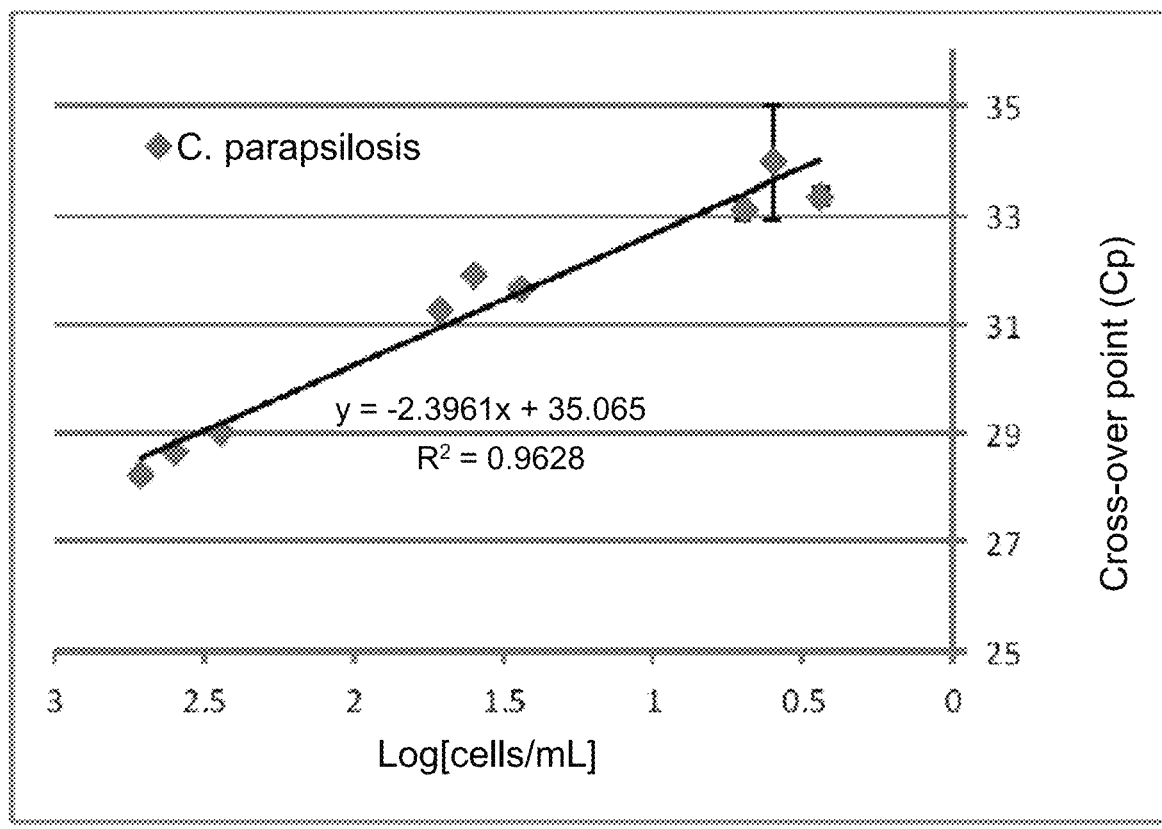

Real-time PCR data are provided below (Table 26) for PCR reactions containing *C. parapsilosis* genomic DNA prepared from *C. parapsilosis* lysate using the indicated number of cells/mL. The reactions were set up using lysates prepared over multiple days not the same sample lysate detected over multiple days, thus the variation in the entire process is shown. As shown in Table 26 and FIG. 8D, *C. parapsilosis* was successfully detected using the *C. parapsilosis* specific molecular beacon probe, and semi-quantitative detection of *C. parapsilosis* was possible using as few as ~3 cells/mL.

TABLE 26

| | | *C. parapsilosis* cells/ | | | | | | | | |
|---|---|---|---|---|---|---|---|---|---|---|
| operator | date | 520 2.716003 | 400 2.60206 | 280 2.447158 | 52 1.716003 | 40 1.60206 | 28 1.447158 | 5.2 0.69897 | 4 0.60206 | 2.8 0.447158 | 0 0 |
| NP | Mar. 23, 2012 | | 28.71 | | | 31.99 | | | 35.06 | | ND |
| | | | 28.71 | | | 31.93 | | | 34.89 | | ND |
| | | | 28.63 | | | 31.89 | | | 35.25 | | ND |
| NP | Apr. 2, 2012 | 28.3 | 28.59 | 29.02 | 31.3 | 31.36 | 31.67 | 33.37 | 33.27 | 33.49 | ND |
| | | 28.24 | 28.55 | 29.03 | 31.33 | 31.16 | 31.74 | 33.1 | 33.22 | 33.47 | ND |
| | | 28.28 | 28.6 | 29.05 | 31.32 | 31.23 | 31.65 | 33.17 | 33.19 | 33.17 | ND |
| | | 28.21 | 28.52 | 29.06 | 31.2 | 31.14 | 31.65 | 32.92 | 33.06 | 33.3 | ND |
| | | 28.05 | 28.28 | 28.8 | 29.49 | 30.75 | 29.88 | 29.11 | 32.18 | 32.01 | ND |
| | | 28.05 | 28.3 | 28.77 | 30.81 | 30.61 | 30.72 | 32.22 | 32.16 | 32.43 | ND |
| | | 28.06 | 28.16 | 28.88 | 30.86 | 30.53 | 31.25 | 31.64 | 32.03 | 31.47 | ND |
| NP | Apr. 30, 2012 | | 28.9 | | | 31.19 | | | | | ND |
| | | | 28.94 | | | 31.45 | | | | | ND |
| | | | 28.9 | | | 31.21 | | | | | ND |
| | | | 28.93 | | | 31.49 | | | | | ND |
| NP | May 11, 2012 | | 28.66 | | | 31.07 | | | | | ND |
| | | | 28.68 | | | 31.12 | | | | | ND |
| | | | 28.7 | | | 31.11 | | | | | ND |
| | | | 28.67 | | | 31.11 | | | | | ND |
| CW | May 11. 2012 | | 28.94 | | | 31.17 | | | | | ND |
| | | | 29.02 | | | 31.2 | | | | | ND |
| | | | 28.96 | | | 31.23 | | | | | ND |
| | | | 29.01 | | | 31.24 | | | | | ND |
| | mean | 28.2575 | 28.68333 | 29.04 | 31.2875 | 31.93667 | 31.6775 | 33.14 | 33.99143 | 33.3575 | |
| | sd | 0.040311 | 0.046188 | 0.018257 | 0.059652 | 0.050332 | 0.04272 | 0.186011 | 1.013138 | 0.1513 | |
| | cv | 0.14% | 0.16% | 0.06% | 0.19% | 0.16% | 0.13% | 0.56% | 2.98% | 0.45% | |

The above data demonstrate that the *C. parapsilosis* molecular beacon probe can be used to successfully detect *C. parapsilosis* using either purified genomic DNA as an input in a real-time PCR assay or, alternatively, using a fungal cell lysate as an input in the assay.

Example 12: Detection of *C. tropicalis* Using a Species-Specific Molecular Beacon Probe in a Real-Time PCR Assay A HEX labeled *C. tropicalis* probe (having the sequence of SEQ ID NO: 2) was used at 300 nM concentration in a real-time PCR assay that was performed according to the parameters described in Table 1 above. 100 µl of diluted genomic DNA was added to the PCR reaction mix and 45 cycles of amplification were performed with an annealing temperature of 60° C. A titration using different amounts of genomic DNA template was performed. Real-time PCR data are provided in Table 27 for reactions containing 0 to 50,000 copies (i.e., 0 (no template), 5, 50, 500, 5,000, or 50,000) of genomic DNA per reaction. Four replicates for each reaction condition were performed and the average Cp values were calculated. The average amplification efficiency (2.11) and the PCR efficiency (111%) for the reactions were also calculated. Table 27 shows that the *C. tropicalis* molecular beacon probe was used successfully to detect the target nucleic acid molecule using genomic DNA isolated from *C. tropicalis*.

TABLE 27

| | | | | | | | | |
|---|---|---|---|---|---|---|---|---|
| *C. tropicalis* detection in singleplex rx | | | | | | | | |
| copies/rx | Log | Cp1 | Cp2 | Cp3 | Cp4 | Average | Std Cp | CV |
| 50000 | 5 | 22.81 | 22.81 | 22.23 | 22.72 | 22.64 | 0.28 | 1.2% |
| 5000 | 4 | 26.23 | 26.08 | 26.23 | 26.13 | 26.17 | 0.08 | 0.3% |
| 500 | 3 | 29.35 | 29.37 | 29.31 | 29.31 | 29.34 | 0.03 | 0.1% |
| 50 | 2 | 32.59 | 32.26 | 32.14 | 32.34 | 32.33 | 0.19 | 0.6% |
| 5 | 1 | 35 | 35 | 35 | 35 | 35.00 | 0.00 | 0.0% |
| no template | | ND | ND | ND | ND | | | |
| slope | −3.09 | | | | | | | |
| | 0.32 | | | | | | | |
| amplification efficiency = | 2.11 | | | | | | | |
| PCR efficiency = | 111% | | | | | | | |

Next, a similar assay was performed using a *C. tropicalis* lysate rather than genomic DNA according to the assay described in Example 8.

Figure 8E:
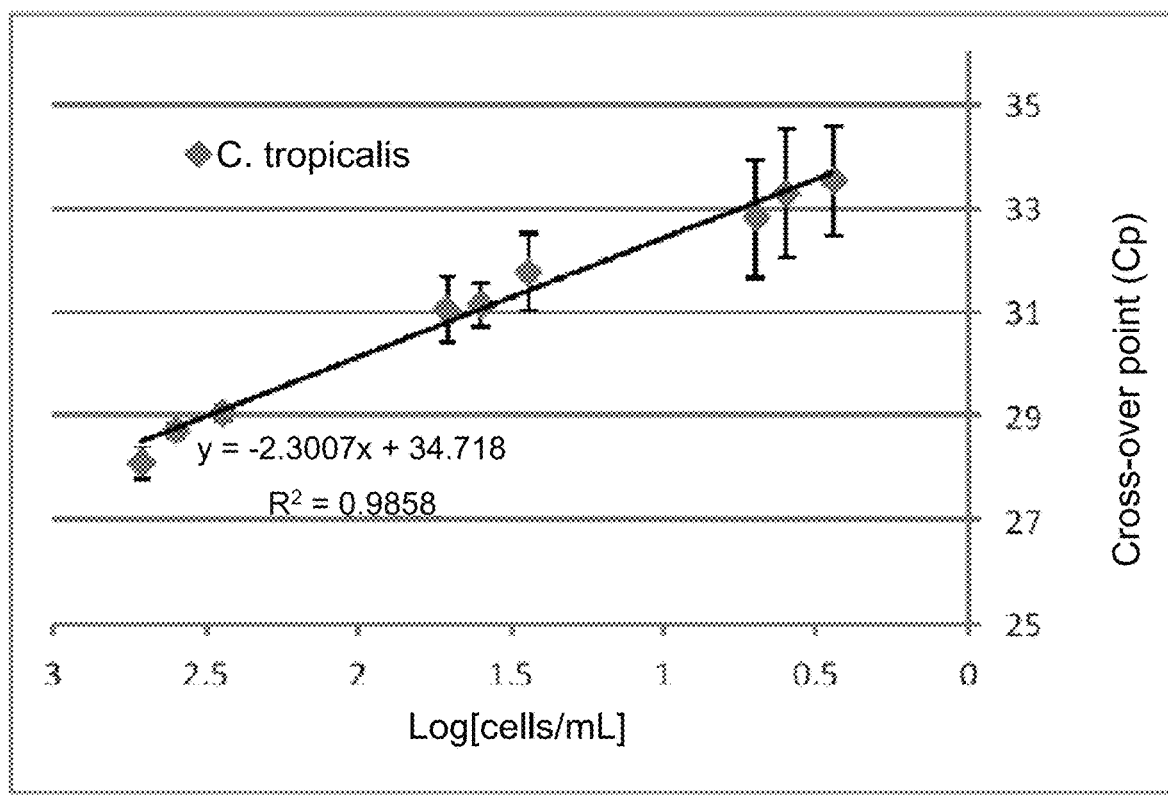

Real-time PCR data are provided below (Table 28) for PCR reactions containing *C. tropicalis* genomic DNA prepared from *C. tropicalis* lysate using the indicated number of cells/mL. The reactions were set up using lysates prepared over multiple days not the same sample lysate detected over multiple days, thus the variation in the entire process is shown. As shown in Table 28 and FIG. 8E, *C. tropicalis* was successfully detected using the *C. tropicalis* specific molecular beacon probe, and semi-quantitative detection of *C. tropicalis* was possible using as few as ~3 cells/mL.

TABLE 28

| | | | | | | | | | | | |
|---|---|---|---|---|---|---|---|---|---|---|---|
| | | *C. tropicalis* cells/mL | | | | | | | | | |
| operator | date | 520 2.716003 | 400 2.60206 | 280 2.447158 | 52 1.716003 | 40 1.60206 | 28 1.447158 | 5.2 0.69897 | 4 0.60206 | 2.8 0.447158 | 0 |
| NP | Apr. 30, 2012 | | 28.94 | | | 31.1 | | | | | ND |
| | | | 28.89 | | | 30.98 | | | | | ND |
| | | | 28.96 | | | 31.04 | | | | | ND |
| | | | 28.92 | | | 30.91 | | | | | ND |
| NP | Mar. 23, 2012 | | 28.71 | | | 31.9 | | | 34.81 | | ND |
| | | | 28.83 | | | 31.92 | | | 34.97 | | ND |
| | | | 28.75 | | | 31.85 | | | 34.88 | | ND |
| NP | Apr. 3, 2012 | | 28.69 | | | 31.32 | | | 32.8 | | ND |
| | | 28.36 | 28.72 | 29.15 | 31.64 | 31.28 | 32.42 | | 32.81 | 34.66 | ND |
| | | 28.35 | 28.65 | 29.18 | 31.67 | 31.42 | 32.44 | 34.03 | 32.68 | 34.77 | ND |
| | | 28.45 | 28.69 | 29.24 | 31.64 | 31.35 | 32.5 | 34.12 | 32.8 | | ND |
| NP | Apr. 4, 2012 | 27.87 | 28.58 | 28.88 | 30.49 | 30.53 | 31 | 32.22 | 32.04 | 32.73 | ND |
| | | 27.85 | 28.56 | 29.02 | 30.5 | 30.77 | 31.06 | 31.83 | 31.96 | 32.77 | ND |
| | | 27.82 | 28.54 | 28.99 | 30.43 | 30.67 | 31.24 | 31.99 | | 32.84 | ND |
| NP | May 11, 2012 | | 28.61 | | | 30.93 | | | | | ND |
| | | | 28.68 | | | 30.84 | | | | | ND |
| | | | 28.66 | | | 30.96 | | | | | ND |
| | | | 28.65 | | | 30.97 | | | | | ND |
| CW | May 11, 2012 | | 28.87 | | | 30.86 | | | | | ND |
| | | | 28.93 | | | 30.96 | | | | | ND |
| | | | 28.92 | | | 30.98 | | | | | ND |
| | | | 28.98 | | | 31.02 | | | | | ND |
| NP | Mar. 21, 2012 | | 28.57 | | | 31.99 | | | 35.07 | | ND |
| | | | 28.67 | | | 31.92 | | | 34.57 | | ND |
| | | | 28.59 | | | 32.06 | | | 34.55 | | ND |
| | | | 28.61 | | | 32.05 | | | 34.46 | | ND |
| | mean | 28.11667 | 28.73158 | 29.07667 | 31.06167 | 31.152222 | 31.77667 | 32.838 | 33.30556 | 33.554 | |
| | sd | 0.298239 | 0.132173 | 0.135745 | 0.645025 | 0.4114044 | 0.745913 | 1.138143 | 1.228455 | 1.061287 | |
| | cv | 1.06% | 0.46% | 0.47% | 2.08% | 1.32% | 2.35% | 3.47% | 3.69% | 3.16% | |

The above data demonstrate that the *C. tropicalis* molecular beacon probe can be used to successfully detect *C. tropicalis* using either purified genomic DNA as an input in a real-time PR assay or, alternatively, using a fungal cell lysate as an input in the assay.

Example 13: Detection of *Candida albicans* in a Multiplex Reaction with *Candida albicans*, *Candida Krusei*, and *Candida glabrata*

The molecular beacon probes can also be used to successfully detect *Candida* target nucleic acid molecules in a multiplexed reaction that includes nucleic acid molecules from two or more *Candida* species.

A multiplex reaction was performed using nucleic acid molecules (genomic DNA) from *C. albicans, C. krusei,* and *C. glabrata.* 300 nM of each *Candida* species-specific beacon probe (corresponding to SEQ ID NOs: 1, 6, and 3, respectively; 0.3 uL per 100 uL reaction) were used in a real-time PCR assay that was performed according to the parameters described in Table 1 above. The *C. albicans, C. krusei,* and *C. glabrata* molecular beacons are each labeled with spectrally distinguishable fluororphors that are detected in their respective channels. 100 μl of diluted genomic DNA was added to the PCR reaction mix and 45 cycles of amplification were performed with an annealing temperature of 60° C. A titration using different amounts of genomic DNA template was performed. Real-time PCR data are provided in Table 29 for reactions containing 0 to 50,000 copies (i.e., 0 (no template), 5, 50, 500, 5,000, or 50,000) of genomic DNA per reaction. Four replicates for each reaction condition were performed and the average Cp values were calculated. The average amplification efficiency (2.00) and the PCR efficiency (100%) for the reactions were also calculated. Table 29 shows that the *C. albicans* molecular beacon probe was used successfully to detect the *C. albicans* target nucleic acid molecules using genomic DNA isolated from *C. albicans*, even in the presence *C. krusei* and *C. glabrata* nucleic acid molecules, as well as molecular beacons for all of these *Candida* species. Notably, the amplification efficiency and PCR efficiency in the multiplex reaction was similar to that observed in the singleplex reaction (see Example 8 and Table 19). Thus, the limit of detection using the molecular beacon probes is not changing even when they are used in combination. Similarly, the presence of multiple probes in the sample is not affecting the efficiency of the nucleic acid amplification reaction.

TABLE 29

| | *C. albicans* detection in multiplex rx (*C. albicans*, *C. krusei*, and *C. glabrata* multiplex) | | | | | | |
|---|---|---|---|---|---|---|---|
| copies/rx | Cp1 | Cp2 | Cp3 | Cp4 | Average | Std Cp | CV |
| 50000 | 21.69 | 21.76 | 21.05 | 21.68 | 21.55 | 0.33 | 1.5% |
| 5000 | 25.1 | 25.14 | 25.08 | 25.02 | 25.09 | 0.05 | 0.2% |
| 500 | 28.7 | 28.55 | 28.51 | 28.52 | 28.57 | 0.09 | 0.3% |
| 50 | 31.68 | 31.77 | 31.92 | | 31.79 | 0.12 | 0.4% |
| 5 | 34.45 | 35 | 34.93 | 35 | 34.79 | 0.27 | 0.8% |
| no template | ND | ND | ND | ND | | | |
| slope | −3.32 | | | | | | |
| | 0.30 | | | | | | |
| amplification efficiency = | 2.00 | | | | | | |
| PCR efficiency = | 100% | | | | | | |

Example 14: Detection of *C. glabrata* in a Multiplex Reaction with *C. albicans, C. krusei,* and *C. glabrata*

A molecular beacon probe for *C. glabrata* (SEQ ID NO: 3) can be used to successfully detect *C. glabrata* nucleic acid molecules in a multiplex reaction that also includes nucleic acid molecules from *C. albicans* and *C. krusei*. The multiplex reaction was performed as described in Example 13. Real-time PCR data are provided in Table 30 for reactions containing 0 to 50,000 copies (i.e., 0 (no template), 5, 50, 500, 5,000, or 50,000) of genomic. DNA per reaction. Four replicates for each reaction condition were performed and the average Cp values were calculated. The average amplification efficiency (2.02) and the PCR efficiency (102%) for the reactions were also calculated. Table 30 shows that the *C. glabrata* molecular beacon probe was used successfully to detect *C. glabrata* target nucleic acid molecules using genomic DNA isolated from *C. glabrata*, even in the presence *C. albicans* and *C. krusei* nucleic acid molecules, as well as molecular beacons for all of these *Candida* species. Notably, the amplification efficiency and PCR efficiency in the multiplex reaction was similar to that observed in the singleplex reaction (see Example 9 and Table 21).

TABLE 30

| | *C. glabrata* detection in multiplex rx (*C. albicans*, *C. krusei*, and *C. glabrata* multiplex) | | | | | | |
|---|---|---|---|---|---|---|---|
| copies/rx | Cp1 | Cp2 | Cp3 | Cp4 | Average | Std Cp | CV |
| 50000 | 23.65 | 23.79 | 23.25 | 23.75 | 23.61 | 0.25 | 1.0% |
| 5000 | 27.08 | 27.12 | 26.92 | 27.03 | 27.04 | 0.09 | 0.3% |
| 500 | 30.55 | 30.49 | | 30.54 | 30.53 | 0.03 | 0.1% |
| 50 | 33.24 | 33.3 | 33.49 | 33.38 | 33.35 | 0.11 | 0.3% |
| 5 | | 35 | 35 | | 35.00 | 0.00 | 0.0% |
| no template | ND | ND | ND | ND | | | |
| slope | −3.27 | | | | | | |
| | 0.31 | | | | | | |
| amplification efficiency = | 2.02 | | | | | | |
| PCR efficiency = | 102% | | | | | | |

Example 15: Detection of *C. krusei* in a Multiplex Reaction with *C. albicans, C. krusei,* and *C. glabrata*

A molecular beacon probe for *Candida krusei* (SEQ ID NO: 6) can be used to successfully detect *C. krusei* nucleic acid molecules in a multiplex reaction that also includes nucleic acid molecules from *C. albicans* and *C. glabrata*. The multiplex reaction was performed as described in Example 13. Real-time PCR data are provided in Table 26 for reactions containing 0 to 50,000 copies (i.e., 0 (no template), 5, 50, 500, 5,000, or 50,000) of genomic DNA per reaction. Four replicates for each reaction condition were performed and the average Cp values were calculated. The average amplification efficiency (2.12) and the PCR efficiency (112%) for the reactions were also calculated. Table 31 shows that the *C. krusei* molecular beacon probe was used successfully to detect *C. krusei* target nucleic acid molecules using genomic DNA isolated from *C. krusei*, even in the presence *C. albicans* and *C. glabrata* nucleic acid molecules, as well as molecular beacons for all of these *Candida* species. Notably, the amplification efficiency and PCR efficiency in the multiplex reaction was similar to that observed in the singleplex reaction (see Example 10 and Table 23).

TABLE 31

C. krusei detection in multiplex rx (C. albicans, C. krusei, and C. glabrata multiplex)

| copies/rx | Cp1 | Cp2 | Cp3 | Cp4 | Average | Std Cp | CV |
|---|---|---|---|---|---|---|---|
| 50000 | 22.18 | 22.34 | 22.12 | 22.24 | 22.22 | 0.09 | 0.4% |
| 5000 | | 25.74 | 25.66 | 25.68 | 25.69 | 0.04 | 0.2% |
| 500 | 29.13 | 29.26 | 29.38 | 28.93 | 29.18 | 0.19 | 0.7% |
| 50 | 32.14 | 32.09 | 32.18 | 32.22 | 32.16 | 0.06 | 0.2% |
| 5 | 34.36 | 33.68 | 35 | 35 | 34.35 | 0.63 | 1.8% |
| no template | ND | ND | ND | ND | | | |
| slope | −3.07 | | | | | | |
| | 0.33 | | | | | | |
| | 2.12 | | | | | | |
| | 112% | | | | | | |

Example 16: Detection of C. parapsilosis in a Multiplex Reaction with C. parapsilosis and C. tropicalis A molecular beacon probe for *Candida parapsilosis* (SEQ ID NO: 4) can be used to successfully detect *C. parapsilosis* nucleic acid molecules in a multiplex reaction that also includes nucleic acid molecules from *C. tropicalis*. The multiplex reaction was performed using nucleic acid molecules (genomic DNA) from *C. parapsilosis* and *C. tropicalis*. 300 nM of each *Candida* species-specific beacon probe (corresponding to SEQ ID NOs: 4 and 2, respectively; 0.3 uL per 100 uL reaction) were used in a real-time PCR assay that was performed according to the parameters described in Table 1 above. 100 μl of diluted genomic DNA was added to the PCR reaction mix and 45 cycles of amplification were performed with an annealing temperature of 60° C. A titration using different amounts of genomic DNA template was performed. Real-time PCR data are provided in Table 32 for reactions containing 0 to 50,000 copies (i.e., 0 (no template), 5, 50, 500, 5,000, or 50,000) of genomic DNA per reaction. Four replicates for each reaction condition were performed and the average Cp values were calculated. The average amplification efficiency (2.07) and the PCR efficiency (107%) for the reactions were also calculated. Table 32 shows that the *C. parapsilosis* molecular beacon probe was used successfully to detect *C. parapsilosis* target nucleic acid molecules using genomic DNA isolated from *C. parapsilosis*, even in the presence *C. tropicalis* nucleic acid molecules, as well as molecular beacons for both of these *Candida* species. Notably, the amplification efficiency and PCR efficiency in the multiplex reaction was similar to that observed in the singleplex reaction (see Example 11 and Table 25).

TABLE 32

C. parapsilosis detection in multiplex rx (C. tropicalis, C. parpasilosis)

| copies/rx | Cp1 | Cp2 | Cp3 | Cp4 | Average | Std Cp | CV |
|---|---|---|---|---|---|---|---|
| 50000 | 22.03 | 22.33 | 22.47 | 22.47 | 22.33 | 0.21 | 0.9% |
| 5000 | 25.83 | 25.86 | 25.81 | 25.81 | 25.83 | 0.02 | 0.1% |
| 500 | 29.17 | 29.16 | 29.18 | 29.13 | 29.16 | 0.02 | 0.1% |
| 50 | 32.03 | 32.11 | 32.29 | 32.1 | 32.13 | 0.11 | 0.3% |
| 5 | 35 | 35 | 35 | 35 | 35.00 | 0.00 | 0.0% |
| no template | ND | ND | ND | ND | | | |
| slope | 3.17 | | | | | | |
| | 0.32 | | | | | | |
| | 2.07 | | | | | | |
| | 107% | | | | | | |

Example 17: Detection of C. tropicalis in a Multiplex Reaction with C. parapsilosis and C. tropicalis A molecular beacon probe for *C. tropicalis* (SEQ ID NO: 2) can be used to successfully detect *C. tropicalis* nucleic acid molecules in a multiplex reaction that also includes nucleic acid molecules from *C. parapsilosis*. The multiplex reaction was performed as described in Example 16. Real-time PCR data are provided in Table 33 for reactions containing 0 to 50,000 copies (i.e., 0 (no template), 5, 50, 500, 5,000, or 50,000) of genomic DNA per reaction. Four replicates for each reaction condition were performed and the average Cp values were calculated. The average amplification efficiency (2.11) and the PCR efficiency (111%) for the reactions were also calculated. Table 33 shows that the *C. tropicalis* molecular beacon probe was used successfully to detect *Candida tropicalis* target nucleic acid molecules using genomic DNA isolated from *C. tropicalis*, even in the presence *C. parapsilosis* nucleic acid molecules, as well as molecular beacons for both of these *Candida* species. Notably, the amplification efficiency and PCR efficiency in the multiplex reaction was similar to that observed in the singleplex reaction (see Example 12 and Table 27).

TABLE 33

C. tropicalis detection in multiplex rx (C. tropicalis, C. parpasilosis)

| copies/rx | Cp1 | Cp2 | Cp3 | Cp4 | Average | Std Cp | CV |
|---|---|---|---|---|---|---|---|
| 50000 | 22.75 | 22.75 | 22.94 | 22.43 | 22.72 | 0.21 | 0.9% |
| 5000 | 26.1 | 26.05 | 26.33 | 26.09 | 26.14 | 0.13 | 0.5% |
| 500 | 29.19 | 29.45 | 29.51 | 29.29 | 29.36 | 0.15 | 0.5% |
| 50 | 32.26 | 32.24 | 32.69 | 32.15 | 32.34 | 0.24 | 0.7% |
| 5 | 35 | 35 | 35 | 35 | 35.00 | 0.00 | 0.0% |
| no template | ND | ND | ND | ND | | | |
| slope | −3.08 | | | | | | |
| | 0.33 | | | | | | |
| | 2.11 | | | | | | |
| | 111% | | | | | | |

Example 18: Detection of Candida Species Using a Beat Denatured Fungal Lysate To determine if the molecular beacon probes could be used for the detection of *Candida* cells directly using a 95° C. heat denaturation step to lyse the *Candida* cells instead of mechanical lysis, such as by bead beating, we spiked 50 uL of TE containing Coulter counted *Candida* cells directly into a 96-well plate. We then added the molecular beacon probe-containing master mix on top of the cells and conducted an RT-PCR using the parameters described in Example 1 above.

Real-time PCR data are provided below (Tables 34-38) for PCR reactions, each of which contains *C. albicans*, *C. glabrata*, *C. krusei*, *C. parapsilosis*, and *C. tropicalis* genomic DNA prepared from heat denatured lysates containing the indicated number of cells. As shown in Tables 34-38, the *Candida* specific molecular beacon probes (*C. albicans*: SEQ ID NO: 1; *C. glabrata*: SEQ ID NO: 3; *C. krusei*: SEQ ID NO: 6; *C. parapsilosis*: SEQ ID NO: 4; and *C. tropicalis*: SEQ ID NO: 2) successfully detected the indicated *Candida* nucleic acid molecules following lysis by heat denaturation. Detection was possible even up to 10 cells.

TABLE 34

Detection of *C. albicans* in fungal lysate

*C. albicans*

| cells | Cp1 | Cp2 | Cp3 | Average | Std Cp | CV |
|---|---|---|---|---|---|---|
| 1000 | 37.18 | 36.78 | 37.4 | 37.12 | 0.31 | 0.8% |
| 100 | ND | 40 | 40 | 40.00 | 0.00 | 0.0% |
| 50 | 40 | 39.09 | ND | 39.55 | 0.64 | 1.6% |
| 10 | 40 | ND | ND | 40.00 | | |
| no template | ND | ND | ND | | | |

TABLE 35

Detection of *C. glabrata* in fungal lysate

*C. glabrata*

| cells | Cp1 | Cp2 | Cp3 | Average | Std Cp | CV |
|---|---|---|---|---|---|---|
| 1000 | 34 | 33.99 | 34.31 | 34.10 | 0.18 | 0.5% |
| 100 | 37.61 | 36.63 | 36.26 | 36.83 | 0.70 | 1.9% |
| 50 | 40 | 36.85 | 39.43 | 38.76 | 1.68 | 4.3% |
| 10 | ND | 40 | 40 | 40.00 | 0.00 | 0.0% |
| no template | ND | ND | ND | | | |

TABLE 36

Detection of *C. krusei* in fungal lysate

*C. krusei*

| cells | Cp1 | Cp2 | Cp3 | Average | Std Cp | CV |
|---|---|---|---|---|---|---|
| 1000 | 29.53 | 28.98 | 29.00 | 29.17 | 0.31 | 1.1% |
| 100 | 32.51 | 32.54 | 32.26 | 32.44 | 0.15 | 0.5% |
| 50 | 33.28 | 33.48 | 33.54 | 33.43 | 0.14 | 0.4% |
| 10 | 35.74 | 35.76 | 36.11 | 35.87 | 0.21 | 0.6% |
| no template | ND | ND | ND | | | |

TABLE 37

Detection of *C. parapsilosis* in fungal lysate

*C. parapsilosis*

| cells | Cp1 | Cp2 | Cp3 | Average | Std Cp | CV |
|---|---|---|---|---|---|---|
| 1000 | 36.16 | 35.63 | 35.35 | 35.71 | 0.41 | 1.2% |
| 100 | 37.78 | 38.59 | 39.19 | 38.52 | 0.71 | 1.8% |
| 50 | 39.54 | 40 | 38.28 | 39.27 | 0.89 | 2.3% |
| 10 | ND | 40 | ND | | | |
| no template | ND | ND | ND | | | |

TABLE 38

Detection of *C. tropicalis* in fungal lysate

*C. tropicalis*

| cells | Cp1 | Cp2 | Cp3 | Average | Std Cp | CV |
|---|---|---|---|---|---|---|
| 1000 | 32.93 | 33.37 | 33.2 | 33.17 | 0.22 | 0.7% |
| 100 | 36.03 | 36.23 | 36.82 | 36.36 | 0.41 | 1.1% |
| 50 | 37.14 | 37.74 | 37.58 | 37.49 | 0.31 | 0.8% |
| 10 | 40 | 40 | 40 | 40.00 | 0.00 | 0.0% |
| no template | ND | 40 | ND | | | |

As positive controls, the same *Candida* nucleic acid molecules prepared via the PCR described above were detected using *Candida* specific probes (*C. albicans*: SEQ ID NOs: 13 and 14; *C. glabrata*: SEQ ID NOs: 17 and 18; *C. krusei*: SEQ ID NOs: 15 and 16; *C. parapsilosis*: SEQ ID NOs: 21 and 22; and *C. tropicalis*: SEQ ID NOs: 19 and 20) conjugated to magnetic nanoparticles for use in an NMR based assay, as is described above. In short, the hybridization induced agglomeration assays is performed by aliquoting 15 μL of the amplification reaction into 0.2 mL thin walled PCR tubes and incubating within a sodium phosphate hybridization buffer (4×SSPE) with the indicated pairs of oligonucleotide probe derivatized nanoparticles at a final iron concentration of 0.2 mM iron per reaction. Hybridization reactions were incubated for 3 minutes at 95° C. followed by 30 minutes incubation at 60° C. within a shaking-incubator set at an agitation speed of 1000 rpm (Vortemp, LabNet International). Hybridized samples are then placed in a 37° C. heating block to equilibrate the temperature to that of the MR reader for 3 minutes. Each sample is then subjected to a 5 second vortexing step (3000 rpm) and inserted into the MR reader for T2 measurement. The baseline T2 signal is ~30-40 msec, thus a signal<45 indicates no target DNA is present.

As shown in Tables 39-43, there is 97% concordance between the detected *Candida* cells via the molecular beacon probes and the T2 detection reactions run on the RT-PCR generated amplicons. We observe one instance in which *C. glabrata* nucleic acid molecules from the sample prepared using cells was not detected via RT-PCR but was detected with the NMR-based T2 assay (compare Cp1 in Table 35 to Rep1 in Table 40), and one sample in which *C. tropicalis* nucleic acid molecules from the sample prepared using 10 cells was detected via RT-PCR but not by the NMR-based T2 assay (compare Cp1 in Table 38 to Rep1 in Table 43). These discordant results are highlighted in bold and italics in the tables below.

TABLE 39

*C. albicans* RT-PCR product, T2 detection

| Rep1 | Rep2 | Rep3 | Average | Std Cp | CV |
|---|---|---|---|---|---|
| 253.8 | 239.06 | 253.78 | 248.88 | 8.50 | 3.4% |
| 36.09 | 223.18 | 250.38 | 236.78 | 19.23 | 8.1% |
| 251.33 | 233.13 | 36.72 | 242.23 | | 0.0% |
| 220.19 | 36.62 | 36.17 | 220.19 | | 0.0% |
| 36.91 | 36.58 | 38.53 | 37.34 | 1.04 | 2.8% |

TABLE 40

*C. glabrata* RT-PCR product, T2 detection

| Rep1 | Rep2 | Rep3 | Average | Std Cp | CV |
|---|---|---|---|---|---|
| 102.97 | 98.49 | 96.11 | 99.19 | 3.48 | 3.5% |
| 117.8 | 121.86 | 112.59 | 117.42 | 4.65 | 4.0% |
| 125.25 | 108.89 | 180.44 | 138.19 | 37.49 | 27.1% |
| 273.68 | 139.8 | 189.81 | 201.10 | 67.65 | 33.6% |
| 35.16 | 35.19 | 36.64 | 35.66 | 0.85 | 2.4% |

TABLE 41

*C. krusei* RT-PCR product, T2 detection

| Rep1 | Rep2 | Rep3 | Average | Std Cp | CV |
|---|---|---|---|---|---|
| 105.92 | 116.9 | 104.72 | 109.18 | 6.71 | 6.1% |
| 106.36 | 118.04 | 107.04 | 110.48 | 6.56 | 5.9% |
| 110.11 | 119.5 | 109.77 | 113.13 | 5.52 | 4.9% |

TABLE 41-continued

C. krusei RT-PCR product, T2 detection

| Rep1 | Rep2 | Rep3 | Average | Std Cp | CV |
|---|---|---|---|---|---|
| 122.32 | 128.94 | 119.36 | 123.54 | 4.91 | 4.0% |
| 35.63 | 35.26 | 37.55 | 36.15 | 1.23 | 3.4% |

TABLE 42

C. parapsilosis RT-PCR product, T2 detection

| Rep1 | Rep2 | Rep3 | Average | Std Cp | CV |
|---|---|---|---|---|---|
| 303.44 | 307.97 | 279.39 | 296.93 | 15.36 | 5.2% |
| 343.76 | 327.83 | 361.66 | 344.42 | 16.92 | 4.9% |
| 390.33 | 464.65 | 315.78 | 390.25 | 74.44 | 19.1% |
| 32.27 | 448.74 | 32.66 | | | |
| 31.98 | 32.02 | 32.94 | 32.31 | 0.54 | 1.7% |

TABLE 43

C. tropicalis RT-PCR product, T2 detection

| Rep1 | Rep2 | Rep3 | Average | Std Cp | CV |
|---|---|---|---|---|---|
| 279.39 | 471.34 | 441.24 | 397.3233 | 103.2362 | 26.0% |
| 361.66 | 438.41 | 435.62 | 411.90 | 43.53 | 10.6% |
| 315.78 | 452.44 | 436.73 | 401.65 | 74.78 | 18.6% |
| 32.66 | 475.71 | 530.58 | 346.32 | 273.02 | 78.8% |
| 36.04 | 35.07 | 35.36 | 35.49 | 0.50 | 1.4% |

Example 19: Detection of Candida Species Using Melt-Curve Analysis

Because the Tm of the Candida species-specific molecular beacon probes differ by at least 1 degree, it is possible to multiplex the beacon probes with the same fluorophore and deconvolute the signals using melt curve analysis alone. Molecular beacon probes for C. albicans (SEQ ID NO: 1), C. glabrata (SEQ ID NO: 3), C. krusei (SEQ ID NO: 6), C. parapsilosis (SEQ ID NO: 4), and C. tropicalis (SEQ ID NO: 2) were all labeled with a HEX fluorophore and added at 300 nm concentration to a single sample that included target nucleic acid molecules for each of the Candida species.

Figure 9A:
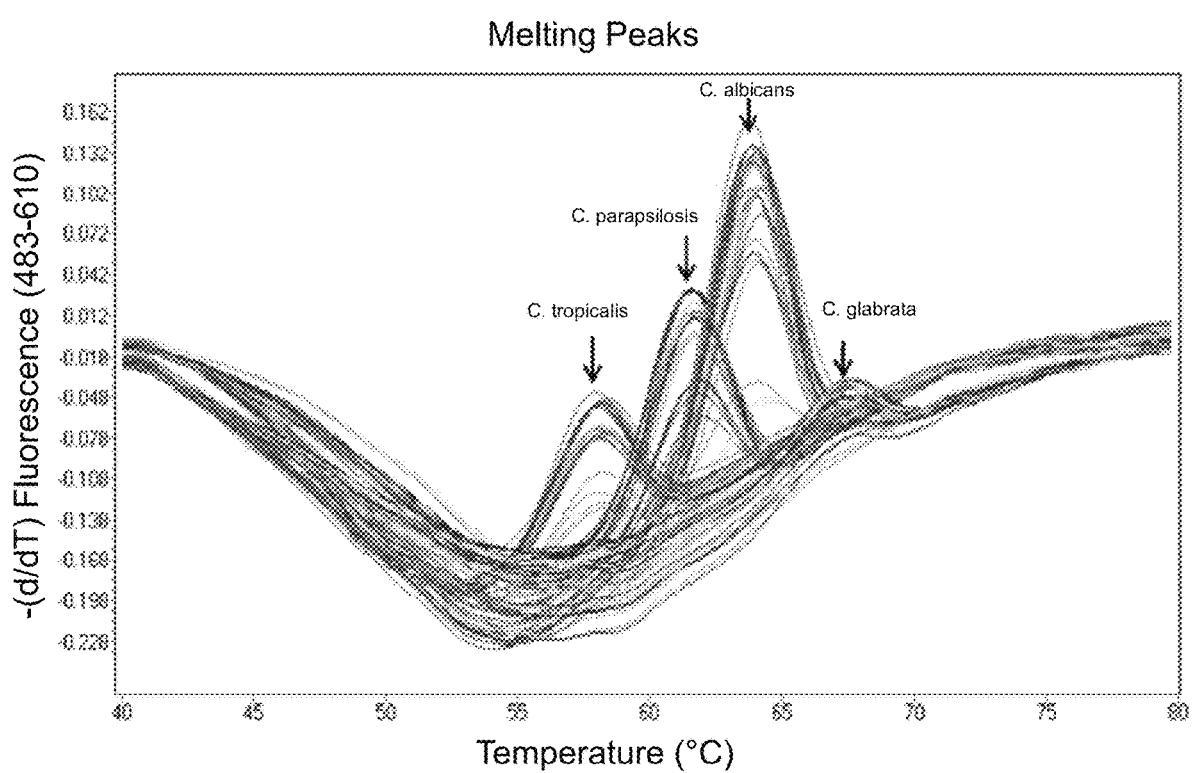
FIGS. 9A and 9B are graphs showing nucleic acid denaturation melt curves in a multiplex reaction that includes *Candida* species-specific nucleic acid molecules from, and *Candida* species-specific molecular beacon probes for, *C. albicans, C. glabrata, C. parapsilosis*, and *C. tropicalis* (FIG. 9A) and for *C. albicans* and *C. krusei* (FIG. 9B). The *Candida*-specific molecular beacon probes used in the multiplex reactions are all labeled with a HEX fluorophore. The presence of nucleic acid molecules for each *Candida* species is determined by detecting a decrease in fluorescence as the sample is heated through the melting temperature (Tm) of each *Candida* species-specific molecular beacon probe. A decrease in fluorescence is observed only when hybridized beacon probes melt off their target nucleic acid molecules and the step-loop structure of the probes reforms. No melt curve is observed when the probe-specific target nucleic acid molecules are not present in the reaction.
Figure 9B:
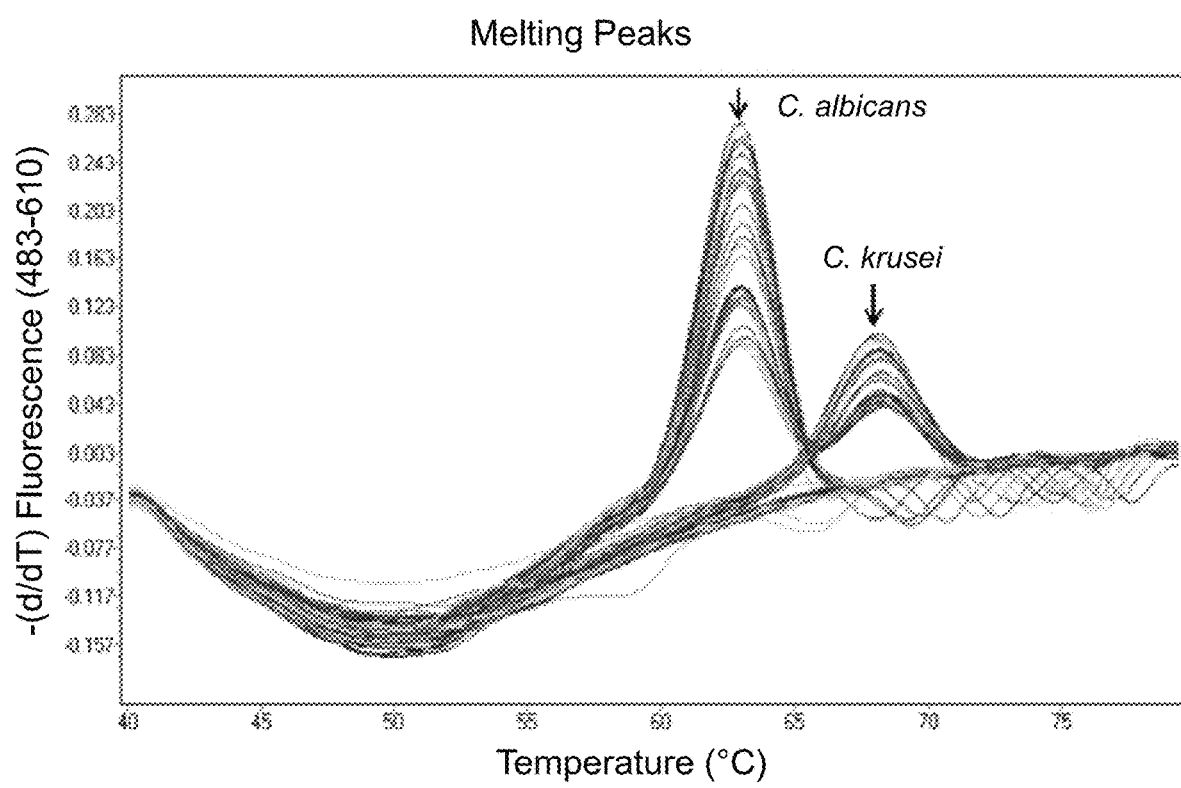

As shown in FIGS. 9A and 9B, the presence of target nucleic acid molecules for the indicated Candida species targets was determined within the sample simply by looking for the presence of the species-specific melt curve and using the Tm as a means of species identification. Use of the melt-curve analysis abrogates the need to use multiple different fluorophores in a single multiplexed reaction and simplifies the instrument design. It should be noted that there is no melt curve when the target nucleic acid molecule is not present in the reaction. The Tm is the temperature at which a decrease in fluorescence is observed and this only occurs when the hybridized beacon probe is melted off the target and the beacon probe stem-loop structure reforms.

Example 20: Molecular Beacon Analysis Using a Post-Blood Culture

To perform a blood culture analysis, up to 10 ml of a blood sample from a patient suspected of having a blood systemic infection are incubated in a blood culture bottle. The blood culture media typically are composed to promote the growth of either aerobic or anaerobic pathogens. Depending on the specific requirements for growth of the suspected pathogen, culture media is composed of a number of nutrients that feed pathogens and resins that absorb antibiotics/antifungals that might be present in the blood specimen and inhibit growth. When a pathogen reaches a concentration of $10^6$ to $10^8$ CFU/mL, it produces enough carbon dioxide through its normal metabolic pathways to activate the blood culture detection system, thus signaling a positive blood culture for the original sample. At this time, a sample from this culture bottle is aliquoted onto a species-specific detection methodology, which may be a culture plate or another system that identifies the pathogenic species and assesses its susceptibility to antimicrobials (e.g., Vitek 2, Biomeriuex, Durham, N.C.). Species identification is typically performed over a day, although it can be significantly longer.

In order to expedite the species identification of Candida that may be present in a blood culture, a singleplex or multiplex reaction for detecting one or more Candida species, according to the methods described in, e.g., Examples 1-19 above, can be used. The protocol involves adding a sample from the positive blood culture bottle to the singleplex or multiplex reaction, centrifuging the sample to pellet the pathogen cells, which may be optionally washed one or more times to remove interferents from the blood culture media, lysing the cells and using the nucleic acid molecules from the cells in a molecular beacon protocol described in one or more of Examples 1-19 above. This process would rapidly and with high fidelity determine the presence and species identification of one or more Candida species in the blood sample; a positive result indicates Candida infection in the patient.

Species identification could rapidly assist in appropriate administration of antifungals as several Candida species are more resistant to fluconazole (e.g., Candida glabrata and Candida krusei).

Example 21: Use of the Molecular Beacon Assay to Detect Candida in a Whole Blood Sample The Candida specific molecular beacon probes described herein can be used to detect the presence of Candida in a whole blood sample from a patient suspected of having a Candida infection. Generally, the protocol involves i) obtaining a 1-10 mL sample of whole blood from the patient; ii) lysing the red blood cells (e.g., using an ammonium chloride iso-osmotic solution, a detergent lysis solution, or a hypotonic lysis solution); iii) centrifuging the lysed sample, e.g., at 3,000 g to 12,000 g for 5 minutes to pellet the Candida cells; iv) removing and discarding the supernatant; v) washing the pellet with an equal volume of TE (equivalent to the blood specimen volume) or less; vi) centrifuging the resuspended Candida cells at 3,000 g to 12,000 g for 5 minutes to pellet the Candida cells; vii) removing and discarding the supernatant; viii) optionally repeating steps v)-vii); ix) adding 50-150 uL of 1×TE; x) adding 300 mg of 500 to 800 micron beads (e.g., silica or zirconium oxide (yttrium stabilized) beads); xi) vortexing at maximum power (3000 rpm) for 5-10 minutes to lyse the Candida cells; xii) aliquoting 10 to 50 uL of the cell lysate into a molecular beacon probe-containing PCR mastermix on, e.g., a 96 well plate (see, e.g., Example 1); and xiii) running an RT-PCR reaction and detecting the presence of Candida according to one or more of the methods described in Examples 1-19.

Example 22: Use of the Molecular Beacon Assay to Detect *Candida* in a Urine Sample The *Candida* specific molecular beacon probes described herein can be used to detect the presence of *Candida* in a urine sample from a patient suspected of having a *Candida* infection. Generally, the protocol involves i) obtaining a 1-10 mL sample of urine from the patient; ii) centrifuging the sample at 3,000 g to 12,000 g to pellet the *Candida* cells; iii) removing and discarding the supernatant; iv) washing the pellet with an equal volume of TE or less (equivalent to the urine specimen volume); v) centrifuging at 3,000 g to 12,000 g for 5 minutes to pellet the *Candida* cells; vi) removing and discarding the supernatant; vii) optionally repeating steps iv)-vi); viii) adding 50-150 uL of 1×TE; ix) adding 300 mg of 500 to 800 micron beads (e.g., silica or zirconium oxide (yttrium stabilized) beads); x) vortexing at maximum power (3000 rpm) for 5-10 minutes to lyse the *Candida* cells; xi) aliquoting 10 to 50 uL of cell lysate into molecular beacon probe-containing PCR mastermix on, e.g., a 96 well plate (see, e.g., Example 1); and xii) running an RT-PCR reaction and detecting the presence of *Candida* according to one or more of the methods described in Examples 1-19.

OTHER EMBODIMENTS

While certain novel features of this invention shown and described below are pointed out in the annexed claims, the invention is not intended to be limited to the details specified, since a person of ordinary skill in the relevant art will understand that various omissions, modifications, substitutions and changes in the forms and details of the invention illustrated and in its operation may be made without departing in any way from the spirit of the present invention. No feature of the invention is critical or essential unless it is expressly stated as being "critical" or "essential."

Those skilled in the art will recognize or be able to ascertain using no more than routine experimentation many equivalents to the specific embodiments of the invention described herein. Such equivalents are intended to be encompassed in the scope of the present invention.

All publications, patents, and patent applications mentioned in this specification are herein incorporated by reference to the same extent as if each independent publication, patent, or patent application was specifically and individually indicated to be incorporated by reference.

The invention claimed is:

1. A nucleic acid probe comprising a sequence having at least 95% sequence identity to the sequence of SEQ ID NO: 1 conjugated to a detection moiety.

2. The nucleic acid probe of claim 1, wherein said detection moiety comprises a fluorescent label.

3. The nucleic acid probe of claim 2, wherein the fluorescent label is at a first end of said nucleic acid probe and wherein the nucleic acid probe further comprises a quencher at an opposite end of said nucleic acid probe.

4. The nucleic acid probe of claim 1, wherein the nucleic acid probe comprises the sequence of SEQ ID NO: 1.

5. The nucleic acid probe of claim 4, wherein the sequence of the nucleic acid probe consists of the sequence of SEQ ID NO: 1.

6. A composition comprising the nucleic acid probe of claim 1.

7. The composition of claim 6, further comprising at least one nucleic acid probe having a sequence with at least 95% sequence identity to a sequence selected from the group consisting of SEQ ID NOs: 2, 4, and 5.

8. The composition of claim 7, wherein the at least one nucleic acid probe has a sequence selected from the group consisting of SEQ ID NOs: 2, 4, and 5.

9. The composition of claim 8, wherein the at least one nucleic acid probe consists of a sequence selected from the group consisting of SEQ ID NOs: 2, 4, and 5.

10. The composition of claim 6, wherein the detection moiety comprises a fluorescent label.

11. The composition of claim 10, wherein the fluorescent label is at a first end of the nucleic acid probe and wherein the nucleic acid probe comprises a quencher at an opposite end of the nucleic acid probe.

12. The composition of claim 6, further comprising one or more sample lysis reagents, fungal lysis reagents, fluorescence or nuclear magnetic resonance (NMR)-based reagents for detection of *Candida* species, and nucleic acid amplification reagents.

13. A kit comprising the composition of claim 6.

14. The kit of claim 13, further comprising one or more sample lysis reagents, fungal lysis reagents, fluorescence or nuclear magnetic resonance (NMR)-based reagents for detection of *Candida* species, and nucleic acid amplification reagents.

15. The composition of claim 6, wherein the nucleic acid probe has the sequence of SEQ ID NO: 1.

16. The composition of claim 15, wherein the sequence of the nucleic acid probe consists of the sequence of SEQ ID NO: 1.

17. The composition of claim 15, wherein the detection moiety comprises a fluorescent label.

18. The composition of claim 7, wherein the at least one nucleic acid probe further comprises a fluorescent label at a first end of the at least one nucleic acid probe and a quencher at an opposite end of the at least one nucleic acid probe.

19. The composition of claim 7, further comprising one or more sample lysis reagents, fungal lysis reagents, fluorescence or nuclear magnetic resonance (NMR)-based reagents for detection of *Candida* species, and nucleic acid amplification reagents.

20. The kit of claim 13, wherein the nucleic acid probe has the sequence of SEQ ID NO: 1.

21. The kit of claim 13, further comprising at least one nucleic acid probe having a sequence with at least 95% sequence identity to a sequence selected from the group consisting of SEQ ID NOs: 2, 4, and 5.

22. The kit of claim 21, wherein the at least one nucleic acid probe has a sequence selected from the group consisting of SEQ ID NOs: 2, 4, and 5.

23. The kit of claim 22, wherein the at least one nucleic acid probe consists of a sequence selected from the group consisting of SEQ ID NOs: 2, 4, and 5.

* * * * *